(12) United States Patent
Knopf et al.

(10) Patent No.: US 7,960,343 B2
(45) Date of Patent: Jun. 14, 2011

(54) ACTIVIN-ACTRIIA ANTAGONISTS AND USES FOR DECREASING OR INHIBITING FSH SECRETION

(75) Inventors: John Knopf, Carlisle, MA (US); Jasbir Seehra, Lexington, MA (US); Matthew L. Sherman, Newton, MA (US)

(73) Assignee: Acceleron Pharma Inc., Cambridge, MA (US)

( * ) Notice: Subject to any disclaimer, the term of this patent is extended or adjusted under 35 U.S.C. 154(b) by 89 days.

(21) Appl. No.: 12/284,112

(22) Filed: Sep. 17, 2008

(65) Prior Publication Data

US 2009/0118188 A1 May 7, 2009

Related U.S. Application Data

(60) Provisional application No. 60/994,399, filed on Sep. 18, 2007.

(51) Int. Cl.
*A61K 38/00* (2006.01)
(52) U.S. Cl. ........................................... 514/9.7
(58) Field of Classification Search ........................ None
See application file for complete search history.

(56) References Cited

U.S. PATENT DOCUMENTS

| | | | |
|---|---|---|---|
| 4,973,577 A | 11/1990 | Vale, Jr. et al. | |
| 5,118,667 A | 6/1992 | Adams et al. | |
| 5,658,876 A * | 8/1997 | Crowley et al. | 514/2 |
| 5,824,637 A * | 10/1998 | Crowley et al. | 514/2 |
| 5,847,078 A | 12/1998 | Eto et al. | |
| 5,885,794 A | 3/1999 | Mathews et al. | |
| 6,093,547 A | 7/2000 | Jin et al. | |
| 6,132,988 A | 10/2000 | Sugino et al. | |
| 6,162,896 A | 12/2000 | Mathews et al. | |
| 6,451,334 B2 | 9/2002 | Perrine | |
| 6,599,876 B2 | 7/2003 | Kojima | |
| 6,605,699 B1 | 8/2003 | Ni et al. | |
| 6,656,475 B1 | 12/2003 | Lee et al. | |
| 6,692,925 B1 | 2/2004 | Miyazono et al. | |
| 6,696,260 B1 | 2/2004 | Lee et al. | |
| 6,835,544 B2 | 12/2004 | Mathews et al. | |
| 6,891,082 B2 | 5/2005 | Lee et al. | |
| 7,192,717 B2 | 3/2007 | Hill et al. | |
| 7,202,210 B2 | 4/2007 | Wolfman et al. | |
| 7,261,893 B2 | 8/2007 | Veldman et al. | |
| 7,320,789 B2 | 1/2008 | Aghajanian et al. | |
| 7,560,441 B2 | 7/2009 | Wolfman et al. | |
| 7,612,041 B2 | 11/2009 | Knopf et al. | |
| 2003/0083251 A1 | 5/2003 | Westenfelder | |
| 2003/0144203 A1 * | 7/2003 | Bowen | 514/12 |
| 2004/0197828 A1 | 10/2004 | Gaddy | |
| 2004/0209805 A1 | 10/2004 | Phillips et al. | |
| 2004/0223966 A1 | 11/2004 | Wolfman et al. | |
| 2005/0257278 A1 | 11/2005 | Lee et al. | |
| 2006/0068468 A1 | 3/2006 | Knopf et al. | |
| 2006/0210657 A1 | 9/2006 | Chou | |
| 2007/0048830 A1 | 3/2007 | Gilbert et al. | |
| 2007/0149455 A1 | 6/2007 | Wolfman et al. | |
| 2007/0172956 A1 | 7/2007 | Magari et al. | |
| 2007/0184052 A1 | 8/2007 | Lin et al. | |
| 2007/0249022 A1 | 10/2007 | Knopf et al. | |
| 2007/0275895 A1 | 11/2007 | Duan et al. | |
| 2007/0292885 A1 | 12/2007 | Bejanin et al. | |
| 2008/0021104 A1 | 1/2008 | Tarallo | |
| 2008/0075692 A1 | 3/2008 | Perrine | |
| 2008/0089897 A1 | 4/2008 | Wolfman | |
| 2008/0139590 A1 | 6/2008 | Qian et al. | |
| 2009/0005308 A1 | 1/2009 | Knopf et al. | |
| 2009/0017019 A1 | 1/2009 | Shields et al. | |
| 2009/0047281 A1 | 2/2009 | Sherman | |
| 2009/0074768 A1 | 3/2009 | Knopf et al. | |
| 2009/0087433 A1 | 4/2009 | Wolfman et al. | |
| 2009/0098113 A1 | 4/2009 | Knopf et al. | |
| 2009/0099086 A1 | 4/2009 | Knopf et al. | |
| 2009/0118188 A1 | 5/2009 | Knopf et al. | |
| 2009/0142333 A1 | 6/2009 | Knopf et al. | |
| 2009/0148436 A1 | 6/2009 | LaVallie et al. | |
| 2009/0163417 A1 | 6/2009 | Sherman | |

FOREIGN PATENT DOCUMENTS

| | | |
|---|---|---|
| EP | 1174149 A1 | 1/2002 |
| WO | WO-92/20793 A1 | 11/1992 |
| WO | WO-95/10611 A1 | 4/1995 |
| WO | WO95/29685 * | 11/1995 |
| WO | WO-99/06559 A1 | 2/1999 |
| WO | WO-00/43781 A2 | 7/2000 |
| WO | WO-02/10214 A2 | 2/2002 |
| WO | WO-02/43759 A2 | 6/2002 |
| WO | WO-02/085306 A2 | 10/2002 |
| WO | WO-03/006057 A1 | 1/2003 |
| WO | WO03/053219 * | 7/2003 |
| WO | WO-03/072808 A1 | 9/2003 |
| WO | WO-2004/039948 | 5/2004 |
| WO | WO-2004108157 A2 | 12/2004 |
| WO | WO-2005/009460 | 2/2005 |
| WO | WO-2005/028517 | 3/2005 |
| WO | WO-2005/097825 A2 | 10/2005 |
| WO | WO-2005094871 A2 | 10/2005 |
| WO | WO-2006002387 A2 | 1/2006 |
| WO | WO-2006/012627 | 2/2006 |
| WO | WO-2006020884 A2 | 2/2006 |
| WO | WO-2006039400 A2 | 4/2006 |
| WO | WO-2006083183 A1 | 8/2006 |
| WO | WO-2006088972 | 8/2006 |
| WO | WO-2007/062188 | 5/2007 |
| WO | WO-2007053775 A1 | 5/2007 |
| WO | WO-2007067616 A2 | 6/2007 |
| WO | WO-2008031061 | 3/2008 |
| WO | WO-2008060139 A1 | 5/2008 |
| WO | WO-2008076437 A2 | 6/2008 |
| WO | WO-2008097541 A2 | 8/2008 |
| WO | WO-2008100384 A2 | 8/2008 |
| WO | WO-2008109167 A2 | 9/2008 |
| WO | WO-2009019504 A1 | 2/2009 |
| WO | WO-2009019505 A2 | 2/2009 |
| WO | WO-2009137613 A2 | 11/2009 |

OTHER PUBLICATIONS

Website downloaded on Jun. 14, 2010, about.com/reports/000101_2.htm?p=1; 11 pages total.*

(Continued)

*Primary Examiner* — Bridget E Bunner
*Assistant Examiner* — Christina Borgeest
(74) *Attorney, Agent, or Firm* — Ropes & Gray LLP

(57) ABSTRACT

In certain aspects, the present invention provides compositions and methods for decreasing FSH levels in a patient. The patient may, for example, be diagnosed with an FSH-related disorder or desire to delay or inhibit germ cell maturation.

40 Claims, 32 Drawing Sheets
(17 of 32 Drawing Sheet(s) Filed in Color)

OTHER PUBLICATIONS

Harrison et al., JBC, 2004; 279: 28036-28044.*
Raju et al., Biochem Biophys Res Commun. 2006; 341: 797-803.*
Gregoriadis et al., FEBS, 1993; 314: 271-276.*
Acceleron Pharma Presents Positive Phase 1 Results Demonstrating ACE-011 Increases Markers of Bone Formation, Acceleron Pharma, pp. 1-2, retrieved from the Internet, www.acceleronpharma.com/contents/news/press-releases/detail.jsp/q/news-id/47> (2007).
Akel et al., Neutralization of Autocrine Transforming Growth Factor -β in Human Cord Blood CD34+CD38-Lin—Cells Promotes Stem-Cell-Factor-Mediated Erythropoietin-Independent Early Erythroid Progenitor Development and Reduces Terminal Differentiation. Stem Cells vol. 21; pp. 557-567 (2003).
Akpan, I., et al., "The effects of a soluble activin type IIB receptor on obesity and insulin sensitivity," International Journal of Obesity, 33(11):1265-1273 (2009), Published Nov. 2009, Advance online publication date was Aug. 11, 2009, Abstract, pp. 1266, 1269.
Broxmeyer, H.E., et al, "Selective and indirect modulation of human multipotential and erythroid hematopoietic progenitor cell proliferation by recombinant human activin and inhibin," Proc. Natl. Acad. Sci. USA, 85:9052-9056 (1988).
Burdette et al., Activin A mediates growth inhibition and cell cycle arest through Smads in human breast cancer cells. Cancer Research, 65(17):7968-7975; Abstract (2005).
Centrella et al., "Activin-A Binding and Biochemical Effects in Osteoblast-Enriched Cultures from Fetal-Rat Parietal Bone," Molecular and Cellular Biology, 11(1):250-58 (1991).
Chen, Y.G., et al. "Regulation of Cell Proliferation, Apoptosis, and Carcinogenesis by Activin," Exp. Biol. Med., 227(2):75-87 (2002).
Coerver, et al., "Activin Signaling through Activin Receptor Type II Causes the Cachexia-Like Symptoms in Inhibin-Deficent Mice," 10(5):534-543 (1996).
Daluiski et al., "Bone Morphogenetic Protein-3 is a Negative Regulator of Bone Density," Nature Genetics, 27:84-88 (2001).
del Re et al., "Reconstitution and Analysis of Soluble Inhibin and Activin Receptor Complexes in a Cell-free System," The Journal of Biological Chemistry, 279(51):53126-53135 (2004).
Donaldson, et al., "Activin and inhibin binding to the soluble extracellular domain of activin receptor II", Endocrinology 140(4):1760-1766(1999).
Donaldson, et al., "Molecular Cloning and Binding Properties of the Human Type II Activin Receptor", Biochemical and Biophysical Research Communications, 184(1):310-316(1992).
Fafioffe, et al.,"Activin and inhibin receptor gene expression in the ewe pituitary throughout the oestrous cycle," Journal of Endocrinology, vol. 182, pp. 55-68 (2004).
Frigon, N.L., et al, "Regulation of Globin Gene Expression in Human K562 Cells by Recombinant Activin A," Blood, 79(3):765-772 (1992).
Fuller et al., "Activin A Is an Essential Cofactor for Osteoclast Induction," Biochemical and Biophysical Research Communications, 268:2-7 (2000).
Funaba et al., "Expression and Localization of Activin Receptors During Endochondral Bone Development," European Journal of Endocrinology, 144:63-71 (2001).
Gaddy-Kurten et al., "Inhibin Suppresses and Activin Stimulates Osteoblastogenesis and Osteoclastogenesis in Murine Bone Marrow Cultures," Endocrinology, 143(1):74-83 (2002).
Gamer et al., "BMP-3 is a Novel Inhibitor of Both Activin and BMP-4 Signaling in Xenopus Embryos," Developmental Biology, 285:156-168 (2005).
Ge, G., et al., "GDF11 Forms a Bone Morphogenetic Protein 1-Activated Latent Complex That Can Modulate Nerve Growth Factor-Induced Differentiation of PC12 Cells", Molecular and Cellular Biology, 25(14):5846-5858 (2005).
GenBank NM_001106, Homo sapiens activin A receptor, type IIB (ACVR2B), mRNA, http://www.ncbi.nlm.nih.gov/entrez/viewer.fcgi?db=nucleotide&val=116734707 (Downloaded on Jan. 29, 2007).
Gonzalez-Cadavid, N.F., et al., "Organization of the human myostatin gene and expression in healthy men and HIV-infected men with muscle wasting," PNAS, 95:14938-14943 (1998).

Gray, et al., "Identification of a binding site on the type II activin receptor for activin and inhibin", Journal of Biological Chemistry, 275(5):3206-3212(2000).
Greenwald, et al., "The BMP7/ActRII Extracellular Domain Complex Provides New Insights into the Cooperative Nature of Receptor Assembly," Molecular Cell, vol. 11, 605-617 (2003).
Gupta, V. et al., "Transforming Growth Factor-b Superfamily: Evaluation as Breast Cancer Biomarkers and Preventive Agents," Current Cancer Drug Targets, 4:165-182 (2004).
Hamrick et al., "Bone Mineral Content and Density in the Humerus of Adult Myostatin-Deficient Mice," Calcified Tissue International, 71:63-68 (2002).
Hamrick, "Increased Bone Mineral Density in the Femora of GDF8 Knockout Mice," The Anatomical Record, Part A 272A:388-391 (2003).
Hamrick, M.W., et al., "Femoral Morphology and Cross-sectional Geometry of Adult Myostatin-deficient Mice," Bone, 27(3):343-349 (2000).
Harrison, et al., "Antagonists of activin signaling: mechanisms and potential biological applications," Trends in Endocrinology and Metabolism, 16(2):73-78 (2005).
Hashimoto et al., "Functional Regulation of Osteoblastic Cells by the Interaction of Activin-A with Follistatin," The Journal of Biological Chemistry, 267(7):4999-5004 (1992).
Hemmati-Brivanlou, A., et al., "A truncated activin receptor inhibits mesoderm induction and formation of axial structures in Xenopus embryos," Nature, 359:609-614 (1992).
Hilden, K., et al., "Expression of Type II Activin Receptor Genes During Differentiation of Human K562 Cells and cDNA Cloning of the Human Type IIB Activin Receptor," Blood, 83(8):2163-2170 (1994).
Hill, J.J., et al., "Regulation of Myostatin in Vivo by Growth and Differentiation Factor-Associated Serum Protein-1: A Novel Protein with Protease Inhibitor and Follistatin Domains," Molecular Endocrinology, 17(6):1144-1154 (2003).
Ikenoue et al., "Inhibitory Effects of Activin-A on Osteoblast Differentiation During Cultures of Fetal Rat Calvarial Cells," Journal of Cellular Biochemistry, 75:206-214 (1999).
Kaspar, B.K., et al., "Retrograde Viral Delivery of IGF-1 Prolongs Survival in a Mouse ALS Model," Science, 301:839-842 (2003).
Knight, "Roles of Inhibins, Activins, and Follistatin in the Female Reproductive System," Frontiers in Neuroendocrinology, 17:476-509 (1996).
Kosaki, R., et al., "Left-Right Axis Malformations Associated With Mutations in ACVR2B, the Gene for Human Activin Receptor Type IIB," American Journal of Medical Genetics, 82:70-76 (1999).
Koseki, et al., "Role of TCF-b Family in Osteoclastogenesis Induced by RANKL," Cellular Signaling, 14:31-36 (2002).
Krneta, J., et al., "Dissociation of Angiogenesis and Tumorigenesis in Follistatin- and Activin-Expressing Tumors," Cancer Research, 66(11):5686-5695 (2006).
Krystal et al., Transforming Growth Factor β1 Is an Inducer of Erythroid Differentiation. J. Exp. Med. vol. 180 pp. 851-860 (1994).
Kubanek, B., "Introduction: The Role of the Microenvironment and Cytokines on the Modulation of Erythropoiesis," Annals New York Academy of Sciences, pp. 257-258 (1994).
Lazar, E., et al., "Transforming Growth Factor α: Mutation of Aspartic Acid 47 and Leucine 48 Results in Different Biological Activities," Molecular and Cellular Biology, 8(3):1247-1252 (1988).
Lebrun, J.J., et al, "Activin and Inhibin Have Antagonistic Effects on Ligand-Dependent Heteromerization of the Type I and Type II Activin Receptors and Human Erythroid Differentiation," Molecular and Cellular Biology, 17(3):1682-1691 (1997).
Lee et al., "Regulation of Muscle Growth by Multiple Ligands Signaling Through Activin Type II Receptors," PNAS 102(50):18117-18122 (2005).
Lee, et al., "Regulation of Myostatin Activity and Muscle Growth," PNAS, 98(16):9306-9311 (2001).
Leto et al., "Activin A Circulating Levels in Patients with Bone Metastasis from Breast or Prostate Cancer," Clin Exp Metastasis, 23(2):117-122 (2006).
Li, Q., et al., "Prevention of cachexia-like syndrome development and reduction of tumor progression in inhibin-deficient mice following administration of a chimeric activin receptor type II-murine Fc protein," Molecular Human Reproduction, 13(9):675-683 (2007).

Ludlow, H., et al., "Development of a new antibody to the human inhibin/activin βB subunit and its application to improved inhibin B ELISAs," J. Immunol. Methods, 329:102-111 (2008).

Maguer-Satta, V., et al, "Regulation of human erythropoiesis by activin A, BMP2, and BMP4, members of the TGFβ family," Experimental Cell Research, 282:110-120 (2003).

Matzuk et al., "Different phenotypes for mice deficient in either activins or activin receptor type II," Nature, 374:356-360 (1995).

McNally, E.M., "Powerful Genes—Myostatin Regulation of Human Muscle Mass," N. Engl. J. Med., 350(26):2642-2644 (2004).

McPherron, A.C., et al., "Regulation of Skeletal Muscle Mass in Mice by a Bew TGF-b Superfamily Member," Nature, 387:83-90 (1997).

McPherson, S.J., et al., "Growth inhibitory response to activin A and B by human prostate tumour cell lines LNCaP and DU1465", Journal of Endocrinology, 154:535-545 (1997).

Meriggiola et al., "Follistatin Decreases Activin-Stimulated FSH Secretion with No Effect On GnRH-Stimulated FSH Secretion in Prepubertal Male Monkeys," Endocrinology, 134(4):1967-1970 (1994).

Murase et al., "Possible Involvement of Protein Kinases and Smad2 Signaling Pathways on Osteoclast Differentiation Enhanced by Activin A," Journal of Cellular Physiology, 188:236-242 (2001).

Nagamine et al., "Immunohistochemical Detection of Activin A, Follistatin, and Activin Receptors during Fracture Healing in the Rat," Journal of Orthopaedic Research, 16:314-321 (1998).

Nakamura, K., et al., "Effect of Erythroid Differentiation Factor on Maintenance of Human Hematopoietic Cells in Co-cultures with Allogenic Stromal Cells," Biochemical and Biophysical Research Communications, 194(3):1103-1110 (1993).

Ogawa et al., "Bovine Bone Activin Enhances Bone Morphogenetic Protein-Induced Ectopic Bone Formation," The Journal of Biological Chemistry, 267(20):14233-14237 (1992).

Oh, S.P., et al., "Activin type IIA and IIB receptors mediate Gdf11 signaling in axial vertebral patterning," Genes & Development, 16:2749-2754 (2002).

Oue et al., "Effect of Local Injection of Activin A on Bone Formation in Newborn Rats," Bone, 15(3):361-366 (1994).

Pearsall, et al., "A Soluble Activin Receptor Type IIA (ACTRIIA) Acts As a Novel Bone Anabolic Agent," The Official Journal of the European Calcified Tissue Society, 34th Europena Symposium on Calcified Tissues, May (2007).

Pearsall, et al., "Treatment with a Soluble Activin Type II Receptor Reverses Bone Loss in Ovariectomized Mice," Journal of Bone and Mineral Research 2006 Abstracts, 21(1):s1-s530 (2006).

Pearsall, R.S., et al., "A soluble activin Type IIA receptor induces bone formation and improves skeletal integrity", PNAS, 105(9):7082-7087 (2008).

Rebbapragada, et al., "Myostatin Signals Through a Transforming Growth Fact b-Like Signaling Pathway to Block Adipogenesis," Molecular and Cellular Biology, 23(20):7230-7242 (2003).

"Recombinant Human Activin RIIB/Fc Chimera," R&D Systems 339-RB/CF (2003).

"Recombinant Human Activin RIIA/Fc Chimera," R&D Systems 340-R2. (2003).

Reis, F.M., et al., "Activin, Inhibin and the Human Breast," Molecular and Cellular Edocrinology, 225:77-82 (2004).

Risbridger, G.P, et al., "Activins and Inhibins in Endocrine and Other Tumors," Endocrine Reviews, 22(6):836-858 (2001).

Robinson, G.W., et al., "Inhibins and Activins Regulate Mammary Epithelial Cell Differentiation Through Mesenchymal-epithelial Interactions," Development, 124:2701-2708 (1997).

Ruzek et al. Minimal Effects on Immune Parameters Following Chronic Anti-TGF-β Monoclonal Antibody Administration to Normal Mice. Immunopharmacology and Immunotoxicology vol. 25, No. 2 pp. 235-257 (2003).

Sakai et al., "Activin Enhances Osteoclast-Like Cell Formation in Vitro," Biochemical and Biophysical Research Communications, 195(1):39-46 (1993).

Sakai et al., "Activin Increases Bone Mass and Mechanical Strength of Lumbar Vertebrae in Aged Ovariectomized Rats," Bone, 27(1):91-96 (2000).

Sakai et al., "Activin release from bone coupled to bone resorption in organ culture of neonatal mouse calvaria," Bone, 26(3):235-240 (2000).

Sakai et al., "Involvement of Activin in the Regulation of Bone Metabolism," Molecular and Cellular Endocrinology, 180:183-188 (2001).

Sakai et al., "Local Administration of Activin Promotes Fracture Healing in the Rat Fibula Fracture Model," Bone, 25(2):191-196 (1999).

Sakai et al., The Measurement of Activin/EDF in Mouse Serum: Evidence for Extragonadal Production. Biochecmical and Biophysical Research Communications vol. 188, No. 2 pp. 921-926 (1992).

Sakai, et al., "Osteogenic Activity of Activin in Young Normal Rats and Young Adult and Aged Rats after Ovarlectomy," Bone, 23:(Suppl.) 467 (1998).

Schuelke, M., et al., "Myostatin Mutation Associated with Gross Muscle Hypertrophy in a Child," New England Journal of Medicine, 350(26):2682-2688 (2004).

Shao, L., et al., "Effect of Activin A on Globin Gene Expression in Purified Human Erythroid Progenitors," Blood, 79(3):773-781 (1992).

Shav-Tal, Y., et al., "The Role of Activin A in Regulation of Hemopoiesis," Stem Cells, 20:493-500 (2002).

Shiozaki, M., et al, "Activin A: A Commitment Factor in Erythroid Differentiation," Biochemical and Biophysical Research Communications, 242:631-635 (1998).

Shiozaki, M., et al, "Evidence for the participation of endogenous activin A/erythroid differentiation factor in the regulation of erythropoiesis," Proc. Natl. Acad. Sci. USA, 89:1553-1556 (1992).

Shiozaki, M., et al., "In Vivo Treatment With Erythroid Differentiation Factor (EDF / Activin A) Increases Erythroid Precursors (CFU-E and BFU-E) in Mice," Biochemical and Biophysical Research Communications, 165(3):1155-1161 (1989).

Shuto et al., "Osteoblasts Express Types I and II Activin Receptors During Early Intramembranous and Endochondral Bone Formation," Journal of Bone Mineral Research, 12(3):403-411 (1997).

Song, J., et al., "The Type II Activin Receptors Are Essential for Egg Cylinder Growth, Gastrulation, and Rostral Head Development in Mice," Development Biology, 213:157-169 (1999).

Springer, et al., "Seventh European Congress on Clinical and Economic Aspects of Osteoporosis and Osteoarthritis," Osteoporosis International, 18(1):S29-S75 (2007).

Sun, et al., "FSH Directly Regulates Bone Mass," Cell, 125:247-260 (2006).

Thompson, et al., "Structures of an ActRIIB: activin A complex reveal a novel binding mode for TGF-beta ligand: receptor interactions", EMBO 22(7):1555-1566 (2003).

Tsuchida, et al., "Activin isoforms signal through type I receptor serine/threonine kinase ALK7," Molecular and Cellular Endocrinology, vol. 220, pp. 59-65 (2004).

Weber, et al., A slient H-bond can by mutationally activated for high-affinity interaction of BMP-2 and activin type IIB receptor, BMC Structural Biology, 7:6, 1-20. (2007).

Wells, J.A., "Additivity of Mutational Effects in Proteins," Biochemistry, 29(37):8509-8517 (1990).

Welt, et al., "Activin: an endocrine or panacrine agent?," European Journal of Endocrinology 139:469-471 (1998).

Wiater, et al., "Inhibin is an Antagonist of Bone Morphogenetic Protein Signaling," The Journal of Biological Chemistry, 278(10):7934-7941 (2003).

Wolfman, N.M., et al., "Activation of latent myostatin by the BMP-1/tolloid family of metalloproteinases," PNAS, 100(26):15842-15846 (2003).

Yokota, T., et al., "Isolation and characterization of a mouse cDNA clone that expresses mast-cell growth-factor activity in monkey cells," Proc. Natl. Acad. Sci. USA, 81:1070-1074 (1984).

Yu et al., "Specific roles of activin/inhibin in human erythropoiesis in vitro," Annals New York Academy of Sciences, 20(10):1243-1246 (1991).

Yu, J., et al., "Importance of FSH-releasing protein and inhibin in erythrodifferentiation," Nature, 330:765-767 (1987).

Zhao, B., et al., "Transgenic expression of myostatin propeptide prevents diet-induced obesity and insulin resistance," Biochemical and Biophysical Research Communications, 337:248-255 (2005).

Allendorph, G.P., et al., "Structure of the ternary signaling complex of a TGF-β superfamily member," PNAS, 103(20):7643-7648 (2006).

Banks, G.B., et al., "The Value of Mammalian Models for Duchenne Muscular Dystrophy in Developing Therapeutic Strategies," Current Topics in Developmental Biology, 84:431-453 (2008).

Bodey, B., et al., "Failure of Cancer Vaccines: The Significant Limitations of this Approach to Immunotherapy," Anticancer Research, 20:2665-2676 (2000).

Bogdanovich, S., et al., "Functional improvement of dystrophic muscle by myostatin blockade," Nature, 420:418-421 (2002).

Chamberlain, R.S., et al., "Innovations and strategies for the development of anticancer vaccines," Expert Opinion on Pharmacotherapy, 1(4):603-614 (2000).

Cirillo, M., et al., "Hematocrit, Blood Pressure, and Hypertension. The Gubbio Population Study," Hypertension, 20(3):319-326 (1992).

Collins, C.D., "Problems Monitoring Response in Multiple Myeloma," Cancer Imaging 5:S119-S126 (2005).

Colman, P.M., et al., "Effects of amino acid sequence changes on antibody-antigen interactions," Research of Immunology, 145(1):33-36 (1994).

Deconinck, N., et al., "Pathophysiology of Duchenne Muscular Dystrophy: Current Hypotheses," Pediatr. Neurol., 36:1-7 (2007).

Gilbert, R., et al., "Prolonged dystrophin expression and functional correction of mdx mouse muscle following gene transfer with a helper-dependent (gutted) adenovirus-encoding murine dystrophin," Human Molecular Genetics, 12(11):1287-1299 (2003).

Greenspan, N.S., et al., "Defining epitopes: It's not as easy as it seems," Nature Biotechnology, 17:936-937 (1999).

Greenwald, J., et al., "Three-finger toxin fold for the extracellular ligand-binding domain of the type II activin receptor serine kinase," Nature Structural Biology, 6(1):18-22 (1999).

Gura, T., "Cancer Models: Systems for Identifying New Drugs Are Often Faulty," Science, 278(5340):1041-1042 (1997).

Herbert, W.J., et al., The Dictionary of Immunology, Academic Press, 3rd Edition, London, pp. 58-59 (1985).

Kaiser, J., "First Pass at Cancer Genome Reveals Complex Landscape," Science, 313:1370 (2006).

Kim, K.T., et al., "Type IIa IgG-Fc Fusion Protein, Increases Hemoglobin and Hematocrit Levels in Postmenopausal Healthy Women," Blood, 112(11):1316 (2008).

Krag, T.O.B., et al., "Heregulin ameliorates the dystrophic phenotype in mdx mice," PNAS, 101(38):13856-13860 (2004).

Kunihro, T., et al., "Regulation of Muscle Mass and Hepatic Steatosis by Follistatin-derived Myostatin Inhibitors," Making Muscle in the Embryo and Adult: a joint meeting of Frontiers in Myogenesis and Skeletal Muscle Stem and Satellite Cells, New York, NY, p. 45 (Abstract) (1990).

Merck Manuals Online Medical Library (online). Anemia of Chronic Disease, Jun. 10, 2008. Downloaded from the internet on Jan. 5, 2010. <http://web.archive.org/web/20080610070226/http://www.merck.com/mmpe/sec11/ch130/ch130d.html> pp. 1-2.

Merck Manuals Online Medical Library (online). Iron Deficiency Anemia, Jun. 10, 2008. Downloaded from the internet on Jan. 5, 2010. <http://web.archive.org/web/20080610070221/http://www.merck.com/mmpe/sec11/ch130/ch130d.html> pp. 1-4.

Mickle, J.E., et al., "Genotype-Phenotype Relationships in Cystic Fibrosis," Med. Clin. North Am., 84(3):597-607 (2000).

Miura, P., et al., "Utrophin upregulation for treating Duchenne or Becker muscular dystrophy: how close are we?," Trends in Molecular Medicine, 12(3):122-129 (2006).

Ngo, J.T., et al., "Computational Complexity, Protein Structure Prediction, and the Levinthal Paradox," The Protein Folding Problem and Tertiary Structure Prediction, Merz et al., eds., Birkhauser, Boston, 492-495 (1994).

Patel, K., et al., "The function of Myostatin and strategies of Myostatin blockade—new hope for therapies aimed at promoting growth of skeletal muscle," Neuromuscular Disorders, 15:117-126 (2005).

Qi, Z., et al., "Blockade of type β transforming growth factor signaling prevents liver fibrosis and dysfunction in the rat," PNAS, 96:2345-2349 (1999).

Rodriquez, J.E.S., et al., "Enhanced Osteoclastogenesis Causes Osteopenia in Twisted Gastrulation-Deficient Mice Through Increased BMP Signaling," J. Bone Miner. Res., 24:1917-1926 (2009).

Satoh, K., et al., "Hemodynamic changes by recombinant erythropoietin therapy in hemodialyzed patients," Hypertension, 15(3):262-266 (1990).

Tinsley, J., et al., "Expression of full-length utrophin prevents muscular dystrophy in mdx mice," Nature Medicine, 4(12):1441-1444 (1998).

Tu, P., et al., "Genetic Disruption of Myostatin Reduces the Development of Proatherogenic Dyslipidemia and Atherogenic Lesions in Ldlr Null Mice," Diabetes, 58:1739-1748 (2009).

Vallet, S., et al., "Activin A promotes multiple myeloma-induced osteolysis and is a promising target for myeloma bone disease," PNAS, 107(11):5124-5129 (2010).

Wagner, K.R., et al., "A Phase I/II trial of MYO-029 in Adult Subjects with Muscular Dystrophy," Ann. Neurol., 63:561-571 (2008).

Wagner, K.R., et al., "Loss of Myostatin Attenuates Severity of Muscular Dystrophy in mdx Mice," Ann. Neurol., 52:832-836 (2002).

Wagner, K.R., et al., "Muscle regeneration in the prolonged absence of myostatin," PNAS, 102(7):2519-2524 (2005).

* cited by examiner

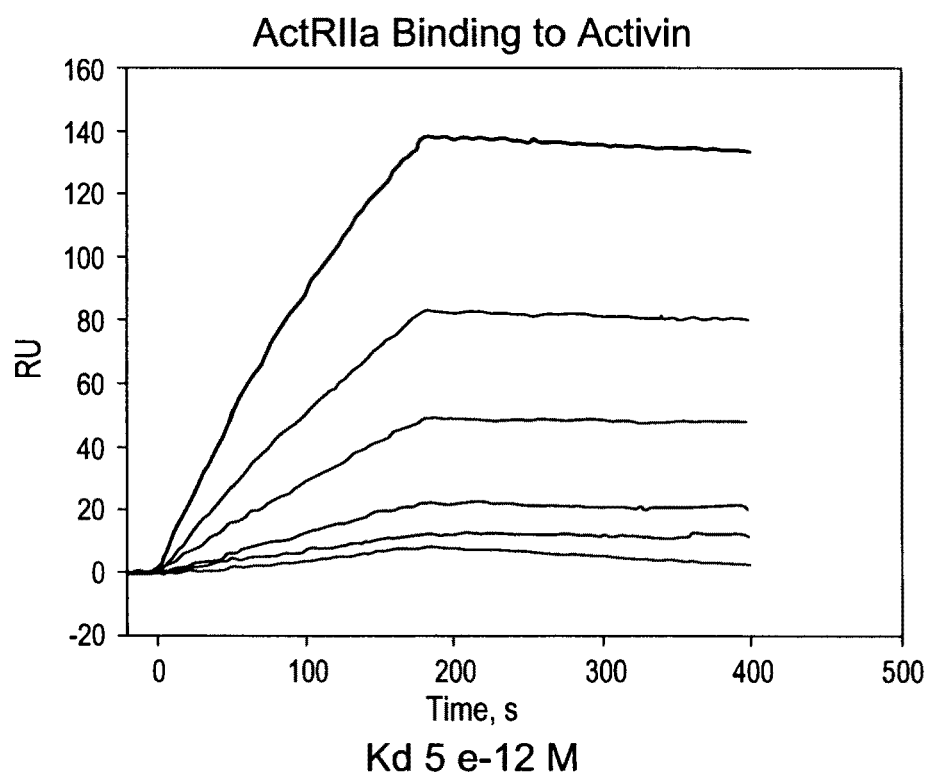
Kd 5 e-12 M
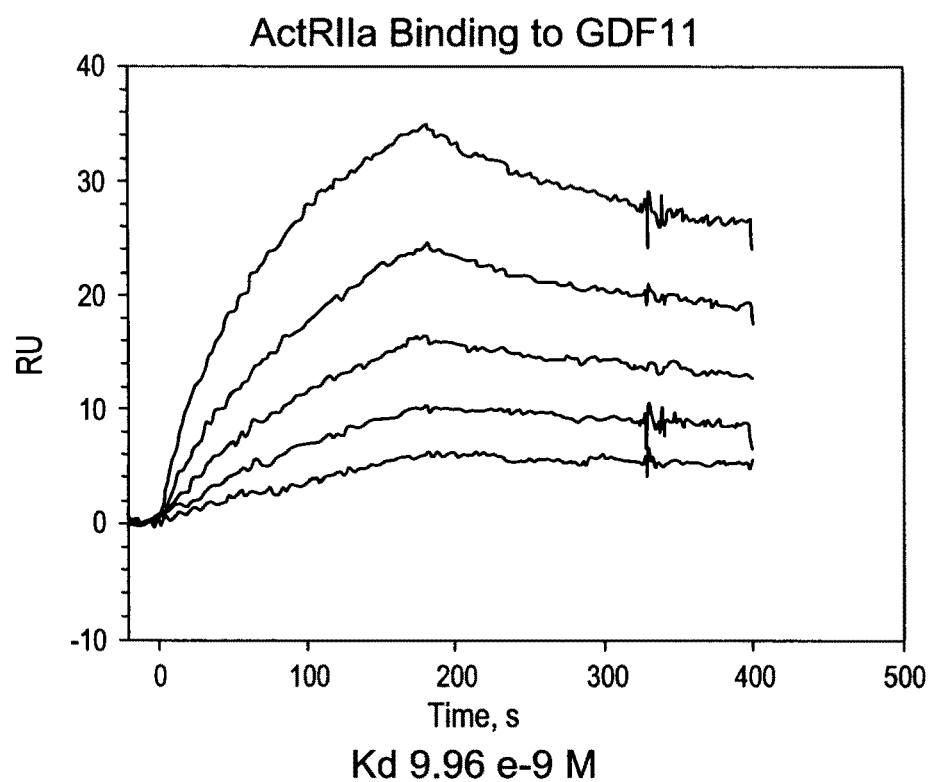
Kd 9.96 e-9 M
Figure 2

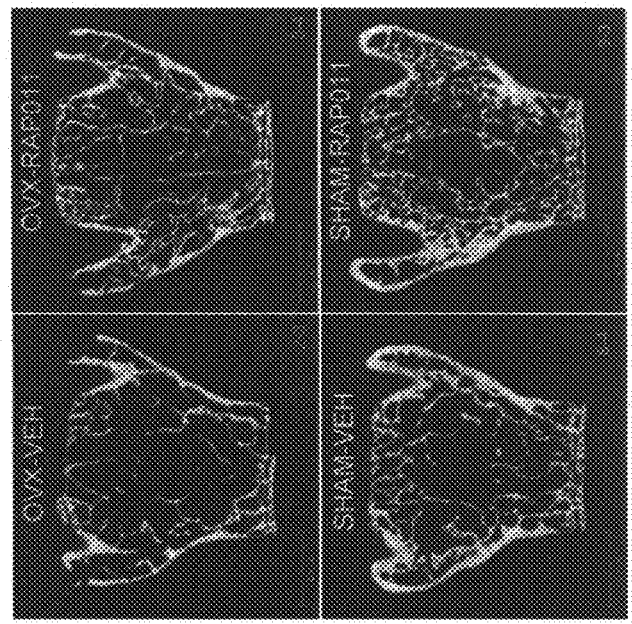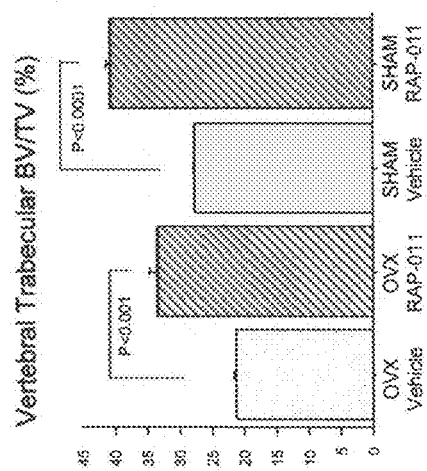
Figure 19

| @ 12 weeks | OVX-VEH | OVX-RAP-011 | SHAM-VEH | SHAM-RAP-011 |
|---|---|---|---|---|
| Tb N (mm$^{-1}$) | 2.1 ± 0.3 | 3.5 ± 0.2 ** | 3.0 ± 0.2 | 4.1 ± 0.2 ** |
| Tb Sp (µm) | 486.2 ± 79 | 283.9 ± 21 ** | 332.4 ± 25 | 230.2 ± 12 ** |
| Conn D (mm$^{-3}$) | 8.4 ± 6 | 85.1 ± 13.7 ** | 41.4 ± 14.8 | 131.2 ± 16.5 ** |

** $p < 0.01$ vs VEH

Figure 20

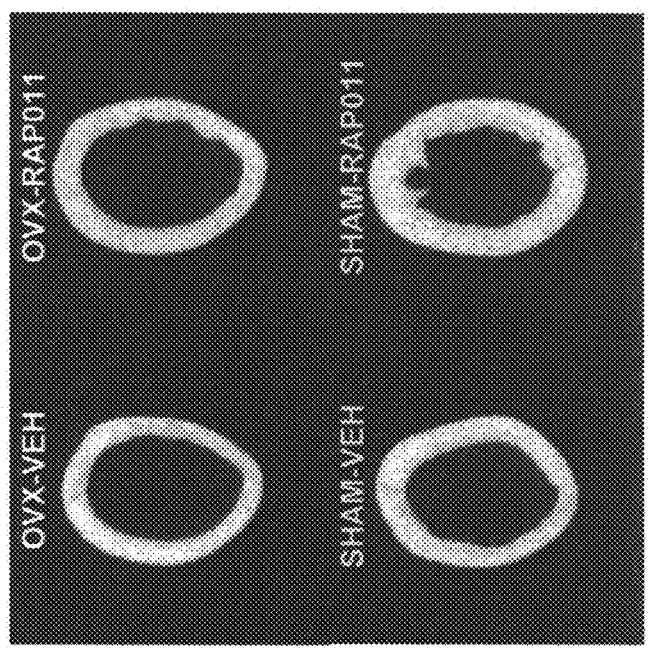
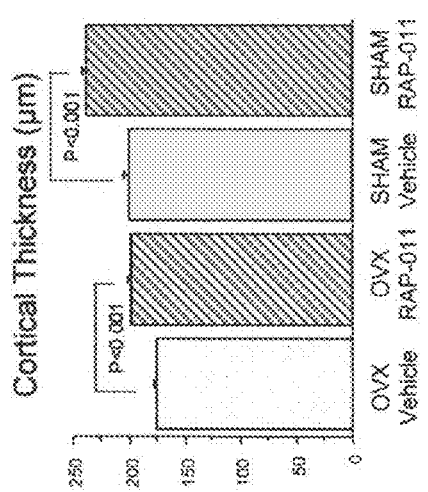
Figure 21

| | BV/TV (%) | ES/BS (%) | Nob/BPm (/mm) | Noc/BPm (/mm) | Ms/Bs (%) | MAR (um/day) | BFR/BSd (um$^3$/um$^2$/day) |
|---|---|---|---|---|---|---|---|
| PBS mean | 7.53 | 17.36 | 49.33 | 7.55 | 4.206 | 0.704 | 0.029 |
| RAP-011 mean | 10.88 | 13.93 | 40.89 | 5.34 | 7.546 | 0.852 | 0.065 |
| P value | 0.002 | 0.03 | 0.02 | 0.01 | 0.008 | 0.03 | 0.002 |

Figure 24

| PARAMETER | 2 WEEK VEH (N=6) | 2 WEEK RAP-011 (N=6) | 4 WEEK VEH (N=6) | 4 WEEK RAP-011 (N=6) | 8 WEEK VEH (N=6) | 8 WEEK RAP-011 (N=6) | 12 WEEK VEH (N=6) | 12 WEEK RAP-011 (N=6) |
|---|---|---|---|---|---|---|---|---|
| BONE VOLUME (BV/TV), % | 7.53 ± 0.35 | 10.88 ± 0.45* | 7.04 ± 0.51 | 15.57 ± 1.39* | 6.14 ± 0.41 | 14.31 ± 0.53* | 4.39 ± 0.42 | 15.24 ± 1.08* |
| OSTEOID SURFACE (OS/BS), % | 4.86 ± 0.34 | 5.32 ± 0.49 | 3.95 ± 0.51 | 3.65 ± 0.36 | 3.26 ± 0.34 | 3.31 ± 0.42 | 2.1 ± 0.46 | 1.91 ± 0.08 |
| ERODED SURFACE (ES/BS), % | 17.36 ± 0.99 | 13.93 ± 0.96* | 13.61 ± 1.6 | 12.01 ± 1.39 | 12.38 ± 1.31 | 11.89 ± 0.77 | 8.56 ± 0.77 | 10.0 ± 0.34 |
| NUMBER OF OSTEOBLASTS/AREA (Ob./Tar), no./mm | 429.9 ± 25.33 | 455.3 ± 28.29 | 411.8 ± 44.61 | 567.8 ± 53.13* | 405.2 ± 24.2 | 634.6 ± 35.39* | 238.7 ± 14.2 | 521.9 ± 22.77* |
| OSTEOBLAST SURFACE/BONE SURFACE (Obs/BS), % | 36.12 ± 2.42 | 29.43 ± 1.52* | 33.5 ± 2.53 | 29.14 ± 1.93 | 35.5 ± 1.27 | 35.92 ± 1.29 | 28.45 ± 1.32 | 30.24 ± 1.5 |
| OSTEOBLAST SURFACE ON BONE PERIMETER (Nob/BPm), % | 49.33 ± 2.52 | 40.89 ± 1.46* | 48.52 ± 4.16 | 41.33 ± 3.25 | 49.61 ± 2.87 | 49.2 ± 3.26 | 39.4 ± 2.03 | 36.64 ± 2.53 |
| NUMBER OF OSTEOCLASTS/AREA (Oc./Tar), no./mm | 65.81 ± 4.97 | 59.62 ± 5.89 | 51.42 ± 3.58 | 65.68 ± 8.18 | 45.23 ± 3.98 | 62.95 ± 5.18* | 28.07 ± 1.85 | 61.15 ± 1.87* |
| OSTEOCLAST SURFACE/BONE SURFACE (Obc/BS), % | 7.55 ± 0.53 | 5.34 ± 0.45* | 6.25 ± 0.66 | 4.78 ± 0.59 | 5.74 ± 0.58 | 4.86 ± 0.4 | 4.65 ± 0.32 | 4.49 ± 0.17 |
| OSTEOCLAST ON BONE PERIMETER (Noc/BPm), % | 8.78 ± 0.78 | 6.23 ± 0.5* | 6.86 ± 0.67 | 5.36 ± 0.62 | 6.38 ± 0.67 | 5.8 ± 0.46 | 8.56 ± 0.77 | 10.0 ± 0.34 |
| TRABECULAR THICKNESS (TbTh), -m | 13.59 ± 0.48 | 15.42 ± 0.45* | 13.11 ± 0.46 | 17.68 ± 0.75* | 12.04 ± 0.5 | 17.28 ± 0.35* | 11.18 ± 0.52 | 17.49 ± 1.02* |
| TRABECULAR SEPERATION (TbSp), -m | 167.7 ± 5.88 | 127.6 ± 7.25* | 176 ± 9.3 | 98.61 ± 6.95* | 187 ± 7.13 | 104.3 ± 3.42* | 251.8 ± 18.14 | 98.07 ± 4.27* |
| TRABECULAR NUMBER (TbN), no./mm | 5.55 ± 0.19 | 7.09 ± 0.36* | 5.34 ± 0.23 | 8.73 ± 0.5* | 5.07 ± 0.18 | 8.27 ± 0.22* | 3.89 ± 0.27 | 8.7 ± 0.29* |
| MINERALIZING SURFACE (MS/BS), % | 4.21 ± 0.7 | 7.55 ± 0.73* | 4.15 ± 1.02 | 8.84 ± 0.77* | 3.6 ± 0.56 | 7.97 ± 0.73* | 3.86 ± 0.4 | 6.66 ± 0.51* |
| MINERAL APPOSITION RATE (mm/day) | 0.704 ± 0.049 | 0.852 ± 0.028* | 0.566 ± 0.042 | 0.642 ± 0.014 | 0.517 ± 0.02 | 0.602 ± 0.016* | 0.425 ± 0.009 | 0.533 ± 0.013* |
| BONE FORMATION RATE (-m3/um2/day) | 0.029 ± 0.004 | 0.065 ± 0.008* | 0.025 ± 0.008 | 0.057 ± 0.005* | 0.019 ± 0.003 | 0.048 ± 0.004* | 0.016 ± 0.002 | 0.035 ± 0.002* |

Figure 25

SEQUENCE LISTING

<160> NUMBER OF SEQ ID NOS: 18

<210> SEQ ID NO 1
<211> LENGTH: 513
<212> TYPE: PRT
<213> ORGANISM: Homo sapiens

<400> SEQUENCE: 1

Met Gly Ala Ala Ala Lys Leu Ala Phe Ala Val Phe Leu Ile Ser Cys
1               5                   10                  15

Ser Ser Gly Ala Ile Leu Gly Arg Ser Glu Thr Gln Glu Cys Leu Phe
                20                  25                  30

Phe Asn Ala Asn Trp Glu Lys Asp Arg Thr Asn Gln Thr Gly Val Glu
            35                  40                  45

Pro Cys Tyr Gly Asp Lys Asp Lys Arg Arg His Cys Phe Ala Thr Trp
    50                  55                  60

Lys Asn Ile Ser Gly Ser Ile Glu Ile Val Lys Gln Gly Cys Trp Leu
65                  70                  75                  80

Asp Asp Ile Asn Cys Tyr Asp Arg Thr Asp Cys Val Glu Lys Lys Asp
                85                  90                  95

Ser Pro Glu Val Tyr Phe Cys Cys Cys Glu Gly Asn Met Cys Asn Glu
            100                 105                 110

Lys Phe Ser Tyr Phe Pro Glu Met Glu Val Thr Gln Pro Thr Ser Asn
        115                 120                 125

Pro Val Thr Pro Lys Pro Pro Tyr Tyr Asn Ile Leu Leu Tyr Ser Leu
    130                 135                 140

Val Pro Leu Met Leu Ile Ala Gly Ile Val Ile Cys Ala Phe Trp Val
145                 150                 155                 160

Tyr Arg His His Lys Met Ala Tyr Pro Pro Val Leu Val Pro Thr Gln
                165                 170                 175

```
Asp Pro Gly Pro Pro Pro Ser Pro Leu Leu Gly Leu Lys Pro Leu
            180                 185                 190

Gln Leu Leu Glu Val Lys Ala Arg Gly Arg Phe Gly Cys Val Trp Lys
        195                 200                 205

Ala Gln Leu Leu Asn Glu Tyr Val Ala Val Lys Ile Phe Pro Ile Gln
    210                 215                 220

Asp Lys Gln Ser Trp Gln Asn Glu Tyr Glu Val Tyr Ser Leu Pro Gly
225                 230                 235                 240

Met Lys His Glu Asn Ile Leu Gln Phe Ile Gly Ala Glu Lys Arg Gly
                245                 250                 255

Thr Ser Val Asp Val Asp Leu Trp Leu Ile Thr Ala Phe His Glu Lys
            260                 265                 270

Gly Ser Leu Ser Asp Phe Leu Lys Ala Asn Val Val Ser Trp Asn Glu
        275                 280                 285

Leu Cys His Ile Ala Glu Thr Met Ala Arg Gly Leu Ala Tyr Leu His
    290                 295                 300

Glu Asp Ile Pro Gly Leu Lys Asp Gly His Lys Pro Ala Ile Ser His
305                 310                 315                 320

Arg Asp Ile Lys Ser Lys Asn Val Leu Leu Lys Asn Asn Leu Thr Ala
                325                 330                 335

Cys Ile Ala Asp Phe Gly Leu Ala Leu Lys Phe Glu Ala Gly Lys Ser
            340                 345                 350

Ala Gly Asp Thr His Gly Gln Val Gly Thr Arg Arg Tyr Met Ala Pro
        355                 360                 365

Glu Val Leu Glu Gly Ala Ile Asn Phe Gln Arg Asp Ala Phe Leu Arg
    370                 375                 380

Ile Asp Met Tyr Ala Met Gly Leu Val Leu Trp Glu Leu Ala Ser Arg
385                 390                 395                 400

Cys Thr Ala Ala Asp Gly Pro Val Asp Glu Tyr Met Leu Pro Phe Glu
                405                 410                 415

Glu Glu Ile Gly Gln His Pro Ser Leu Glu Asp Met Gln Glu Val Val
            420                 425                 430

Val His Lys Lys Lys Arg Pro Val Leu Arg Asp Tyr Trp Gln Lys His
        435                 440                 445

Ala Gly Met Ala Met Leu Cys Glu Thr Ile Glu Glu Cys Trp Asp His
    450                 455                 460

Asp Ala Glu Ala Arg Leu Ser Ala Gly Cys Val Gly Glu Arg Ile Thr
465                 470                 475                 480

Gln Met Gln Arg Leu Thr Asn Ile Ile Thr Thr Glu Asp Ile Val Thr
                485                 490                 495

Val Val Thr Met Val Thr Asn Val Asp Phe Pro Pro Lys Glu Ser Ser
            500                 505                 510

Leu

<210> SEQ ID NO 2
<211> LENGTH: 115
<212> TYPE: PRT
<213> ORGANISM: Homo sapiens

<400> SEQUENCE: 2

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30
```

```
Asp Lys Asp Lys Arg Arg His Cys Phe Ala Thr Trp Lys Asn Ile Ser
            35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
                100                 105                 110

Lys Pro Pro
        115

<210> SEQ ID NO 3
<211> LENGTH: 100
<212> TYPE: PRT
<213> ORGANISM: Homo sapiens

<400> SEQUENCE: 3

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
            35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met
                100

<210> SEQ ID NO 4
<211> LENGTH: 1542
<212> TYPE: DNA
<213> ORGANISM: Homo sapiens

<400> SEQUENCE: 4
atgggagctg ctgcaaagtt ggcgtttgcc gtctttctta tctcctgttc ttcaggtgct      60
atacttggta gatcagaaac tcaggagtgt cttttcttta tgctaattg gaaaaagac      120 agaaccaatc aaactggtgt tgaaccgtgt tatggtgaca agataaacg gcggcattgt      180 tttgctacct ggaagaatat ttctggttcc attgaaatag tgaaacaagg ttgttggctg      240
gatgatatca actgctatga caggactgat tgtgtagaaa aaaagacag ccctgaagta      300 tattttgtt gctgtgaggg caatatgtgt aatgaaaagt tttcttattt tccagagatg      360
gaagtcacac agcccacttc aaatccagtt acacctaagc cacccctatta caacatcctg      420 ctctattcct tggtgccact tatgttaatt gcggggattg tcatttgtgc attttgggtg      480
tacaggcatc acaagatggc ctaccctcct gtacttgttc aactcaaga cccaggacca      540 cccccacctt ctccattact agggttgaaa ccactgcagt tattagaagt gaaagcaagg      600
ggaagatttg gttgtgtctg gaaagcccag ttgcttaacg aatatgtggc tgtcaaaata      660
tttccaatac aggacaaaca gtcatggcaa atgaatacg aagtctacag tttgcctgga      720
atgaagcatg agaacatatt acagttcatt ggtgcagaaa aacgaggcac cagtgttgat      780
```

```
gtggatcttt ggctgatcac agcatttcat gaaaagggtt cactatcaga ctttcttaag    840
gctaatgtgg tctcttggaa tgaactgtgt catattgcag aaaccatggc tagaggattg    900
gcatatttac atgaggatat acctggccta aaagatggcc acaaacctgc catatctcac    960
agggacatca aaagtaaaaa tgtgctgttg aaaaacaacc tgacagcttg cattgctgac   1020
tttgggttgg ccttaaaatt tgaggctggc aagtctgcag gcgatacccc atggacaggtt  1080 ggtacccgga ggtacatggc tccagaggta ttagagggtg ctataaactt ccaaagggat   1140
gcatttttga ggatagatat gtatgccatg ggattagtcc tatgggaact ggcttctcgc   1200
tgtactgctg cagatggacc tgtagatgaa tacatgttgc catttgagga ggaaattggc   1260
cagcatccat ctcttgaaga catgcaggaa gttgttgtgc ataaaaaaaa gaggcctgtt   1320
ttaagagatt attggcagaa acatgctgga atggcaatgc tctgtgaaac cattgaagaa   1380
tgttgggatc acgacgcaga agccaggtta tcagctggat gtgtaggtga aagaattacc   1440
cagatgcaga gactaacaaa tattattacc acagaggaca ttgtaacagt ggtcacaatg   1500
gtgacaaatg ttgactttcc tcccaaagaa tctagtctat ga                      1542

<210> SEQ ID NO 5
<211> LENGTH: 345
<212> TYPE: DNA
<213> ORGANISM: Homo sapiens

<400> SEQUENCE: 5
atacttggta gatcagaaac tcaggagtgt cttttcttta atgctaattg ggaaaaagac     60
agaaccaatc aaactggtgt tgaaccgtgt tatggtgaca agataaacg gcggcattgt    120 tttgctacct ggaagaatat ttctggttcc attgaaatag tgaaacaagg ttgttggctg    180
gatgatatca actgctatga caggactgat tgtgtagaaa aaaagacag ccctgaagta    240 tatttttgtt gctgtgaggg caatatgtgt aatgaaaagt tttcttattt tccagagatg    300
gaagtcacac agcccacttc aaatccagtt acacctaagc caccc                    345

<210> SEQ ID NO 6
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (43)..(43)
<223> OTHER INFORMATION: Asp or Ala
<220> FEATURE:
<221> NAME/KEY: MOD_RES
<222> LOCATION: (100)..(100)
<223> OTHER INFORMATION: Lys or Ala
<220> FEATURE:
<221> NAME/KEY: MOD_RES
<222> LOCATION: (212)..(212)
<223> OTHER INFORMATION: Asn or Ala

<400> SEQUENCE: 6

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Xaa Val Ser His Glu Asp
        35                  40                  45

Pro Glu Val Lys Phe Asn Trp Tyr Val Asp Gly Val Glu Val His Asn
```

```
                    50                  55                  60
Ala Lys Thr Lys Pro Arg Glu Glu Gln Tyr Asn Ser Thr Tyr Arg Val
 65                  70                  75                  80

Val Ser Val Leu Thr Val Leu His Gln Asp Trp Leu Asn Gly Lys Glu
                     85                  90                  95

Tyr Lys Cys Xaa Val Ser Asn Lys Ala Leu Pro Val Pro Ile Glu Lys
                100                 105                 110

Thr Ile Ser Lys Ala Lys Gly Gln Pro Arg Glu Pro Gln Val Tyr Thr
            115                 120                 125

Leu Pro Pro Ser Arg Glu Glu Met Thr Lys Asn Gln Val Ser Leu Thr
130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Pro Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Xaa His Tyr Thr Gln Lys Ser Leu Ser Leu Ser Pro Gly
    210                 215                 220

Lys
225

<210> SEQ ID NO 7
<211> LENGTH: 344
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 7

Ile Leu Gly Arg Ser Glu Thr Gln Glu Cys Leu Phe Phe Asn Ala Asn
 1               5                  10                  15

Trp Glu Lys Asp Arg Thr Asn Gln Thr Gly Val Glu Pro Cys Tyr Gly
                20                  25                  30

Asp Lys Asp Lys Arg Arg His Cys Phe Ala Thr Trp Lys Asn Ile Ser
            35                  40                  45

Gly Ser Ile Glu Ile Val Lys Gln Gly Cys Trp Leu Asp Asp Ile Asn
        50                  55                  60

Cys Tyr Asp Arg Thr Asp Cys Val Glu Lys Lys Asp Ser Pro Glu Val
 65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
                100                 105                 110

Lys Pro Pro Thr Gly Gly Gly Thr His Thr Cys Pro Pro Cys Pro Ala
            115                 120                 125

Pro Glu Leu Leu Gly Gly Pro Ser Val Phe Leu Phe Pro Pro Lys Pro
130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
```

```
                    180                 185                 190
Tyr Asn Ser Thr Tyr Arg Val Val Ser Val Leu Thr Val Leu His Gln
            195                 200                 205

Asp Trp Leu Asn Gly Lys Glu Tyr Lys Cys Lys Val Ser Asn Lys Ala
        210                 215                 220

Leu Pro Val Pro Ile Glu Lys Thr Ile Ser Lys Ala Lys Gly Gln Pro
225                 230                 235                 240

Arg Glu Pro Gln Val Tyr Thr Leu Pro Pro Ser Arg Glu Glu Met Thr
                245                 250                 255

Lys Asn Gln Val Ser Leu Thr Cys Leu Val Lys Gly Phe Tyr Pro Ser
            260                 265                 270

Asp Ile Ala Val Glu Trp Glu Ser Asn Gly Gln Pro Glu Asn Asn Tyr
        275                 280                 285

Lys Thr Thr Pro Pro Val Leu Asp Ser Asp Gly Ser Phe Phe Leu Tyr
290                 295                 300

Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Pro Gly Lys
            340

<210> SEQ ID NO 8
<211> LENGTH: 21
<212> TYPE: PRT
<213> ORGANISM: Apis mellifera

<400> SEQUENCE: 8

Met Lys Phe Leu Val Asn Val Ala Leu Val Phe Met Val Val Tyr Ile
1               5                   10                  15

Ser Tyr Ile Tyr Ala
            20

<210> SEQ ID NO 9
<211> LENGTH: 22
<212> TYPE: PRT
<213> ORGANISM: Unknown
<220> FEATURE:
<223> OTHER INFORMATION: Description of Unknown: Tissue Plasminogen
      Activator peptide

<400> SEQUENCE: 9

Met Asp Ala Met Lys Arg Gly Leu Cys Cys Val Leu Leu Leu Cys Gly
1               5                   10                  15

Ala Val Phe Val Ser Pro
            20

<210> SEQ ID NO 10
<211> LENGTH: 20
<212> TYPE: PRT
<213> ORGANISM: Unknown
<220> FEATURE:
<223> OTHER INFORMATION: Description of Unknown: Native peptide

<400> SEQUENCE: 10

Met Gly Ala Ala Ala Lys Leu Ala Phe Ala Val Phe Leu Ile Ser Cys
1               5                   10                  15

Ser Ser Gly Ala
            20
```

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

Ile Leu Gly Arg Ser Glu Thr Gln Glu
1               5

<210> SEQ ID NO 12
<211> LENGTH: 329
<212> TYPE: PRT
<213> ORGANISM: Artificial Sequence
<220> FEATURE:
<223> OTHER INFORMATION: Description of Artificial Sequence: Synthetic construct

<400> SEQUENCE: 12

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Thr Gly Gly Gly Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Val Pro Ile Glu Lys Thr Ile Ser Lys Ala Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

```
Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 13
<211> LENGTH: 369
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 13

Met Asp Ala Met Lys Arg Gly Leu Cys Cys Val Leu Leu Leu Cys Gly
1               5                   10                  15

Ala Val Phe Val Ser Pro Gly Ala Ala Ile Leu Gly Arg Ser Glu Thr
                20                  25                  30

Gln Glu Cys Leu Phe Phe Asn Ala Asn Trp Glu Lys Asp Arg Thr Asn
            35                  40                  45

Gln Thr Gly Val Glu Pro Cys Tyr Gly Asp Lys Asp Lys Arg Arg His
        50                  55                  60

Cys Phe Ala Thr Trp Lys Asn Ile Ser Gly Ser Ile Glu Ile Val Lys
65                  70                  75                  80

Gln Gly Cys Trp Leu Asp Asp Ile Asn Cys Tyr Asp Arg Thr Asp Cys
                85                  90                  95

Val Glu Lys Lys Asp Ser Pro Glu Val Tyr Phe Cys Cys Cys Glu Gly
            100                 105                 110

Asn Met Cys Asn Glu Lys Phe Ser Tyr Phe Pro Glu Met Glu Val Thr
        115                 120                 125

Gln Pro Thr Ser Asn Pro Val Thr Pro Lys Pro Pro Thr Gly Gly Gly
130                 135                 140

Thr His Thr Cys Pro Pro Cys Pro Ala Pro Glu Leu Leu Gly Gly Pro
145                 150                 155                 160

Ser Val Phe Leu Phe Pro Pro Lys Pro Lys Asp Thr Leu Met Ile Ser
                165                 170                 175

Arg Thr Pro Glu Val Thr Cys Val Val Val Asp Val Ser His Glu Asp
            180                 185                 190

Pro Glu Val Lys Phe Asn Trp Tyr Val Asp Gly Val Glu Val His Asn
        195                 200                 205

Ala Lys Thr Lys Pro Arg Glu Glu Gln Tyr Asn Ser Thr Tyr Arg Val
    210                 215                 220

Val Ser Val Leu Thr Val Leu His Gln Asp Trp Leu Asn Gly Lys Glu
225                 230                 235                 240

Tyr Lys Cys Lys Val Ser Asn Lys Ala Leu Pro Val Pro Ile Glu Lys
                245                 250                 255

Thr Ile Ser Lys Ala Lys Gly Gln Pro Arg Glu Pro Gln Val Tyr Thr
            260                 265                 270

Leu Pro Pro Ser Arg Glu Glu Met Thr Lys Asn Gln Val Ser Leu Thr
        275                 280                 285

Cys Leu Val Lys Gly Phe Tyr Pro Ser Asp Ile Ala Val Glu Trp Glu
    290                 295                 300

Ser Asn Gly Gln Pro Glu Asn Asn Tyr Lys Thr Thr Pro Pro Val Leu
305                 310                 315                 320

Asp Ser Asp Gly Ser Phe Phe Leu Tyr Ser Lys Leu Thr Val Asp Lys
                325                 330                 335
```

Ser Arg Trp Gln Gln Gly Asn Val Phe Ser Cys Ser Val Met His Glu
            340                 345                 350

Ala Leu His Asn His Tyr Thr Gln Lys Ser Leu Ser Leu Ser Pro Gly
            355                 360                 365

Lys

<210> SEQ ID NO 14
<211> LENGTH: 1114
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 14
atggatgcaa tgaagagagg gctctgctgt gtgctgctgc tgtgtggagc agtcttcgtt      60
tcgcccggcg ccgctatact tggtagatca gaaactcagg agtgtctttt tttaatgcta     120
attgggaaaa agacagaacc aatcaaactg gtgttgaacc gtgttatggt gacaaagata     180
aacggcggca ttgttttgct acctggaaga atatttctgg ttccattgaa tagtgaaaca     240
aggttgttgg ctggatgata tcaactgcta tgacaggact gattgtgtag aaaaaaaaga     300
cagccctgaa gtatatttct gttgctgtga gggcaatatg tgtaatgaaa agttttctta     360
ttttccggag atggaagtca cacagcccac ttcaaatcca gttacaccta gccacccac      420 cggtggtgga actcacacat gcccaccgtg cccagcacct gaactcctgg ggggaccgtc     480
agtcttcctc ttccccccaa aacccaagga caccctcatg atctcccgga cccctgaggt     540
cacatgcgtg gtggtggacg tgagccacga agaccctgag gtcaagttca actggtacgt     600
ggacggcgtg gaggtgcata atgccaagac aaagccgcgg gaggagcagt acaacagcac     660
gtaccgtgtg gtcagcgtcc tcaccgtcct gcaccaggac tggctgaatg caaggagta     720 caagtgcaag gtctccaaca aagccctccc agtcccatc gagaaaacca tctccaaagc     780
caaagggcag ccccgagaac cacaggtgta caccctgccc ccatcccggg aggagatgac     840
caagaaccag gtcagcctga cctgcctggt caaaggcttc tatcccagcg acatcgccgt     900
ggagtgggag agcaatgggc agccggagaa caactacaag accacgcctc ccgtgctgga     960
ctccgacggc tccttcttcc tctatagcaa gctcaccgtg gacaagagca ggtggcagca    1020
ggggaacgtc ttctcatgct ccgtgatgca tgaggctctg cacaaccact acacgcagaa    1080
gagcctctcc ctgtctccgg gtaaatgaga attc                                1114

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Thr Gly Gly Gly Gly
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 16

Ser Gly Gly Gly Gly
1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 17

His His His His His His
1               5

<210> SEQ ID NO 18
<211> LENGTH: 108
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
agccagacaa gccagacaag ccagacaagc cagacaagcc agacaagcca gacaagccag       60
acaagccaga caagccagac aagccagaca agccagacaa gccagaca                   108
```

ACTIVIN-ACTRIIA ANTAGONISTS AND USES FOR DECREASING OR INHIBITING FSH SECRETION

CROSS-REFERENCE TO RELATED APPLICATIONS

This application claims the benefit of U.S. Provisional Application Ser. No. 60/994,399, filed Sep. 18, 2007. All the teachings of the above-referenced application are incorporated herein by reference.

SEQUENCE LISTING

The instant application contains a Sequence Listing which has been submitted via EFS-Web and is hereby incorporated by reference in its entirety. Said ASCII copy, created on Apr. 6, 2010, is named PHPH028SS.txt, and is 24,621 bytes in size.

BACKGROUND OF THE INVENTION

Follicle-stimulating hormone (FSH) is released by the pituitary gland and regulates the functioning of the gonads and the production and maturation of gametes. FSH is generally released by the pituitary gland upon prior release of a triggering hormone, such as gonadotropin-releasing hormone.

FSH release is necessary for ovulation in females and for maturation of sperm in males. In females, FSH stimulates follicular granulosa cell proliferation in the ovary and impacts synthesis of estrogen, a hormone which is integral to follicular maturation and ovulation. In males, FSH is involved in the maturation of sperm cells. More specifically, FSH action in males is directed at the Sertoli cells, which are a recognized target of the hormone and which support the process of sperm maturation (spermatogenesis). FSH is also produced in the prostate, where it is an important mediator of cell growth.

Accordingly, inhibitors of FSH release are useful as contraceptive agents in both males and females.

In addition to the function in fertility, FSH also plays a role in several disease states. Increased levels of FSH receptor are associated with prostate cancer, with the highest levels associated with hormone-refractory prostate cancer. Prostate cancer is the most common cancer in American men, with more than 230,000 new cases diagnosed each year. Approximately 30,000 deaths will be attributed to prostate cancer in 2004 (Jemal A, Tiwari R C, Murray T. Ghafoor A, Samuels A, Ward E, Feuer E J, Thun M J. Cancer statistics 2004. CA Cancer J. Clin. 54:8-29, 2004). Approximately 40% of individuals treated with surgery or radiation will develop recurrent prostate cancer (Walsh P C, Retik A B, Vaughan E D, eds. Campbell's Urology. 7th ed. Philadelphia, Pa.: WB Saunders Company; 1998). The most common treatment for recurrent prostate cancer is the suppression of testicular testosterone production via orchiectomy, estrogen treatment, antiandrogen administration, and/or GnRH agonist/antagonist treatment. This usually results in remission for 2-3 years, after which time prostate cancer becomes "hormone refractory," meaning that it develops the ability to grow despite the reduction of blood androgen concentrations to castrate levels. Consequently, improved compositions and methods are needed for treating prostate cancer, in particular hormone refractory prostate cancer.

Pituitary tumors (adenoma) are non-cancerous growths that typically affect different hormone-producing regions, depending on the specific location of the tumor. Pituitary tumors account for about 15% of intracranial tumors, and are associated with significant morbibity due to local compressive effects, hormonal hypersecretion, or treatment-associated endocrine deficiency (Heaney A. P., et al.: Molecular Pathogenesis of Pituitary Tumors. In: Oxford Textbook of Endocrinology, Wass J. A. H. and Shalet S. M., (Eds.), Oxford University Press, Oxford, 2002 (in press)). The great majority of pituitary adenomas are benign and are relatively slow growing. Pituitary tumors may, however, lead to overproduction of one or more of the pituitary hormones. FSH-secreting pituitary tumors often lead to the development of multicystic ovaries and to elevated estradiol levels. In turn, increases in estradiol levels contribute to health risks including endometrial and prostate cancer. Consequently, improved compositions and methods are needed for treating symptoms associated with FSH-secreting pituitary tumors.

Accordingly, compounds that inhibit FSH secretion are useful in a variety of treatments.

It is an object of the present disclosure to provide compositions and methods that may be used to decrease FSH levels, and such compositions and methods may be used, for example, in contraception and for the treatment of a variety of FSH-related disorders.

SUMMARY OF THE INVENTION

In part, the disclosure relates to the use of activin antagonists, as well as ActRIIa antagonists, to decrease or inhibit FSH secretion. In particular, the disclosure provides methods for decreasing or inhibiting FSH secretion using a soluble form of ActRIIa that acts as an inhibitor of activin. While soluble ActRIIa may affect FSH secretion through a mechanism other than activin antagonism, desirable therapeutic agents may nonetheless be selected on the basis of activin antagonism or ActRIIa antagonism or both. Such agents are referred to collectively as activin-ActRIIa antagonists. Therefore, in certain embodiments, the disclosure provides methods for using activin-ActRIIa antagonists, including, for example, activin-binding ActRIIa polypeptides, anti-activin antibodies, anti-ActRIIa antibodies, activin- or ActRIIa-targeted small molecules and aptamers, and nucleic acids that decrease expression of activin and ActRIIa, to decrease or inhibit FSH secretion in patients in need thereof. As described in U.S. Publication No. 2007/0249022, incorporated by reference herein, activin-ActRIIa antagonists can be used to promote bone growth and increase bone density. As described herein, such antagonists can also be used to decrease or inhibit FSH secretion.

In certain aspects, the disclosure provides methods for decreasing or inhibiting FSH secretion using polypeptides comprising a soluble, activin-binding ActRIIa polypeptide that binds to activin. ActRIIa polypeptides may be formulated as a pharmaceutical preparation comprising the activin-binding ActRIIa polypeptide and a pharmaceutically acceptable carrier. The activin-binding ActRIIa polypeptide may bind to activin with a $K_D$ less than 1 micromolar or less than 100, 10 or 1 nanomolar. Optionally, the activin-binding ActRIIa polypeptide selectively binds activin versus GDF11 and/or GDF8, and optionally with a $K_D$ that is at least 10-fold, 20-fold or 50-fold lower with respect to activin than with respect to GDF11 and/or GDF8. While not wishing to be bound to a particular mechanism of action, it is expected that this degree of selectivity for activin inhibition over GDF11/GDF8 inhibition accounts for effects on FSH secretion without a consistently measurable effect on muscle. In many embodiments, an ActRIIa polypeptide will be selected for causing less than 15%, less than 10% or less than 5% increase in muscle at doses that achieve desirable effects on FSH secretion. The composition may be at least 95% pure, with respect to other polypeptide components, as assessed by size exclusion chromatography, and optionally, the composition is at least 98% pure. An activin-binding ActRIIa polypeptide for use in such a preparation may be any of those disclosed herein, such as a polypeptide having an amino acid sequence selected from SEQ ID NOs: 2, 3, 7 or 12, or having an amino acid sequence that is at least 80%, 85%, 90%, 95%, 97% or 99% identical to an amino acid sequence selected from SEQ ID NOs: 2, 3, 7, 12 or 13. An activin-binding ActRIIa polypeptide may include a functional fragment of a natural ActRIIa polypeptide, such as one comprising at least 10, 20 or 30 amino acids of a sequence selected from SEQ ID NOs: 1-3 or a sequence of SEQ ID NO: 2, lacking the C-terminal 10 to 15 amino acids (the "tail").

In certain aspects, the disclosure provides methods for decreasing FSH levels in a human subject having an FSH-related disorder. Such a method may comprise administering to the subject an amount of an ActRIIa-Fc fusion protein effective to reduce FSH activity in the subject. In certain aspects, the disclosure provides methods for decreasing FSH levels in a patient desiring to delay or inhibit his or her germ cell maturation. Such a method may comprise administering an amount of ActRIIa-Fc fusion protein effective to reduce FSH activity in the subject. ActRIIa-Fc fusion protein may comprises an amino acid sequence that is at least 90%, 95%, 98%, 99% or 100% identical to the amino acid sequence of SEQ ID NO:3 or SEQ ID NO:2. The ActRIIa-Fc fusion protein may be a dimer formed of two polypeptides that each comprise an amino acid sequence that is at least 90%, 95%, 98%, 99% or 100% identical to the amino acid sequence of SEQ ID NO:3 or SEQ ID NO:2. The ActRIIa-Fc fusion protein may comprise three or more sialic acid moieties, particularly three, four or five sialic acid moieties. The ActRIIa-Fc fusion protein may be produced in CHO cells. The ActRIIa-Fc fusion protein may have an amino acid sequence of SEQ ID NO:7. The ActRIIa-Fc fusion protein may be administered so as to reach a serum concentration in the patient of at least 0.3 mg/kg, and preferably to reach a serum concentration ranging between 0.3 and 3 mg/kg. The ActRIIa-Fc fusion protein may have a serum half-life of between 15 and 30 days and may, for example, be administered to the subject no more frequently than once per week, once per month or once per year. In a certain embodiment, the ActRIIa-Fc fusion protein has a serum half-life of 25 to 32 days on average in normal, healthy humans and equivalent bioavailability when administered intravenously or subcutaneously. The ActRIIa-Fc fusion protein may be administered intravenously or subcutaneously.

A soluble, activin-binding ActRIIa polypeptide may include one or more alterations in the amino acid sequence (e.g., in the ligand-binding domain) relative to a naturally occurring ActRIIa polypeptide. Examples of altered ActRIIa polypeptides are provided in WO 2006/012627, pp. 59-60, incorporated by reference herein. The alteration in the amino acid sequence may, for example, alter glycosylation of the polypeptide when produced in a mammalian, insect or other eukaryotic cell or alter proteolytic cleavage of the polypeptide relative to the naturally occurring ActRIIa polypeptide.

An activin-binding ActRIIa polypeptide may be a fusion protein that has, as one domain, an ActRIIa polypeptide (e.g., a ligand-binding portion of an ActRIIa) and one or more additional domains that provide a desirable property, such as improved pharmacokinetics, easier purification, targeting to particular tissues, etc. For example, a domain of a fusion protein may enhance one or more of in vivo stability, in vivo half life, uptake/administration, tissue localization or distribution, formation of protein complexes, multimerization of the fusion protein, and/or purification. An activin-binding ActRIIa fusion protein may include an immunoglobulin Fc domain (wild-type or mutant) or a serum albumin or other polypeptide portion that provides desirable properties such as improved pharmacokinetics, improved solubility or improved stability. In a preferred embodiment, an ActRIIa-Fc fusion comprises a relatively unstructured linker positioned between the Fc domain and the extracellular ActRIIa domain. This unstructured linker may correspond to the roughly 15 amino acid unstructured region at the C-terminal end of the extracellular domain of ActRIIa (the "tail"), or it may be an artificial sequence of 1, 2, 3, 4 or 5 amino acids or a length of between 5 and 15, 20, 30, 50 or more amino acids that are relatively free of secondary structure, or a mixture of both. A linker may be rich in glycine and proline residues and may, for example, contain a single sequence of threonine/serine and glycines or repeating sequences of threonine/serine and glycines (e.g., $TG_4$ (SEQ ID NO: 15) or $SG_4$ (SEQ ID NO: 16) singlets or repeats). A fusion protein may include a purification subsequence, such as an epitope tag, a FLAG tag, a polyhistidine sequence, and a GST fusion. Optionally, a soluble ActRIIa polypeptide includes one or more modified amino acid residues selected from: a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent. Preferably, a pharmaceutical preparation is substantially pyrogen free. In general, it is preferable that an ActRIIa protein be expressed in a mammalian cell line that mediates suitably natural glycosylation of the ActRIIa protein so as to diminish the likelihood of an unfavorable immune response in a patient. Human and CHO cell lines have been used successfully, and it is expected that other common mammalian expression systems will be useful.

As described herein, ActRIIa proteins designated ActRIIa-Fc (a form with a minimal linker between the ActRIIa portion and the Fc portion) have desirable properties, including selective binding to activin versus GDF8 and/or GDF11, high affinity ligand binding and serum half life greater than two weeks in animal models. In certain embodiments the invention provides methods for decreasing or inhibiting FSH secretion using ActRIIa-Fc polypeptides and pharmaceutical preparations comprising such polypeptides and a pharmaceutically acceptable excipient.

In certain aspects, the disclosure provides methods for decreasing or inhibiting FSH secretion using nucleic acids encoding a soluble activin-binding ActRIIa polypeptide. An isolated polynucleotide may comprise a coding sequence for a soluble, activin-binding ActRIIa polypeptide, such as described above. For example, an isolated nucleic acid may include a sequence coding for an extracellular domain (e.g., ligand-binding domain) of an ActRIIa and a sequence that would code for part or all of the transmembrane domain and/or the cytoplasmic domain of an ActRIIa, but for a stop codon positioned within the transmembrane domain or the cytoplasmic domain, or positioned between the extracellular domain and the transmembrane domain or cytoplasmic domain. For example, an isolated polynucleotide may comprise a full-length ActRIIa polynucleotide sequence such as SEQ ID NO: 4 or 5, or a partially truncated version, said isolated polynucleotide further comprising a transcription termination codon at least six hundred nucleotides before the 3'-terminus or otherwise positioned such that translation of the polynucleotide gives rise to an extracellular domain optionally fused to a truncated portion of a full-length ActRIIa. A preferred nucleic acid sequence is SEQ ID NO:14.

Nucleic acids useful in accordance with the methods described herein may be operably linked to a promoter for expression, and the disclosure provides cells transformed with such recombinant polynucleotides. Preferably the cell is a mammalian cell such as a CHO cell.

The disclosure also provides methods for making a soluble, activin-binding ActRIIa polypeptide that can be used for decreasing or inhibiting FSH secretion. Such a method may include expressing any of the nucleic acids (e.g., SEQ ID NO: 4, 5 or 14) disclosed herein in a suitable cell, such as a Chinese hamster ovary (CHO) cell. Such a method may comprise: a) culturing a cell under conditions suitable for expression of the soluble ActRIIa polypeptide, wherein said cell is transformed with a soluble ActRIIa expression construct; and b) recovering the soluble ActRIIa polypeptide so expressed. Soluble ActRIIa polypeptides may be recovered as crude, partially purified or highly purified fractions. Purification may be achieved by a series of purification steps, including, for example, one, two or three or more of the following, in any order: protein A chromatography, anion exchange chromatography (e.g., Q sepharose), hydrophobic interaction chromatography (e.g., phenylsepharose), size exclusion chromatography, and cation exchange chromatography.

In certain aspects, an activin-ActRIIa antagonist disclosed herein, such as a soluble, activin-binding ActRIIa polypeptide, may be used in a method for decreasing or inhibiting FSH secretion in a subject, including, for example, methods for delaying the onset of prostate cancer, inhibiting the progression of prostrate cancer, reducing tumor size, preventing tumor growth, delaying the onset of metastasis or preventing metastasis. In certain embodiments, the disclosure provides methods for decreasing or inhibiting the growth or survival of prostate cancer cells in patients in need thereof. A method may comprise administering to a subject in need thereof an effective amount of activin-ActRIIa antagonist. In certain aspects, the disclosure provides uses of activin-ActRIIa antagonists for making a medicament for the treatment or prevention of prostate cancer as described herein. The disclosure also relates to combination therapies comprising an activin-ActRIIa antagonist and radiation therapy, chemotherapy (e.g., a cytotoxic agent), and/or endocrine therapy. The antagonist may be an ActRIIa-Fc fusion protein, wherein the ActRIIa-Fc fusion protein comprises an amino acid sequence that is at least 90% identical to the amino acid sequence of SEQ ID NO:3, 6, 7, or 13.

In further embodiments, the present invention relates to methods of preventing or delaying the onset of prostate cancer in patients with one or more prostate cancer risk factors. In some embodiments, the invention relates to methods of preventing or delaying the onset of metastatic disease in patients already diagnosed with a primary prostate tumor or with a proliferative lesion of the prostate. The method of preventing or delaying the onset of prostate cancer in a human patient may comprise administering to a human patient in need thereof an effective amount of a polypeptide selected from the group consisting of: a) a polypeptide comprising an amino acid sequence at least 90% identical to SEQ ID NO:2; b) a polypeptide comprising an amino acid sequence at least 90% identical to SEQ ID NO:3; and c) a polypeptide comprising at least 50 consecutive amino acids selected from SEQ ID NO: 2.

Other embodiments of the invention relate to a method of inhibiting activin-mediated signaling in a human patient with prostate cancer. In certain embodiments, the method comprises administering to the human patient an effective amount of an activin-ActRIIa antagonist. In further embodiments, the antagonist is a polypeptide selected from the group consisting of: a) a polypeptide comprising an amino acid sequence at least 90% identical to SEQ ID NO:2; b) a polypeptide comprising an amino acid sequence at least 90% identical to SEQ ID NO:3; and c) a polypeptide comprising at least 50 consecutive amino acids selected from SEQ ID NO: 2.

In certain embodiments, the decrease or inhibition of FSH secretion causes a reduction in fertility. In females, administration of activin-ActRII antagonists limit proliferation of follicular granulosa cells. In males, administration of activin-ActRII antagonists inhibits sperm maturation. In certain aspects, the disclosure provides methods and compositions for contraceptives. In certain embodiments, compositions are provided comprising activin-ActRII antagonists and one or more oral contraceptive agents, such as progestin, progesterone, and estrogen.

In certain embodiments, methods are provided for decreasing or inhibiting FSH secretions in patients afflicted with FSH-secreting pituitary tumor; the methods comprising administering activin-ActRII antagonists.

In certain aspects, the disclosure provides a method for identifying an agent that inhibits the growth or survival of cancer cells (e.g., prostate cancer cells). The method comprises: a) identifying a test agent that binds to activin or a ligand-binding domain of an ActRIIa polypeptide; and b) evaluating the effect of the agent on the proliferation, survival, or apoptosis of cancer cells.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 shows the binding of ActRIIa-hFc to activin and GDF-11, as measured by BiaCore™ assay.

FIG. 19 shows the effects of ActrIIa-mFc on trabecular bone volume.

FIG. 20 shows the effects of ActrIIa-mFc on trabecular architecture in the distal femur.

FIG. 21 shows the effects of ActrIIa-mFc on cortical bone.

FIG. 24 shows bone histomorphometry indicating that ActRIIa-mFc has dual anabolic and anti-resorptive activity.

FIG. 25 shows additional histomorphometric data.

DETAILED DESCRIPTION OF THE INVENTION

1. Overview

Figure 1:
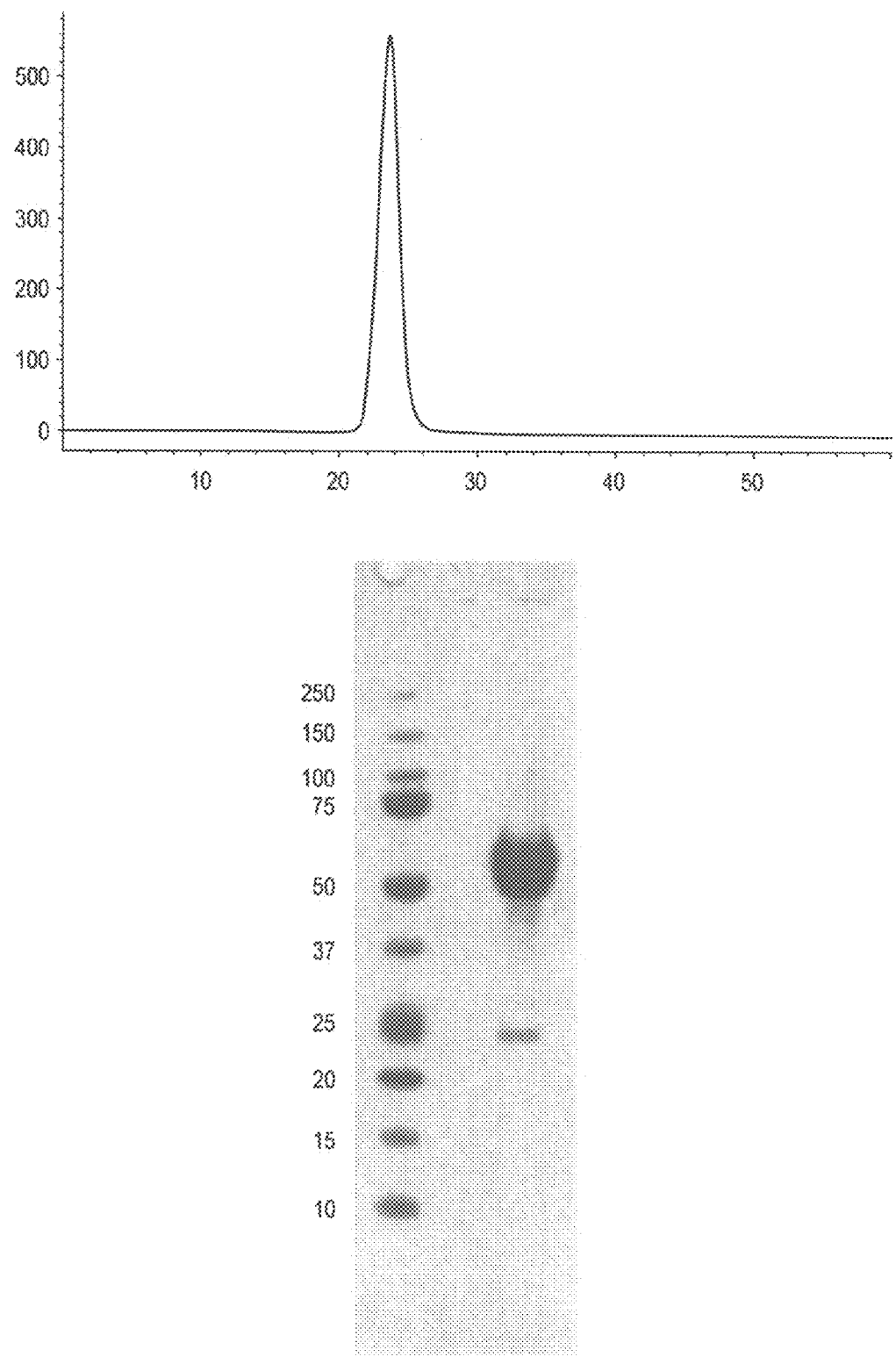
FIG. 1 shows the purification of ActRIIa-hFc expressed in CHO cells. The protein purifies as a single, well-defined peak.

The transforming growth factor-beta (TGF-beta) superfamily contains a variety of growth factors that share common sequence elements and structural motifs. These proteins are known to exert biological effects on a large variety of cell types in both vertebrates and invertebrates. Members of the superfamily perform important functions during embryonic development in pattern formation and tissue specification and can influence a variety of differentiation processes, including adipogenesis, myogenesis, chondrogenesis, cardiogenesis, hematopoiesis, neurogenesis, and epithelial cell differentiation. The family is divided into two general branches: the BMP/GDF and the TGF-beta/Activin branches, whose members have diverse, often complementary effects. By manipulating the activity of a member of the TGF-beta family, it is often possible to cause significant physiological changes in an organism. For example, the Piedmontese and Belgian Blue cattle breeds carry a loss-of-function mutation in the GDF8 (also called myostatin) gene that causes a marked increase in muscle mass. Grobet et al., Nat. Genet. 1997, 17(1):71-4. Furthermore, in humans, inactive alleles of GDF8 are associated with increased muscle mass and, reportedly, exceptional strength. Schuelke et al., N Engl J Med 2004, 350: 2682-8.

Activins are dimeric polypeptide growth factors that belong to the TGF-beta superfamily. There are three principal activin forms (A, B, and AB) that are homo/heterodimers of two closely related β subunits ($β_Aβ_A$, $β_Bβ_B$, and $β_Aβ_B$, respectively). The human genome also encodes an activin C and an activin E, which are primarily expressed in the liver, and heterodimeric forms containing $β_C$ or $β_E$ are also known. In the TGF-beta superfamily, activins are unique and multifunctional factors that can stimulate hormone production in ovarian and placental cells, support neuronal cell survival, influence cell-cycle progress positively or negatively depending on cell type, and induce mesodermal differentiation at least in amphibian embryos (DePaolo et al., 1991, Proc Soc Ep Biol Med. 198:500-512; Dyson et al., 1997, Curr Biol. 7:81-84; Woodruff, 1998, Biochem Pharmacol. 55:953-963). In several tissues, activin signaling is antagonized by its related heterodimer, inhibin. For example, during the release of follicle-stimulating hormone (FSH) from the pituitary, activin promotes FSH secretion and synthesis, while inhibin prevents FSH secretion and synthesis. Other proteins that may regulate activin bioactivity and/or bind to activin include follistatin (FS), follistatin-related protein (FSRP) and $\alpha_2$-macroglobulin.

TGF-$\beta$ signals are mediated by heteromeric complexes of type I and type II serine/threonine kinase receptors, which phosphorylate and activate downstream Smad proteins upon ligand stimulation (Massagué, 2000, Nat. Rev. Mol. Cell. Biol. 1: 169-178). These type I and type II receptors are transmembrane proteins, composed of a ligand-binding extracellular domain with cysteine-rich region, a transmembrane domain, and a cytoplasmic domain with predicted serine/threonine specificity. Type I receptors are essential for signaling; and type II receptors are required for binding ligands and for expression of type I receptors. Type I and II activin receptors form a stable complex after ligand binding, resulting in phosphorylation of type I receptors by type II receptors.

Two related type II receptors, ActRIIa and ActRIIb, have been identified as the type II receptors for activins (Mathews and Vale, 1991, Cell 65:973-982; Attisano et al., 1992, Cell 68: 97-108). Besides activins, ActRIIa and ActRIIb can biochemically interact with several other TGF-$\beta$ family proteins, including BMP7, Nodal, GDF8, and GDF11 (Yamashita et al., 1995, J. Cell Biol. 130:217-226; Lee and McPherron, 2001, Proc. Natl. Acad. Sci. 98:9306-9311; Yeo and Whitman, 2001, Mol. Cell. 7: 949-957; Oh et al., 2002, Genes Dev. 16:2749-54). ALK4 is the primary type I receptor for activins, particularly for activin A, and ALK-7 may serve as a receptor for activins as well, particularly for activin B.

As described herein, a soluble ActRIIa polypeptide (sActRIIa), which shows substantial preference in binding to activin A as opposed to other TGF-beta family members, such as GDF8 or GDF11, may be used to decrease or inhibit FSH secretion. While not wishing to be bound to any particular mechanism, it is expected that the effect of sActRIIa is caused primarily by an activin antagonist effect, given the very strong activin binding (picomolar dissociation constant) exhibited by the particular sActRIIa construct used in these studies. Activin-ActRIIa antagonists include, for example, activin-binding soluble ActRIIa polypeptides, antibodies that bind to activin (particularly the activin A or B subunits, also referred to as $\beta$A or $\beta$B) and disrupt ActRIIa binding, antibodies that bind to ActRIIa and disrupt activin binding, non-antibody proteins selected for activin or ActRIIa binding (see e.g., WO/2002/088171, WO/2006/055689, and WO/2002/032925 for examples of such proteins and methods for design and selection of same), randomized peptides selected for activin or ActRIIa binding, often affixed to an Fc domain. Two different proteins (or other moieties) with activin or ActRIIa binding activity, especially activin binders that block the type I (e.g., a soluble type I activin receptor) and type II (e.g., a soluble type II activin receptor) binding sites, respectively, may be linked together to create a bifunctional binding molecule. Nucleic acid aptamers, small molecules and other agents that inhibit the activin-ActRIIa signaling axis. Various proteins have activin-ActRIIa antagonist activity, including inhibin (i.e., inhibin alpha subunit), although inhibin does not universally antagonize activin in all tissues, follistatin (e.g., follistatin-288 and follistatin-315), FSRP, activin C, alpha (2)-macroglobulin, and an M108A (methionine to alanine change at position 108) mutant activin A. Generally, alternative forms of activin, particularly those with alterations in the type I receptor binding domain can bind to type II receptors and fail to form an active ternary complex, thus acting as antagonists. Additionally, nucleic acids, such as antisense molecules, siRNAs or ribozymes that inhibit activin A, B, C or E, or, particularly, ActRIIa expression, can be used as activin-ActRIIa antagonists. The activin-ActRIIa antagonist to be used may exhibit selectivity for inhibiting activin-mediated signaling versus other members of the TGF-beta family, and particularly with respect to GDF8 and GDF11. Soluble ActRIIb proteins do bind to activin, however, the wild type protein does not exhibit significant selectivity in binding to activin versus GDF8/11. Nonetheless, such ActRIIb polypeptides, as well as altered forms of ActRIIb with different binding properties (see, e.g., WO 2006/012627, pp. 55-59, incorporated herein by reference) may achieve the desired effects on cancer cells. Native or altered ActRIIb may be given added specificity for activin by coupling with a second, activin-selective binding agent.

The terms used in this specification generally have their ordinary meanings in the art, within the context of this invention and in the specific context where each term is used. Certain terms are discussed below or elsewhere in the specification, to provide additional guidance to the practitioner in describing the compositions and methods of the invention and how to make and use them. The scope or meaning of any use of a term will be apparent from the specific context in which the term is used.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values.

Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The methods of the invention may include steps of comparing sequences to each other, including wild-type sequence to one or more mutants (sequence variants). Such comparisons typically comprise alignments of polymer sequences, e.g., using sequence alignment programs and/or algorithms that are well known in the art (for example, BLAST, FASTA and MEGALIGN, to name a few). The skilled artisan can readily appreciate that, in such alignments, where a mutation contains a residue insertion or deletion, the sequence alignment will introduce a "gap" (typically represented by a dash, or "A") in the polymer sequence not containing the inserted or deleted residue.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions.

The term "sequence similarity," in all its grammatical forms, refers to the degree of identity or correspondence between nucleic acid or amino acid sequences that may or may not share a common evolutionary origin.

However, in common usage and in the instant application, the term "homologous," when modified with an adverb such as "highly," may refer to sequence similarity and may or may not relate to a common evolutionary origin.

The term "prostate cancer" refers to any proliferative lesion or proliferative abnormality of the prostate including, for example, benign lesions, pre-malignant and malignant lesions, solid tumors, and metastatic disease (both locally metastatic, e.g., stage III, and more widely metastatic, e.g., stage 1V). Prostate cancer also encompasses both hormone-responsive and hormone-independent cancers. Hormone-refractory prostate cancers are refractory to treatment with anti-hormonal (especially antiestrogenic) therapies.

2. ActRIIa Polypeptides

In certain aspects, the present invention relates to ActRIIa polypeptides. As used herein, the term "ActRIIa" refers to a family of activin receptor type IIa (ActRIIa) proteins from any species and variants derived from such ActRIIa proteins by mutagenesis or other modification. Reference to ActRIIa herein is understood to be a reference to any one of the currently identified forms. Members of the ActRIIa family are generally transmembrane proteins, composed of a ligand-binding extracellular domain with a cysteine-rich region, a transmembrane domain, and a cytoplasmic domain with predicted serine/threonine kinase activity.

The term "ActRIIa polypeptide" includes polypeptides comprising any naturally occurring polypeptide of an ActRIIa family member as well as any variants thereof (including mutants, fragments, fusions, and peptidomimetic forms) that retain a useful activity. For example, ActRIIa polypeptides include polypeptides derived from the sequence of any known ActRIIa having a sequence at least about 80% identical to the sequence of an ActRIIa polypeptide, and preferably at least 85%, 90%, 95%, 97%, 99% or greater identity. For example, an ActRIIa polypeptide of the invention may bind to and inhibit the function of an ActRIIa protein and/or activin. Preferably, an ActRIIa polypeptide decreases FSH levels in vivo or in an in vitro assay conducted using pituitary cells. Examples of ActRIIa polypeptides include human ActRIIa precursor polypeptide (SEQ ID NO: 1) and soluble human ActRIIa polypeptides (e.g., SEQ ID NOs: 2, 3, 7 and 12).

The human ActRIIa precursor protein sequence is as follows:

(SEQ ID NO: 1)
MGAAAKLAFAVFLISCSSGAILGRSETQECLFFNANWEKDRTNQTGVEPC

YGDKDKRRHCFATWKNISGSIEIVKQGCWLDDINCYDRTDCVEKKDSPEV

YFCCCEGNMCNEKFSYFPEMEVTQPTSNPVTPKPPYYNILLYSLVPLMLI

AGIVICAFWVYRHHKMAYPPVLVPTQDPGPPPPSPLLGLKPLQLLEVKAR

GRFGCVWKAQLLNEYVAVKIFPIQDKQSWQNEYEVYSLPGMKHENILQFT

GAEKRGTSVDVDLWLITAFHEKGSLSDELKANVVSWNELCHIAETMARGL

AYLHEDIPGLKDGHKPAISHRDIKSKNVLLKNNLTACIADFGLALKFEAG

KSAGDTHGQVGTRRYMAPEVLEGAINFQRDAFLRIDMYAMGLVLWELASR

CTAADGPVDEYMLPFEEEIGQHPSLEDMQEVVVHKKKRPVLRDYWQKHAG

MAMLCETIEECWDHDAEARLSAGCVGERITQMQRLTNIITTEDIVTVVTM

VTNVDFPPKESSL

The signal peptide is single underlined; the extracellular domain is in bold and the potential N-linked glycosylation sites are double underlined.

The human ActRIIa soluble (extracellular), processed polypeptide sequence is as follows:

(SEQ ID NO: 2)
ILGRSETQECLFFNANWEKDRTNQTGVEPCYGDKDKRRHCFATWKNISGS

IEIVKQGCWLDDINCYDRTDCVEKKDSPEVYFCCCEGNMCNEKFSYFPEM

EVTQPTSNPVTPKPP

The C-terminal "tail" of the extracellular domain is underlined. The sequence with the "tail" deleted (a Δ15 sequence) is as follows:

(SEQ ID NO:3)
ILGRSETQECLFFNANWEKDRTNQTGVEPCYGDKDKRRHCFATWKNISGS

IEIVKQGCWLDDINCYDRTDCVEKKDSPEVYFCCCEGNMCNEKFSYFPEM

The nucleic acid sequence encoding human ActRIIa precursor protein is as follows(nucleotides 164-1705 of Genbank entry NM_001616):

(SEQ ID NO: 4)
ATGGGAGCTGGTGCAAAGTTGGCGTTTGCCGTCTTTCTTATCTCCTGTTC

TTCAGGTGCTATACTTGGTAGATCAGAAACTCAGGAGTGTCTTTTCTTTA

ATGCTAATTGGGAAAAAGACAGAACCAATCAAACTGGTGTTGAACCGTGT

TATGGTGACAAAGATAAACGGCGGCATTGTTTTGCTACCTGGAAGAATAT

TTCTGGTTCCATTGAAATAGTGAAACAAGGTTGTTGGCTGGATGATATCA

ACTGCTATGACAGGACTGATTGTGTAGAAAAAAAAGACAGCCCTGAAGTA

TATTTTTGTTGCTGTGAGGGCAATATGTGTAATGAAAAGTTTTCTTATTT

TCCAGAGATGGAAGTCACACAGCCCACTTCAAATCCAGTTACACCTAAGC

CACCCTATTACAACATCCTGCTCTATTCCTTGGTGCCACTTATGTTAATT

GCGGGGATTGTCATTTGTGCATTTTGGGTGTACAGGCATCACAAGATGGC

CTACCCTCCTGTACTTGTTCCAACTCAAGACCCAGGACCACCCCCACCTT

CTCCATTACTAGGGTTGAAACCACTGCAGTTATTAGAAGTGAAAGCAAGG

GGAAGATTTGGTTGTGTCTGGAAAGCCCAGTTGCTTAACGAATATGTGGC

TGTCAAAATATTTCCAATACAGGACAAACAGTCATGGCAAAATGAATACG

AAGTCTACAGTTTGCCTGGAATGAAGCATGAGAACATATTACAGTTCATT

GGTGCAGAAAAACGAGGCACCAGTGTTGATGTGGATCTTTGGCTGATCAC

AGCATTTCATGAAAAGGGTTCACTATCAGACTTTCTTAAGGCTAATGTGG

TCTCTTGGAATGAACTGTGTCATATTGCAGAAACCATGGCTAGAGGATTG

GCATATTTACATGAGGATATACCTGGCCTAAAAGATGGCCACAAACCTGC

CATATCTCACAGGGACATCAAAAGTAAAAATGTGCTGTTGAAAAACAACC

TGACAGCTTGCATTGCTGACTTTGGGTTGGCCTTAAAATTTGAGGCTGGC

AAGTCTGCAGGCGATACCCATGGACAGGTTGGTACCCGGAGGTACATGGC

TCCAGAGGTATTAGAGGGTGCTATAAACTTCCAAAGGGATGCATTTTTGA

GGATAGATATGTATGCCATGGGATTAGTCCTATGGGAACTGGCTTCTCGC

TGTACTGCTGCAGATGGACCTGTAGATGAATACATGTTGCCATTTGAGGA

GGAAATTGGCCAGCATCCATCTCTTGAAGACATGCAGGAAGTTGTTGTGC

-continued

```
ATAAAAAAAAGAGGCCTGTTTTAAGAGATTATTGGCAGAAACATGCTGGA

ATGGCAATGCTCTGTGAAACCATTGAAGAATGTTGGGATCACGACGCAGA

AGCCAGGTTATCAGCTGGATGTGTAGGTGAAAGAATTACCCAGATGCAGA

GACTAACAAATATTATTACCACAGAGGACATTGTAACAGTGGTCACAATG

GTGACAAATGTTGACTTTCCTCCCAAAGAATCTAGTCTATGA
```

The nucleic acid sequence encoding a human ActRIIa soluble (extracellular) polypeptide is as follows:

```
                                          (SEQ ID NO: 5)
ATACTTGGTAGATCAGAAACTCAGGAGTGTCTTTTCTTTAATGCTAATTG

GGAAAAAGACAGAACCAATCAAACTGGTGTTGAACCGTGTTATGGTGACA

AAGATAAACGGCGGCATTGTTTTGCTACCTGGAAGAATATTTCTGGTTCC

ATTGAAATAGTGAAACAAGGTTGTTGGCTGGATGATATCAACTGCTATGA

CAGGACTGATTGTGTAGAAAAAAAAGACAGCCCTGAAGTATATTTTGTT

GCTGTGAGGGCAATATGTGTAATGAAAAGTTTTCTTATTTTCCAGAGATG

GAAGTCACACAGCCCACTTCAAATCCAGTTACACCTAAGCCACCC
```

In a specific embodiment, the invention relates to soluble ActRIIa polypeptides and their uses in decreasing FSH levels. As described herein, the term "soluble ActRIIa polypeptide" generally refers to polypeptides comprising an extracellular domain of an ActRIIa protein. The term "soluble ActRIIa polypeptide," as used herein, includes any naturally occurring extracellular domain of an ActRIIa protein as well as any variants thereof (including mutants, fragments and peptidomimetic forms). An activin-binding ActRIIa polypeptide is one that retains the ability to bind to activin, particularly activin AA, AB or BB. Preferably, an activin-binding ActRIIa polypeptide will bind to activin AA with a dissociation constant of 1 nM or less. Amino acid sequences of human ActRIIa precursor protein is provided below. The extracellular domain of an ActRIIa protein binds to activin and is generally soluble, and thus can be termed a soluble, activin-binding ActRIIa polypeptide. Examples of soluble, activin-binding ActRIIa polypeptides include the soluble polypeptide illustrated in SEQ ID NOs: 2, 3, 7, 12 and 13. SEQ ID NO:7 is referred to as ActRIIa-hFc, and is described further in the Examples. Other examples of soluble, activin-binding ActRIIa polypeptides comprise a signal sequence in addition to the extracellular domain of an ActRIIa protein, for example, the honey bee mellitin leader sequence (SEQ ID NO: 8), the tissue plaminogen activator (TPA) leader (SEQ ID NO: 9) or the native ActRIIa leader (SEQ ID NO: 10). The ActRIIa-hFc polypeptide illustrated in SEQ ID NO:13 uses a TPA leader.

Functionally active fragments of ActRIIa polypeptides can be obtained by screening polypeptides recombinantly produced from the corresponding fragment of the nucleic acid encoding an ActRIIa polypeptide. In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments that can function as antagonists (inhibitors) of ActRIIa protein or signaling mediated by activin.

Functionally active variants of ActRIIa polypeptides can be obtained by screening libraries of modified polypeptides recombinantly produced from the corresponding mutagenized nucleic acids encoding an ActRIIa polypeptide. The variants can be produced and tested to identify those that can function as antagonists (inhibitors) of ActRIIa protein or signaling mediated by activin. In certain embodiments, a functional variant of the ActRIIa polypeptides comprises an amino acid sequence that is at least 75% identical to an amino acid sequence selected from SEQ ID NOs: 2 or 3. In certain cases, the functional variant has an amino acid sequence at least 80%, 85%, 90%, 95%, 97%, 98%, 99% or 100% identical to an amino acid sequence selected from SEQ ID NOs: 2 or 3.

Functional variants may be generated by modifying the structure of an ActRIIa polypeptide for such purposes as enhancing therapeutic efficacy, or stability (e.g., ex vivo shelf life and resistance to proteolytic degradation in vivo). Such modified ActRIIa polypeptides when selected to retain activin binding, are considered functional equivalents of the naturally-occurring ActRIIa polypeptides. Modified ActRIIa polypeptides can also be produced, for instance, by amino acid substitution, deletion, or addition. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of an ActRIIa polypeptide results in a functional homolog can be readily determined by assessing the ability of the variant ActRIIa polypeptide to produce a response in cells in a fashion similar to the wild-type ActRIIa polypeptide.

In certain embodiments, the present invention contemplates specific mutations of the ActRIIa polypeptides so as to alter the glycosylation of the polypeptide. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine (or asparagines-X-serine) (where "X" is any amino acid) which is specifically recognized by appropriate cellular glycosylation enzymes. The alteration may also be made by the addition of, or substitution by, one or more serine or threonine residues to the sequence of the wild-type ActRIIa polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on an ActRIIa polypeptide is by chemical or enzymatic coupling of glycosides to the ActRIIa polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. These methods are described in WO 87/05330 published Sep. 11, 1987, and in Aplin and Wriston (1981) CRC Crit. Rev. Biochem., pp. 259-306, incorporated by reference herein. Removal of one or more carbohydrate moieties present on an ActRIIa polypeptide may be accomplished chemically and/or enzymatically. Chemical deglycosylation may involve, for example, exposure of the ActRIIa polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Chemical deglycosylation is further described by Hakimuddin et al. (1987) Arch. Biochem. Biophys. 259:52 and by Edge et al. (1981) Anal. Biochem. 118:131. Enzymatic cleavage of carbohydrate moieties on ActRIIa polypeptides can be achieved by the use of a variety of endo- and exo-glycosidases as described by Thotakura et al. (1987) Meth. Enzymol. 138:350. The sequence of an ActRIIa polypeptide may be adjusted, as appropriate, depending on the type of expression system used, as mammalian, yeast, insect and plant cells may all introduce differing glycosylation patterns that can be affected by the amino acid sequence of the peptide. In general, ActRIIa proteins for use in humans will be expressed in a mammalian cell line that provides proper glycosylation, such as HEK293 or CHO cell lines, although other mammalian expression cell lines, yeast cell lines with engineered glycosylation enzymes and insect cells are expected to be useful as well.

This disclosure further contemplates a method of generating mutants, particularly sets of combinatorial mutants of an ActRIIa polypeptide, as well as truncation mutants; pools of combinatorial mutants are especially useful for identifying functional variant sequences. The purpose of screening such combinatorial libraries may be to generate, for example, ActRIIa polypeptide variants which can act as either agonists or antagonist, or alternatively, which possess novel activities all together. A variety of screening assays are provided below, and such assays may be used to evaluate variants. For example, an ActRIIa polypeptide variant may be screened for ability to bind to an ActRIIa ligand, to prevent binding of an ActRIIa ligand to an ActRIIa polypeptide or to interfere with signaling caused by an ActRIIa ligand.

The activity of an ActRIIa polypeptide or its variants may also be tested in a cell-based or in vivo assay. For example, the effect of an ActRIIa polypeptide variant on the expression of genes involved in FSH production. This may, as needed, be performed in the presence of one or more recombinant ActRIIa ligand proteins (e.g., activin), and cells may be transfected so as to produce an ActRIIa polypeptide and/or variants thereof, and optionally, an ActRIIa ligand. Likewise, an ActRIIa polypeptide may be administered to a mouse or other animal, and FSH levels may be assessed. Pituitary cell lines that produce FSH are well known and ActRIIa proteins may be tested for efficacy in reducing FSH production, particularly in the presence of exogenously supplied activin. As another example, the effect of an ActRIIa polypeptide variant on the proliferation or survival of cancer cells may be assessed. Cancer cells may refer to cells in a living subject that make up a solid tumor or to cells that have originated from a tumor and that have spread to other sites within a living subject (i.e., metastatic cells). Additionally, cancer cells may refer to cells obtained or derived from a tumor or cancerous growth and that are cultured in vitro. Cancer cells also encompass cell lines that may be cultivated in vitro or used in animal xenograft studies, for example. Cancer cells also refer to cells derived from metastatic cells through cell division following metastasis. The cells may be hormone-responsive or hormone-independent. Cancer cell proliferation or survival may be assessed in the presence of one or more recombinant ActRIIa ligand proteins (e.g., activin), and cells may be transfected so as to produce an ActRIIa polypeptide and/or variants thereof, and optionally, an ActRIIa ligand. Likewise, an ActRIIa polypeptide may be administered to a mouse or other animal, and one or more measurements, such as tumor size, or the rate of cell proliferation or apoptosis relative to a control, may be assessed.

Combinatorially-derived variants can be generated which have a selective or generally increased potency relative to a naturally occurring ActRIIa polypeptide. Likewise, mutagenesis can give rise to variants which have intracellular half-lives dramatically different than the corresponding a wild-type ActRIIa polypeptide. For example, the altered protein can be rendered either more stable or less stable to proteolytic degradation or other cellular processes which result in destruction of, or otherwise inactivation of a native ActRIIa polypeptide. Such variants, and the genes which encode them, can be utilized to alter ActRIIa polypeptide levels by modulating the half-life of the ActRIIa polypeptides. For instance, a short half-life can give rise to more transient biological effects and can allow tighter control of recombinant ActRIIa polypeptide levels within the patient. In an Fc fusion protein, mutations may be made in the linker (if any) and/or the Fc portion to alter the half-life of the protein.

A combinatorial library may be produced by way of a degenerate library of genes encoding a library of polypeptides which each include at least a portion of potential ActRIIa polypeptide sequences. For instance, a mixture of synthetic oligonucleotides can be enzymatically ligated into gene sequences such that the degenerate set of potential ActRIIa polypeptide nucleotide sequences are expressible as individual polypeptides, or alternatively, as a set of larger fusion proteins (e.g., for phage display).

There are many ways by which the library of potential homologs can be generated from a degenerate oligonucleotide sequence. Chemical synthesis of a degenerate gene sequence can be carried out in an automatic DNA synthesizer, and the synthetic genes then be ligated into an appropriate vector for expression. The synthesis of degenerate oligonucleotides is well known in the art (see for example, Narang, S A (1983) Tetrahedron 39:3; Itakura et al., (1981) Recombinant DNA, Proc. 3rd Cleveland Sympos. Macromolecules, ed. AG Walton, Amsterdam: Elsevier pp 273-289; Itakura et al., (1984) Annu. Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, ActRIIa polypeptide variants can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell. Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34).

Linker scanning mutagenesis, particularly in a combinatorial setting, is an attractive method for identifying truncated (bioactive) forms of ActRIIa polypeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of ActRIIa polypeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Preferred assays include activin binding assays and activin-mediated cell signaling assays.

In certain embodiments, the ActRIIa polypeptides of the invention may further comprise post-translational modifications in addition to any that are naturally present in the ActRIIa polypeptides. Such modifications include, but are not limited to, acetylation, carboxylation, glycosylation, phosphorylation, lipidation, and acylation. As a result, the modified ActRIIa polypeptides may contain non-amino acid elements, such as polyethylene glycols, lipids, poly- or monosaccharide, and phosphates. Effects of such non-amino acid elements on the functionality of a ActRIIa polypeptide may be tested as described herein for other ActRIIa polypeptide variants. When an ActRIIa polypeptide is produced in cells by cleaving a nascent form of the ActRIIa polypeptide, post-translational processing may also be important for correct folding and/or function of the protein. Different cells (such as CHO, HeLa, MDCK, 293, WI38, NIH-3T3 or HEK293) have specific cellular machinery and characteristic mechanisms for such post-translational activities and may be chosen to ensure the correct modification and processing of the ActRIIa polypeptides.

In certain aspects, functional variants or modified forms of the ActRIIa polypeptides include fusion proteins having at least a portion of the ActRIIa polypeptides and one or more fusion domains. Well known examples of such fusion domains include, but are not limited to, polyhistidine, Glu-Glu, glutathione S transferase (GST), thioredoxin, protein A, protein G, an immunoglobulin heavy chain constant region (Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt- conjugated resins are used. Many of such matrices are available in "kit" form, such as the Pharmacia GST purification system and the QIAexpress™ system (Qiagen) useful with (HIS$_6$) fusion partners. As another example, a fusion domain may be selected so as to facilitate detection of the ActRIIa polypeptides. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain preferred embodiments, an ActRIIa polypeptide is fused with a domain that stabilizes the ActRIIa polypeptide in vivo (a "stabilizer" domain). By "stabilizing" is meant anything that increases serum half life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties. Other types of fusion domains that may be selected include multimerizing (e.g., dimerizing, tetramerizing) domains and functional domains (that confer an additional biological function, such as further stimulation of bone growth or muscle growth, as desired).

As a specific example, the present invention provides a fusion protein comprising a soluble extracellular domain of ActRIIa fused to an Fc domain (e.g., SEQ ID NO: 6).

THTCPPCPAPELLGGPSVFLPPPKPKDTLMISRTPEVTCVVVD(A)VSHE

DPEVKFNWYVDGVEVHNAKTKPREEQYNSTYRVVSVLTVLHQDWLNGKEY

KCK(A)VSNKALPVPIEKTISKAKGQPREPQVYTLPPSREEMTKNQVSLT

CLVKGFYPSDIAVEWESNGQPENNYKTTPPVLDSDGPFFLYSKLTVDKSR

WQQGNVFSCSVMHEALHN(A)HYTQKSLSLSPGK*

Optionally, the Fc domain has one or more mutations at residues such as Asp-265, lysine 322, and Asn-434. In certain cases, the mutant Fc domain having one or more of these mutations (e.g., Asp-265 mutation) has reduced ability of binding to the Fcγ receptor relative to a wildtype Fc domain. In other cases, the mutant Fc domain having one or more of these mutations (e.g., Asn-434 mutation) has increased ability of binding to the MHC class I-related Fc-receptor (FcRN) relative to a wildtype Fc domain.

It is understood that different elements of the fusion proteins may be arranged in any manner that is consistent with the desired functionality. For example, an ActRIIa polypeptide may be placed C-terminal to a heterologous domain, or, alternatively, a heterologous domain may be placed C-terminal to an ActRIIa polypeptide. The ActRIIa polypeptide domain and the heterologous domain need not be adjacent in a fusion protein, and additional domains or amino acid sequences may be included C- or N-terminal to either domain or between the domains.

In certain embodiments, the ActRIIa polypeptides of the present invention contain one or more modifications that are capable of stabilizing the ActRIIa polypeptides. For example, such modifications enhance the in vitro half life of the ActRIIa polypeptides, enhance circulatory half life of the ActRIIa polypeptides or reduce proteolytic degradation of the ActRIIa polypeptides. Such stabilizing modifications include, but are not limited to, fusion proteins (including, for example, fusion proteins comprising an ActRIIa polypeptide and a stabilizer domain), modifications of a glycosylation site (including, for example, addition of a glycosylation site to an ActRIIa polypeptide), and modifications of carbohydrate moiety (including, for example, removal of carbohydrate moieties from an ActRIIa polypeptide). In the case of fusion proteins, an ActRIIa polypeptide is fused to a stabilizer domain such as an IgG molecule (e.g., an Fc domain). As used herein, the term "stabilizer domain" not only refers to a fusion domain (e.g., Fc) as in the case of fusion proteins, but also includes nonproteinaceous modifications such as a carbohydrate moiety, or nonproteinaceous polymer, such as polyethylene glycol.

In certain embodiments, the present invention makes available isolated and/or purified forms of the ActRIIa polypeptides, which are isolated from, or otherwise substantially free of, other proteins. ActRIIa polypeptides will generally be produced by expression from recombinant nucleic acids.

3. Nucleic Acids Encoding ActRIIa Polypeptides

In certain aspects, the invention provides isolated and/or recombinant nucleic acids encoding any of the ActRIIa polypeptides (e.g., soluble ActRIIa polypeptides), including fragments, functional variants and fusion proteins disclosed herein, and the use of nucleic acids to produce protein for use in decreasing FSH levels. For example, SEQ ID NO: 4 encodes the naturally occurring human ActRIIa precursor polypeptide, while SEQ ID NO: 5 encodes the processed extracellular domain of ActRIIa. The subject nucleic acids may be single-stranded or double stranded. Such nucleic acids may be DNA or RNA molecules. These nucleic acids may be used, for example, in methods for making ActRIIa polypeptides or as direct therapeutic agents (e.g., in a gene therapy approach).

In certain aspects, the subject nucleic acids encoding ActRIIa polypeptides are further understood to include nucleic acids that are variants of SEQ ID NO: 4 or 5. Variant nucleotide sequences include sequences that differ by one or more nucleotide substitutions, additions or deletions, such as allelic variants.

In certain embodiments, the invention provides for the use of isolated or recombinant nucleic acid sequences that are at least 80%, 85%, 90%, 95%, 97%, 98%, 99% or 100% identical to SEQ ID NO: 4 or 5. One of ordinary skill in the art will appreciate that nucleic acid sequences complementary to SEQ ID NO: 4 or 5, and variants of SEQ ID NO: 4 or 5 are also within the scope of this invention. In further embodiments, the nucleic acid sequences of the invention can be isolated, recombinant, and/or fused with a heterologous nucleotide sequence, or in a DNA library.

In other embodiments, proteins to be used to decrease FSH levels are encoded by nucleic acids that hybridize under highly stringent conditions to the nucleotide sequence designated in SEQ ID NO: 4 or 5, complement sequence of SEQ ID NO: 4 or 5, or fragments thereof. As discussed above, one of ordinary skill in the art will understand readily that appropriate stringency conditions which promote DNA hybridization can be varied. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6×SSC at room temperature followed by a wash at 2×SSC at room temperature.

Isolated nucleic acids which differ from the nucleic acids as set forth in SEQ ID NOs: 4 or 5 due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this invention.

In certain embodiments, the recombinant nucleic acids of the invention may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the invention. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects of the invention, the subject nucleic acid is provided in an expression vector comprising a nucleotide sequence encoding an ActRIIa polypeptide and operably linked to at least one regulatory sequence. Regulatory sequences are art-recognized and are selected to direct expression of the ActRIIa polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding an ActRIIa polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid of the invention can be produced by ligating the cloned gene, or a portion thereof, into a vector suitable for expression in either prokaryotic cells, eukaryotic cells (yeast, avian, insect or mammalian), or both. Expression vehicles for production of a recombinant ActRIIa polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as E. coli.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see *Molecular Cloning A Laboratory Manual*, 3rd Ed., ed. by Sambrook, Fritsch and Maniatis (Cold Spring Harbor Laboratory Press, 2001). In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In a preferred embodiment, a vector will be designed for production of the subject ActRIIa polypeptides in CHO cells, such as a Pcmv-Script vector (Stratagene, La Jolla, Calif.), pcDNA4 vectors (Invitrogen, Carlsbad, Calif.) and pCI-neo vectors (Promega, Madison, Wis.). As will be apparent, the subject gene constructs can be used to cause expression of the subject ActRIIa polypeptides in cells propagated in culture, e.g., to produce proteins, including fusion proteins or variant proteins, for purification.

This disclosure also pertains to a host cell transfected with a recombinant gene including a coding sequence (e.g., SEQ ID NO: 4 or 5) for one or more of the subject ActRIIa polypeptides. The host cell may be any prokaryotic or eukaryotic cell. For example, an ActRIIa polypeptide of the invention may be expressed in bacterial cells such as E. coli, insect cells (e.g., using a baculovirus expression system), yeast, or mammalian cells. Other suitable host cells are known to those skilled in the art.

Accordingly, the present invention further pertains to methods of producing the subject ActRIIa polypeptides. For example, a host cell transfected with an expression vector encoding an ActRIIa polypeptide can be cultured under appropriate conditions to allow expression of the ActRIIa polypeptide to occur. The ActRIIa polypeptide may be secreted and isolated from a mixture of cells and medium containing the ActRIIa polypeptide. Alternatively, the ActRIIa polypeptide may be retained cytoplasmically or in a membrane fraction and the cells harvested, lysed and the protein isolated. A cell culture includes host cells, media and other byproducts. Suitable media for cell culture are well known in the art. The subject ActRIIa polypeptides can be isolated from cell culture medium, host cells, or both, using techniques known in the art for purifying proteins, including ion-exchange chromatography, gel filtration chromatography, ultrafiltration, electrophoresis, immunoaffinity purification with antibodies specific for particular epitopes of the ActRIIa polypeptides and affinity purification with an agent that binds to a domain fused to the ActRIIa polypeptide (e.g., a protein A column may be used to purify an ActRIIa-Fc fusion). In a preferred embodiment, the ActRIIa polypeptide is a fusion protein containing a domain which facilitates its purification. In a preferred embodiment, purification is achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. As demonstrated herein, ActRIIa-hFc protein was purified to a purity of >98% as determined by size exclusion chromatography and >95% as determined by SDS PAGE. This level of purity was sufficient to achieve desirable effects on bone in mice and an acceptable safety profile in mice, rats and non-human primates.

In another embodiment, a fusion gene coding for a purification leader sequence, such as a poly-(His)/enterokinase cleavage site sequence at the N-terminus of the desired portion of the recombinant ActRIIa polypeptide, can allow purification of the expressed fusion protein by affinity chromatography using a $Ni^{2+}$ metal resin. The purification leader sequence can then be subsequently removed by treatment with enterokinase to provide the purified ActRIIa polypeptide (e.g., see Hochuli et al., (1987) *J. Chromatography* 411:177; and Janknecht et al., *PNAS USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

4. Alternative Activin and ActRIIa Antagonists

The data presented herein demonstrates that antagonists of activin-ActRIIa signaling can be used to decrease FSH levels. Although soluble ActRIIa polypeptides, and particularly ActrIIa-Fc, are preferred antagonists, and although such antagonists may affect FSH through a mechanism other than activin antagonism, other types of activin-ActRIIa antagonists are expected to be useful, including anti-activin (e.g., A, B, C or E) antibodies, anti-ActRIIa antibodies, antisense, RNAi or ribozyme nucleic acids that inhibit the production of ActRIIa and other inhibitors of activin or ActRIIa, particularly those that disrupt activin-ActRIIa binding.

An antibody that is specifically reactive with an ActRIIa polypeptide (e.g., a soluble ActRIIa polypeptide) and which either binds competitively to ligand with the ActRIIa polypeptide or otherwise inhibits ActRIIa-mediated signaling may be used as an antagonist of ActRIIa polypeptide activities. Likewise, an antibody that is specifically reactive with an activin A polypeptide and which disrupts ActRIIa binding may be used as an antagonist.

By using immunogens derived from an ActRIIa polypeptide or an activin polypeptide, anti-protein/anti-peptide antisera or monoclonal antibodies can be made by standard protocols (see, for example, Antibodies: A Laboratory Manual ed. by Harlow and Lane (Cold Spring Harbor Press: 1988)). A mammal, such as a mouse, a hamster or rabbit can be immunized with an immunogenic form of the ActRIIa polypeptide, an antigenic fragment which is capable of eliciting an antibody response, or a fusion protein. Techniques for conferring immunogenicity on a protein or peptide include conjugation to carriers or other techniques well known in the art. An immunogenic portion of an ActRIIa or activin polypeptide can be administered in the presence of adjuvant. The progress of immunization can be monitored by detection of antibody titers in plasma or serum. Standard ELISA or other immunoassays can be used with the immunogen as antigen to assess the levels of antibodies.

Following immunization of an animal with an antigenic preparation of an ActRIIa polypeptide, antisera can be obtained and, if desired, polyclonal antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with an ActRIIa polypeptide and monoclonal antibodies isolated from a culture comprising such hybridoma cells.

The term "antibody" as used herein is intended to include fragments thereof which are also specifically reactive with a subject polypeptide. Antibodies can be fragmented using conventional techniques and the fragments screened for utility in the same manner as described above for whole antibodies. For example, F(ab)$_2$ fragments can be generated by treating antibody with pepsin. The resulting F(ab)$_2$ fragment can be treated to reduce disulfide bridges to produce Fab fragments. The antibody of the present invention is further intended to include bispecific, single-chain, chimeric, humanized and fully human molecules having affinity for an ActRIIa or activin polypeptide conferred by at least one CDR region of the antibody. An antibody may further comprise a label attached thereto and able to be detected (e.g., the label can be a radioisotope, fluorescent compound, enzyme or enzyme co-factor).

In certain embodiments, the antibody is a recombinant antibody, which term encompasses any antibody generated in part by techniques of molecular biology, including CDR-grafted or chimeric antibodies, human or other antibodies assembled from library-selected antibody domains, single chain antibodies and single domain antibodies (e.g., human $V_H$ proteins or camelid $V_{HH}$ proteins). In certain embodiments, an antibody of the invention is a monoclonal antibody, and in certain embodiments, the invention makes available methods for generating novel antibodies. For example, a method for generating a monoclonal antibody that binds specifically to an ActRIIa polypeptide or activin polypeptide may comprise administering to a mouse an amount of an immunogenic composition comprising the antigen polypeptide effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monocolonal antibody that binds specifically to the antigen. Once obtained, a hybridoma can be propagated in a cell culture, optionally in culture conditions where the hybridoma-derived cells produce the monoclonal antibody that binds specifically to the antigen. The monoclonal antibody may be purified from the cell culture.

The adjective "specifically reactive with" as used in reference to an antibody is intended to mean, as is generally understood in the art, that the antibody is sufficiently selective between the antigen of interest (e.g., an ActRIIa polypeptide) and other antigens that are not of interest that the antibody is useful for, at minimum, detecting the presence of the antigen of interest in a particular type of biological sample. In certain methods employing the antibody, such as therapeutic applications, a higher degree of specificity in binding may be desirable. Monoclonal antibodies generally have a greater tendency (as compared to polyclonal antibodies) to discriminate effectively between the desired antigens and cross-reacting polypeptides. One characteristic that influences the specificity of an antibody:antigen interaction is the affinity of the antibody for the antigen. Although the desired specificity may be reached with a range of different affinities, generally preferred antibodies will have an affinity (a dissociation constant) of about $10^{-6}$, $10^{-7}$, $10^{-8}$, $10^{-9}$ or less. Given the extraordinarily tight binding between activin and ActRIIa, it is expected that a neutralizing anti-activin or anti-ActRIIa antibody would generally have a dissociation constant of $10^{-10}$ or less.

In addition, the techniques used to screen antibodies in order to identify a desirable antibody may influence the properties of the antibody obtained. For example, if an antibody is to be used for binding an antigen in solution, it may be desirable to test solution binding. A variety of different techniques are available for testing interaction between antibodies and antigens to identify particularly desirable antibodies. Such techniques include ELISAs, surface plasmon resonance binding assays (e.g., the Biacore™ binding assay, Biacore AB, Uppsala, Sweden), sandwich assays (e.g., the paramagnetic bead system of IGEN International, Inc., Gaithersburg, Md.), western blots, immunoprecipitation assays, and immunohistochemistry.

Examples of categories of nucleic acid compounds that are activin or ActRIIa antagonists include antisense nucleic acids, RNAi constructs and catalytic nucleic acid constructs. A nucleic acid compound may be single or double stranded. A double stranded compound may also include regions of overhang or non-complementarity, where one or the other of the strands is single stranded. A single stranded compound may include regions of self-complementarity, meaning that the compound forms a so-called "hairpin" or "stem-loop" structure, with a region of double helical structure. A nucleic acid compound may comprise a nucleotide sequence that is complementary to a region consisting of no more than 1000, no more than 500, no more than 250, no more than 100 or no more than 50, 35, 30, 25, 22, 20 or 18 nucleotides of the full-length ActRIIa nucleic acid sequence or activin βA or activin βB nucleic acid sequence. The region of complementarity will preferably be at least 8 nucleotides, and optionally at least 10 or at least 15 nucleotides, and optionally between 15 and 25 nucleotides. A region of complementarity may fall within an intron, a coding sequence or a noncoding sequence of the target transcript, such as the coding sequence portion. Generally, a nucleic acid compound will have a length of about 8 to about 500 nucleotides or base pairs in length, and optionally the length will be about 14 to about 50 nucleotides. A nucleic acid may be a DNA (particularly for use as an antisense), RNA or RNA:DNA hybrid. Any one strand may include a mixture of DNA and RNA, as well as modified forms that cannot readily be classified as either DNA or RNA. Likewise, a double stranded compound may be DNA:DNA, DNA:RNA or RNA:RNA, and any one strand may also include a mixture of DNA and RNA, as well as modified forms that cannot readily be classified as either DNA or RNA. A nucleic acid compound may include any of a variety of modifications, including one or modifications to the backbone (the sugar-phosphate portion in a natural nucleic acid, including internucleotide linkages) or the base portion (the purine or pyrimidine portion of a natural nucleic acid). An antisense nucleic acid compound will preferably have a length of about 15 to about 30 nucleotides and will often contain one or more modifications to improve characteristics such as stability in the serum, in a cell or in a place where the compound is likely to be delivered, such as the stomach in the case of orally delivered compounds and the lung for inhaled compounds. In the case of an RNAi construct, the strand complementary to the target transcript will generally be RNA or modifications thereof. The other strand may be RNA, DNA or any other variation. The duplex portion of double stranded or single stranded "hairpin" RNAi construct will preferably have a length of 18 to 40 nucleotides in length and optionally about 21 to 23 nucleotides in length, so long as it serves as a Dicer substrate. Catalytic or enzymatic nucleic acids may be ribozymes or DNA enzymes and may also contain modified forms. Nucleic acid compounds may inhibit expression of the target by about 50%, 75%, 90% or more when contacted with cells under physiological conditions and at a concentration where a nonsense or sense control has little or no effect. Preferred concentrations for testing the effect of nucleic acid compounds are 1, 5 and 10 micromolar. Nucleic acid compounds may also be tested for effects on, for example, FSH levels in vivo, FSH production by cell lines in vitro, or FSH-related disorders.

5. Screening Assays

In certain aspects, the present invention relates to the use of ActRIIa polypeptides (e.g., soluble ActRIIa polypeptides) and activin polypeptides to identify compounds (agents) which are agonist or antagonists of the activin-ActRIIa signaling pathway. Compounds identified through this screening can be tested to assess their ability to modulate the growth or survival of cancer cells, particularly prostate cancer cells, in vivo or in vitro. These compounds can be tested, for example, in animal models such as mouse xenograft models. One useful animal model is the murine LAPC-4 prostate cancer model (described in U.S. Pat. No. 7,122,714). Other animal models of prostate cancer can be generated, for example, by implanting LNCaP cells. The LNCaP cell line is an established androgen-responsive prostate cancer cell line obtained from a lymph node metastasis of a prostate cancer patient.

There are numerous approaches to screening for therapeutic agents for decreasing or inhibiting FSH secretion by targeting activin and ActRIIa signaling. In certain embodiments, high-throughput screening of compounds can be carried out to identify agents that perturb activin or ActRIIa-mediated effects on a selected cell line. In certain embodiments, the assay is carried out to screen and identify compounds that specifically inhibit or reduce binding of an ActRIIa polypeptide to activin. Alternatively, the assay can be used to identify compounds that enhance binding of an ActRIIa polypeptide to activin. In a further embodiment, the compounds can be identified by their ability to interact with an activin or ActRIIa polypeptide.

A variety of assay formats will suffice and, in light of the present disclosure, those not expressly described herein will nevertheless be comprehended by one of ordinary skill in the art. As described herein, test compounds (agents) may be created by any combinatorial chemical method. Alternatively, the subject compounds may be naturally occurring biomolecules synthesized in vivo or in vitro. Compounds (agents) to be tested for their ability to act as modulators of tissue growth can be produced, for example, by bacteria, yeast, plants or other organisms (e.g., natural products), produced chemically (e.g., small molecules, including peptidomimetics), or produced recombinantly. Test compounds contemplated herein include non-peptidyl organic molecules, peptides, polypeptides, peptidomimetics, sugars, hormones, and nucleic acid molecules. In a specific embodiment, the test agent is a small organic molecule having a molecular weight of less than about 2,000 Daltons.

Test compounds can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps. Optionally, the compounds may be optionally derivatized with other compounds and have derivatizing groups that facilitate isolation of the compounds. Non-limiting examples of derivatizing groups include biotin, fluorescein, digoxygenin, green fluorescent protein, isotopes, polyhistidine, magnetic beads, glutathione S transferase (GST), photoactivatible crosslinkers or any combinations thereof.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity or bioavailability of the test compound can be generally ignored in the in vitro system, the assay instead being focused primarily on the effect of the drug on the molecular target as may be manifest in an alteration of binding affinity between an ActRIIa polypeptide and activin.

Merely to illustrate, in an exemplary screening assay, the compound of interest is contacted with an isolated and purified ActRIIa polypeptide which is ordinarily capable of binding to activin. To the mixture of the compound and ActRIIa polypeptide is then added a composition containing an ActRIIa ligand. Detection and quantification of ActRIIa/activin complexes provides a means for determining the compound's efficacy at inhibiting (or potentiating) complex formation between the ActRIIa polypeptide and activin. The efficacy of the compound can be assessed by generating dose response curves from data obtained using various concentrations of the test compound. Moreover, a control assay can also be performed to provide a baseline for comparison. For example, in a control assay, isolated and purified activin is added to a composition containing the ActRIIa polypeptide, and the formation of ActRIIa/activin complex is quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system.

Complex formation between the ActRIIa polypeptide and activin may be detected by a variety of techniques. For instance, modulation of the formation of complexes can be quantitated using, for example, detectably labeled proteins such as radiolabeled (e.g., $^{32}P$, $^{35}S$, $^{14}C$ or $^{3}H$), fluorescently labeled (e.g., FITC), or enzymatically labeled ActRIIa polypeptide or activin, by immunoassay, or by chromatographic detection.

In certain embodiments, fluorescence polarization assays and fluorescence resonance energy transfer (FRET) assays may be used for measuring, either directly or indirectly, the degree of interaction between an ActRIIa polypeptide and its binding protein. Other suitable modes of detection include, for example, those based on optical waveguides (PCT Publication WO 96/26432 and U.S. Pat. No. 5,677,196), surface plasmon resonance (SPR), surface charge sensors, and surface force sensors.

An interaction trap assay, also known as the "two hybrid assay," may also be used for identifying agents that disrupt or potentiate interaction between an ActRIIa polypeptide and its binding protein. See for example, U.S. Pat. No. 5,283,317; Zervos et al. (1993) Cell 72:223-232; Madura et al. (1993) J Biol Chem 268:12046-12054; Bartel et al. (1993) Biotechniques 14:920-924; and Iwabuchi et al. (1993) Oncogene 8:1693-1696). In a specific embodiment, a reverse two hybrid system may be used to identify compounds (e.g., small molecules or peptides) that dissociate interactions between an ActRIIa polypeptide and its binding protein. See for example, Vidal and Legrain, (1999) Nucleic Acids Res 27:919-29; Vidal and Legrain, (1999) Trends Biotechnol 17:374-81; and U.S. Pat. Nos. 5,525,490; 5,955,280; and 5,965,368.

In certain embodiments, compounds are identified by their ability to interact with an ActRIIa or activin polypeptide described herein. The interaction between the compound and the ActRIIa or activin polypeptide may be covalent or non-covalent. For example, such interaction can be identified at the protein level using in vitro biochemical methods, including photo-crosslinking, radiolabeled ligand binding, and affinity chromatography (Jakoby W B et al., 1974, Methods in Enzymology 46: 1). In certain cases, the compounds may be screened in a mechanism based assay, such as an assay to detect compounds which bind to an activin or ActRIIa polypeptide. This may include a solid phase or fluid phase binding event. Alternatively, the gene encoding an activin or ActRIIa polypeptide can be transfected with a reporter system (e.g., β-galactosidase, luciferase, or green fluorescent protein) into a cell and screened against the library optionally by a high throughput screening or with individual members of the library. Other mechanism based binding assays may be used, for example, binding assays which detect changes in free energy. Binding assays can be performed with the target fixed to a well, bead or chip or captured by an immobilized antibody or resolved by capillary electrophoresis. The bound compounds may be detected usually using calorimetric or fluorescence or surface plasmon resonance.

6. Exemplary Therapeutic Uses

In certain embodiments, the present invention provides methods of decreasing or inhibiting FSH secretion in an individual in need thereof by administering to the individual a therapeutically effective amount of an activin-ActRIIa antagonist, such as, for example, an ActRIIa polypeptide. Methods of decreasing or inhibiting FSH secretion include all methods which lead to said effect, including, for example, decreasing FSH transcription, translation, post-translational processing, and secretion. Various kits are available for testing plasma FSH levels, including MENOCHECK™. Normal values for FSH in men range from 2-18 mIU/ml of blood. Normal values for women range from 5 and 25 mIU/mL. Levels higher than 50 mIU/mL in healthy women are associated with menopause. The tissue concentration of FSH can be determined by testing saliva (eMHP™).

In certain embodiments, the present invention provides methods of treating or preventing prostate cancer in an individual in need thereof by administering to the individual a therapeutically effective amount of an activin-ActRIIa antagonist, such as, for example, an ActRIIa polypeptide in order to decrease or inhibit FSH secretion. These methods may be used for therapeutic as well as prophylactic treatment of humans, particularly males, who have a high risk for developing prostate cancer. As every man is at risk for developing prostate cancer, a man with a high risk for developing prostate cancer is a man whose risk factors confer a greater probability of developing the disease compared to the general population or the population of men within a certain age group. Exemplary risk factors include age, family history or genetic makeup, lifestyle habits such as exercise and diet, and exposure to radiation or other cancer-causing agents.

As used herein, a therapeutic that "prevents" a disorder or condition refers to a compound that, in a statistical sample, reduces the occurrence of the disorder or condition in the treated sample relative to an untreated control sample, or delays the onset of one or more symptoms or characteristics of the disorder or condition relative to the untreated control sample. For example, preventing prostate cancer may refer to the absence of new lesions following treatment, or the absence or delay of metastatic disease.

The term "treating prostate cancer" refers to an improvement of one or more symptoms or characteristics of the disease relative to an untreated control or relative to the severity of disease prior to treatment. The term does not necessarily require that the patient receiving the treatment be cured or that the disease be completely eradicated from the patient. An agent that treats prostate cancer may be an agent that reduces the severity of one or more symptoms or characteristics of the disease. It should be noted that tumor growth and progression is influenced by a variety of factors, including mediators of cell cycle progression and cell division and regulators of cell death, or apoptosis. Accordingly, treating prostate cancer may involve a decrease in cancer cell proliferation or a decrease in the rate of cell division. Alternatively or additionally, treating prostate cancer may involve a decrease in cancer cell survival or an increase in apoptosis. Accordingly, in certain embodiments, treating prostate cancer may involve both a decrease in cell division and an increase in cell death. Regardless of mechanism, the effectiveness of an agent in treating prostate cancer may be determined by observable metrics, such as a lower number of cancer cells compared to a control (either due to decreased proliferation, increased apoptosis, or both), or a decrease in tumor size compared to a control. Therefore treating prostate cancer or inhibiting tumor or cancer cell growth is intended to be neutral as to the mechanism by which such a change occurs. Both prevention and treatment may be discerned in the diagnosis provided by a physician or other health care provider and the analysis of the intended result of administration of the therapeutic agent.

When observing the effects of the subject antagonists on prostate cancer progression in humans, an effect may be evaluated by a decrease or disappearance of measurable disease, and/or the absence of new lesions or the prevention of metastases. For example, activin-ActRIIa antagonists may significantly reduce or delay prostate cancer progression in patients with both noninvasive and invasive prostate cancer. In addition, the antagonists may prevent or reduce the risk of developing prostate cancer in healthy men with risk factors for the disease. The antagonists may also reduce the risk of prostate cancer recurrence in patients with a history of the disease.

Accordingly, activin-ActRIIa antagonists may be used to prevent or delay the onset of prostate cancer in individuals considered to be at risk for developing the disease, and such antagonists may be used in selected patient populations. Examples of appropriate patient populations include patients with a family history of prostate cancer, such as male patients where a father or brother has been diagnosed with the disease. In one embodiment, a patient considered to be at high risk for developing prostate cancer but who has not been diagnosed with the disease is treated with an activin-ActRIIa antagonist. Such treatment may begin when the patient reaches the age of 30, 40, 50, 60, or 70.

Activin-ActRIIa antagonists disclosed herein, and particularly ActRIIa-Fc proteins, may be used to treat or prevent prostate cancer in a patient, including patients with solid tumors as well as patients with metastatic cancer. Activin-ActRIIa antagonists may also be administered to human subjects with precancerous or benign lesions of the prostate or with any abnormal proliferative lesions including typical hyperplasia, atypical hyperplasia, and noninvasive or in situ carcinoma. The antagonists of the present disclosure are also useful in the treatment or prevention of both hormone-dependent or hormone-responsive cancers and hormone-independent cancers (e.g., hormone-refractory prostate cancer). Activin-ActRIIa antagonists may prove to be particularly useful in tumors that express elevated (relative to normal prostate tissue-derived cells) levels of activin (e.g., A, AB or B) or elevated levels of ActRIIa or ActRIIb.

In certain embodiments, the present invention provides methods of decreasing or inhibiting FSH secretion in an individual afflicted with an FSH-secreting pituitary tumor by administering to the individual a therapeutically effective amount of an activin-ActRIIa antagonist, such as, for example, an ActRIIa polypeptide. Inhibiting the hyper-secretion of FSH in these pituitary tumors is useful as a treatment to reduce the tumor symptoms, such as increased estrogen levels and the development of ovarian cysts. The present methods are preferably used in conjunction with conventional cancer therapies, such as surgery, however, the inhibition of FSH secretion alone may be an effective treatment, especially in cases where surgery or radiation is contraindicated.

The present invention recognizes that the effectiveness of conventional cancer therapies (e.g., chemotherapy, radiation therapy, phototherapy, immunotherapy, and surgery, in particular prostatectomy) can be enhanced through the use of the subject antagonists. Accordingly, activin-ActRIIa antagonists may be used in combination therapies for the treatment, prevention, or management of prostate cancer. The antagonists may be administered to patients in combination with radiation and/or surgical treatment as well as with cytotoxic chemotherapy and/or endocrine therapies. Such combination treatments may work synergistically and allow reduction of dosage of each of the individual treatments, thereby reducing the detrimental side effects exerted by each treatment at higher dosages. In other instances, malignancies that are refractory to a treatment may respond to a combination therapy of two or more different treatments. Accordingly, the disclosure relates to the administration of an activin-ActRIIa antagonist in combination with another conventional anti-neoplastic agent, either concomitantly or sequentially, in order to enhance the therapeutic effect of the anti-neoplastic agent or overcome cellular resistance to such anti-neoplastic agent. The disclosure also relates to the administration of an activin-ActRIIa antagonist in combination with hormonal therapy. Activin-ActRIIa antagonists may also be used in combination therapies to reduce the symptoms arising from FSH secreting pituitary tumors. Pharmaceutical compounds that may be used for combinatory anti-tumor therapy include, merely to illustrate: aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic anti-tumor compounds may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; and chromatin disruptors.

In certain embodiments, pharmaceutical compounds that may be used for combinatory therapy include anti-angiogenesis agents such as (1) inhibitors of release of "angiogenic molecules," such as bFGF (basic fibroblast growth factor); (2) neutralizers of angiogenic molecules, such as an anti-βbFGF antibodies; and (3) inhibitors of endothelial cell response to angiogenic stimuli, including collagenase inhibitor, basement membrane turnover inhibitors, angiostatic steroids, fungal-derived angiogenesis inhibitors, platelet factor 4, thrombospondin, arthritis drugs such as D-penicillamine and gold thiomalate, vitamin D3 analogs, alpha-interferon, and the like. For additional proposed inhibitors of angiogenesis, see Blood et al., Bioch. Biophys. Acta., 1032:89-118 (1990), Moses et al., Science, 248:1408-1410 (1990), Ingber et al., Lab. Invest., 59:44-51 (1988), and U.S. Pat. Nos. 5,092,885, 5,112,946, 5,192,744, 5,202,352, and 6573256. In addition, there are a wide variety of compounds that can be used to inhibit angiogenesis, for example, peptides or agents that block the VEGF-mediated angiogenesis pathway, endostatin protein or derivatives, lysine binding fragments of angiostatin, melanin or melanin-promoting compounds, plasminogen fragments (e.g., Kringles 1-3 of plasminogen), tropoin subunits, antagonists of vitronectin αvβ3, peptides derived from Saposin B, antibiotics or analogs (e.g., tetracycline, or neomycin), dienogest-containing compositions, compounds comprising a MetAP-2 inhibitory core coupled to a peptide, the compound EM-138, chalcone and its analogs, and naaladase inhibitors. See, for example, U.S. Pat. Nos. 6,395,718, 6,462,075, 6,465,431, 6,475,784, 6,482,802, 6,482,810, 6,500,431, 6,500,924, 6,518,298, 6,521,439, 6,525,019, 6,538,103, 6,544,758, 6,544,947, 6,548,477, 6,559,126, and 6,569,845.

Depending on the nature of the combinatory therapy, administration of the therapeutic antagonists of the invention may be continued while the other therapy is being administered and/or thereafter. Administration of the antagonists described herein may be made in a single dose, or in multiple doses. In some instances, administration of the antagonists is commenced at least several days prior to the conventional therapy, while in other instances, administration is begun either immediately before or at the time of the administration of the conventional therapy.

One aspect of the application provides for methods and compositions useful in fertility. Decreasing or inhibiting FSH secretion through the administration of an activin-ActRIIa antagonist is a useful method to inhibit sperm maturation. In females, a decrease of FSH acts to limit proliferation of follicular granulosa cells in the ovary. Decreasing or inhibiting FSH secretion through the administration of an activin-ActRIIa antagonist is a useful method of contraception. Reduced FSH may also delay the maturation of follicles within the ovary, thereby postponing the maturation of a limited number of follicles in women. Such treatments have the potential for increasing the possibility of natural fertilization and pregnancy later in life. Delaying maturation of follicles within the ovary by decreasing FSH secretion is also useful in preventing the depletion of oocytes, a common side effect of chemotherapy or similar treatments designed to treat rapidly dividing cells.

The present application also provides for novel compositions comprising one or more activin-ActRIIa antagonists in combination with one or more contraceptive agents. Exemplary contraceptive agents include estrogen, progestogen, progestin (e.g., norethynodrel, norethindrone, norgestimate, norgestrel, levonorgestrel, medroxyprogesteroneand desogestrel), Ormeloxifene (Centchroman)

In certain embodiments, the present invention provides methods of treating or preventing estrogen related disorders in an individual in need thereof by administering to the individual a therapeutically effective amount of an activin-ActRIIa antagonist, such as, for example, an ActRIIa polypeptide in order to decrease or inhibit FSH secretion. Because of the controlling function of FSH on estrogen synthesis, the reduction of FSH secretion may also be effective in the treatment of estrogen related disorders such as uterine fibroids, endometriosis, polycystic ovarian disease, dysfunctional uterine bleeding, and ovarian cancer.

7. Pharmaceutical Compositions

In certain embodiments, activin-ActRIIa antagonists (e.g., ActRIIa polypeptides) of the present invention are formulated with a pharmaceutically acceptable carrier. For example, an ActRIIa polypeptide can be administered alone or as a component of a pharmaceutical formulation (therapeutic composition). The subject compounds may be formulated for administration in any convenient way for use in human or veterinary medicine.

In certain embodiments, the therapeutic method of the invention includes administering the composition systemically, or locally as an implant or device. When administered, the therapeutic composition for use in this invention is in a pyrogen-free, physiologically acceptable form. Therapeutically useful agents other than the ActRIIa antagonists which may also optionally be included in the composition as described above, may be administered simultaneously or sequentially with the subject compounds (e.g., ActRIIa polypeptides) in the methods of the invention.

Typically, ActRIIa antagonists will be administered parentally, and particularly intravenously or subcutaneously. Pharmaceutical compositions suitable for parenteral administration may comprise one or more ActRIIa polypeptides in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

In certain embodiments, methods of the invention can be administered for orally, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an agent as an active ingredient. An agent may also be administered as a bolus, electuary or paste.

In solid dosage forms for oral administration (capsules, tablets, pills, dragees, powders, granules, and the like), one or more therapeutic compounds of the present invention may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

The compositions of the invention may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

It is understood that the dosage regimen will be determined by the attending physician considering various factors which modify the action of the subject compounds of the invention (e.g., ActRIIa polypeptides). The various factors include, but are not limited to, degree of reduction in FSH levels desired, the severity of disease, the patient's age, sex, and diet, the severity of any disease that may be contributing to bone loss, time of administration, and other clinical factors. The addition of other known growth factors to the final composition, may also affect the dosage. Progress can be monitored by periodic assessment of FSH levels or other symptoms associated with the FSH-related disorder to be treated.

Experiments with primates and humans have demonstrated that effects of ActRIIa-Fc on FSH are detectable when the compound is dosed at intervals and amounts sufficient to achieve serum concentrations of about 1000 ng/ml, with significant effects on FSH occurring at a dosage of 0.3 mg/kg or the equivalent in terms of area-under-curve. In humans, serum levels of 1000 ng/ml may be achieved with a single dose of 0.3 mg/kg or greater. The observed serum half-life of the molecule is between about 25 and 35 days, substantially longer than most Fc fusion proteins, and thus a sustained effective serum level may be achieved, for example, by dosing with about 0.05 to 0.5 mg/kg on a weekly or biweekly basis, or higher doses may be used with longer intervals between dosings. For example, doses of 0.1, 0.3, 0.5, 0.7, 1, 2 or 3 mg/kg, or values in between, might be used on a monthly or bimonthly basis, and the effect on bone may be sufficiently durable that dosing is necessary only once every 3, 4, 5, 6, 9, 12 or more months. Longer intervals between doses are further supported by the duration of the pharmacodynamic effect, which is longer than the duration of drug in the serum. PD effects are observed for at least 120 days in human patients.

In certain embodiments, the present invention also provides gene therapy for the in vivo production of ActRIIa polypeptides. Such therapy would achieve its therapeutic effect by introduction of the ActRIIa polynucleotide sequences into cells or tissues having the disorders as listed above. Delivery of ActRIIa polynucleotide sequences can be achieved using a recombinant expression vector such as a chimeric virus or a colloidal dispersion system. Preferred for therapeutic delivery of ActRIIa polynucleotide sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing the ActRIIa polynucleotide. In a preferred embodiment, the vector is targeted to bone or cartilage.

Alternatively, tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for ActRIIa polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. RNA, DNA and intact virions can be encapsulated within the aqueous interior and be delivered to cells in a biologically active form (see e.g., Fraley, et al., Trends Biochem. Sci., 6:77, 1981). Methods for efficient gene transfer using a liposome vehicle, are known in the art, see e.g., Mannino, et al., Biotechniques, 6:682, 1988. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Illustrative phospholipids include egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

EXEMPLIFICATION

The invention now being generally described, it will be more readily understood by reference to the following examples, which are included merely for purposes of illustration of certain embodiments and embodiments of the present invention, and are not intended to limit the invention.

Example 1

ActRIIa-Fc Fusion Proteins

Applicants constructed a soluble ActRIIa fusion protein that has the extracellular domain of human ActRIIa fused to a human or mouse Fc domain with a minimal linker in between. The constructs are referred to as ActRIIa-hFc and ActRIIa-mFc, respectively.

ActRIIa-hFc is shown below as purified from CHO cell lines (SEQ ID NO: 7):

```
ILGRSETQECLFFNANWEKDRTNQTGVEPCYGDKDKRRHCFATWKNISGS
IEIVKQGCWLDDINCYDRTDCVEKKDSPEVYFCCCEGNMCNEKFSYFPEM
EVTQPTSNPVTPKPPTGGGTHTCPPCPAPELLGGPSVFLFPPKPKDTLMI
SRTPEVTCVVVDVSHEDPEVKFNWYVDGVEVHNAKTKPREEQYNSTYRVV
SVLTVLHQDWLNGKEYKCKVSNKALPVPIEKTISKAKGQPREPQVYTLPP
SREEMTKNQVSLTCLVKGFYPSDIAVEWESNGQPENNYKTTPPVLDSDGS
FFLYSKLTVDKSRWQQGNVFSCSVMHEALHNHYTQKSLSLSPGK
```

The ActRIIa-hFc and ActRIIa-mFc proteins were expressed in CHO cell lines. Three different leader sequences were considered:

```
(i) Honey bee mellitin (HBML):
MKFLVNVALVFMVVYISYIYA        (SEQ ID NO: 8)

(ii) Tissue Plasminogen Activator (TPA):
MDAMKRGLCCVLLLCGAVFVSP       (SEQ ID NO: 9)

(iii) Native:
MGAAAKLAFAVFLISCSSGA.        (SEQ ID NO: 10)
```

The selected form employs the TPA leader and has the following unprocessed amino acid sequence:

```
                                        (SEQ ID NO:13)
MDAMKRGLCCVLLLCGAVFVSPGAAILGRSETQECLFFNANWEKDRTNQT
GVEPCYGDKDKRRHCFATWKNISGSIEIVKQGCWLDDINCYDRTDCVEKK
DSPEVYFCCCEGNMCNEKFSYFPEMEVTQPTSNPVTPKPPTGGGTHTCPP
CPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKAL
PVPIEKTISKAKGQPREPQVYTLPPSREEMTKNQVSLTCLVKGFYPSDIA
VEWESNGQPENNYKTTPPVLDSDGSFFLYSKLTVDKSRWQQGNVFSCSVM
HEALHNHYTQKSLSLSPGK
```

This polypeptide is encoded by the following nucleic acid sequence:

```
                                        (SEQ ID NO:14)
ATGGATGCAATGAAGAGAGGGCTCTGCTGTGTGCTGCTGCTGTGTGGAGC
AGTCTTCGTTTCGCCCGGCGCCGCTATACTTGGTAGATCAGAAACTCAGG
AGTGTCTTTTTTTAATGCTAATTGGGAAAAAGACAGAACCAATCAAACTG
GTGTTGAACCGTGTTATGGTGACAAAGATAAACGGCGGCATTGTTTTGCT
ACCTGGAAGAATATTTCTGGTTCCATTGAATAGTGAAACAAGGTTGTTGG
CTGGATGATATCAACTGCTATGACAGGACTGATTGTGTAGAAAAAAAAGA
CAGCCCTGAAGTATATTTCTGTTGCTGTGAGGGCAATATGTGTAATGAAA
AGTTTTCTTATTTTCCGGAGATGGAAGTCACACAGCCCACTTCAAATCCA
GTTACACCTAAGCCACCCACCGGTGGTGGAACTCACACATGCCCACCGTG
CCCAGCACCTGAACTCCTGGGGGGACCGTCAGTCTTCCTCTTCCCCCCAA
AACCCAAGGACACCCTCATGATCTCCCGGACCCCTGAGGTCACATGCGTG
```

-continued

```
GTGGTGGACGTGAGCCACGAAGACCCTGAGGTCAAGTTCAACTGGTACGT

GGACGGCGTGGAGGTGCATAATGCCAAGACAAAGCCGCGGGAGGAGCAGT

ACAACAGCACGTACCGTGTGGTCAGCGTCCTCACCGTCCTGCACCAGGAC

TGGCTGAATGGCAAGGAGTACAAGTGCAAGGTCTCCAACAAAGCCCTCCC

AGTCCCCATCGAGAAACCATCTCCAAAGCCAAAGGGCAGCCCCGAGAAC

CACAGGTGTACACCCTGCCCCCATCCCGGGAGGAGATGACCAAGAACCAG

GTCAGCCTGACCTGCCTGGTCAAAGGCTTCTATCCCAGCGACATCGCCGT

GGAGTGGGAGAGCAATGGGCAGCCGGAGAACAACTACAAGACCACGCCTC

CCGTGCTGGACTCCGACGGCTCCTTCTTCCTCTATAGCAAGCTCACCGTG

GACAAGAGCAGGTGGCAGCAGGGGAACGTCTTCTCATGCTCCGTGATGCA

TGAGGCTCTGCACAACCACTACACGCAGAAGAGCCTCTCCCTGTCTCCGG

GTAAATGAGAATTC
```

Both ActRIIa-hFc and ActRIIa-mFc were remarkably amenable to recombinant expression. As shown in FIG. 1, the protein was purified as a single, well-defined peak of protein. N-terminal sequencing revealed a single sequence of -IL-GRSETQE (SEQ ID NO: 11). Purification could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. The ActRIIa-hFc protein was purified to a purity of >98% as determined by size exclusion chromatography and >95% as determined by SDS PAGE.

ActRIIa-hFc and ActRIIa-mFc showed a high affinity for ligands, particularly activin A. GDF-11 or Activin A ("ActA") were immobilized on a Biacore CM5 chip using standard amine coupling procedure. ActRIIa-hFc and ActRIIa-mFc proteins were loaded onto the system, and binding was measured. ActRIIa-hFc bound to activin with a dissociation constant ($K_D$) of $5 \times 10^{-12}$, and the protein bound to GDF11 with a $K_D$ of $9.96 \times 10^{-9}$. See FIG. 2. ActRIIa-mFc behaved similarly.

Figure 3:
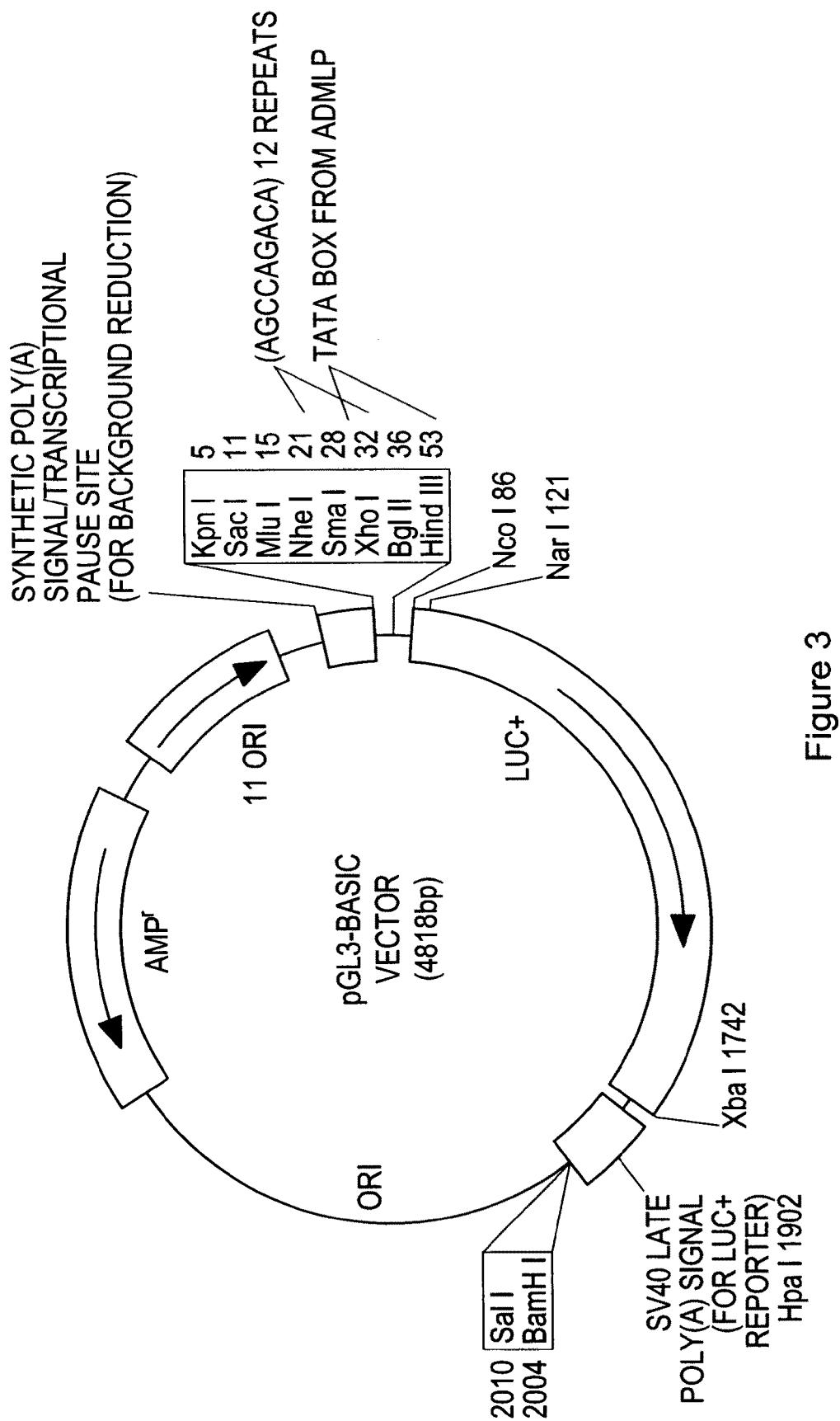
FIG. 3 shows a schematic for the A-204 Reporter Gene Assay. The figure shows the Reporter vector: pGL3(CAGA)12 (described in Dennler et al, 1998, EMBO 17: 3091-3100.) The CAGA12 motif is present in TGF-Beta responsive genes (PAI-1 gene), so this vector is of general use for factors signaling through Smad 2 and 3.

An A-204 Reporter Gene Assay was used to evaluate the effects of ActRIIa-hFc proteins on signaling by GDF-11 and Activin A. Cell line: Human Rhabdomyosarcoma (derived from muscle). Reporter vector: pGL3(CAGA)12 (Described in Dennler et al, 1998, EMBO 17: 3091-3100.) See FIG. 3. The CAGA12 motif is present in TGF-Beta responsive genes (PAI-1 gene), so this vector is of general use for factors signaling through Smad2 and 3.

Day 1: Split A-204 cells into 48-well plate.
Day 2: A-204 cells transfected with 10 µg pGL3(CAGA)12 or pGL3(CAGA)12 (10 µg)+pRLCMV (1 µg) and Fugene.
Day 3: Add factors (diluted into medium+0.1% BSA). Inhibitors need to be preincubated with Factors for 1 hr before adding to cells. 6 hrs later, cells rinsed with PBS, and lyse cells.

This is followed by a Luciferase assay. Typically in this assay, in the absence of any inhibitors, Activin A shows roughly 10 fold stimulation of reporter gene expression and an ED50 ~2 ng/ml. GDF-11: 16 fold stimulation, ED50: ~1.5 ng/ml. GDF-8 shows an effect similar to GDF-11.

Figure 4:
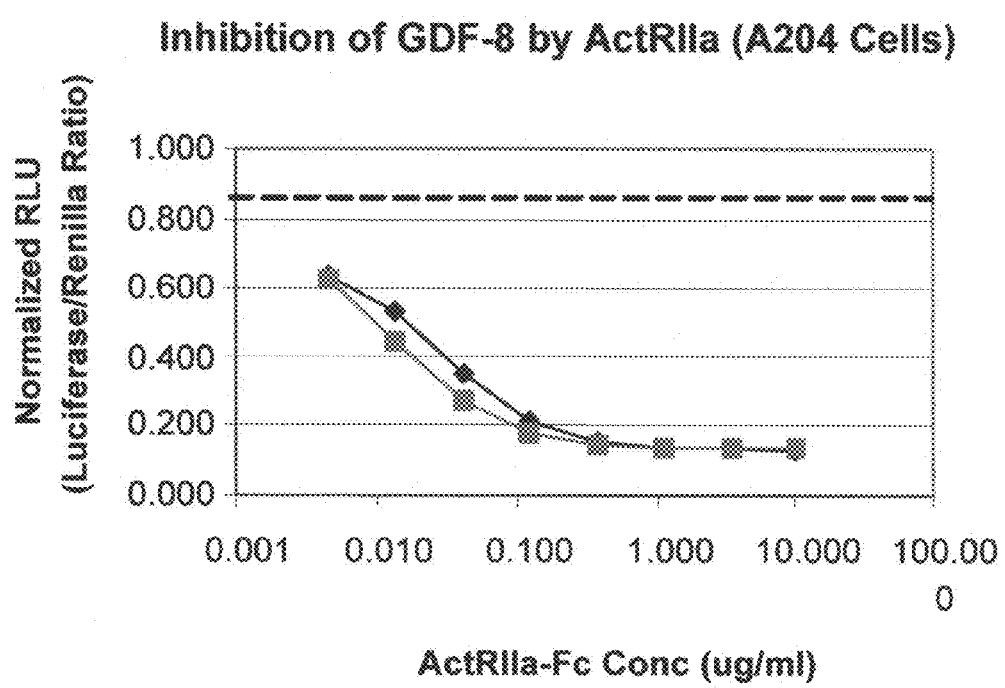
FIG. 4 shows the effects of ActRIIa-hFc (diamonds) and ActRIIa-mFc (squares) on GDF-8 signaling in the A-204 Reporter Gene Assay. Both proteins exhibited substantial inhibition of GDF-8 mediated signaling at picomolar concentrations.
Figure 5:
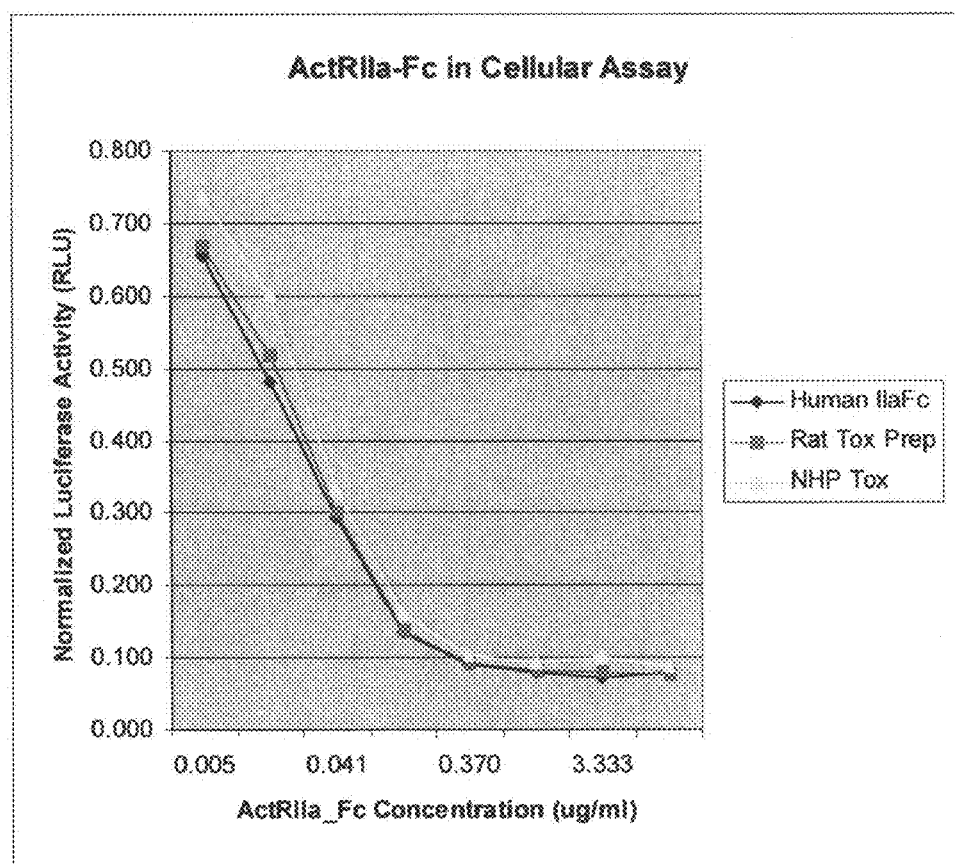
FIG. 5 shows the effects of three different preparations of ActRIIa-hFc on GDF-11 signaling in the A-204 Reporter Gene Assay.

As shown in FIG. 4, ActRIIa-hFc and ActRIIa-mFc inhibit GDF-8 mediated signaling at picomolar concentrations. As shown in FIG. 5, three different preparations of ActRIIa-hFc inhibited GDF-11 signaling with an IC50 of approximately 200 pM.

The ActRIIa-hFc was very stable in pharmacokinetic studies. Rats were dosed with 1 mg/kg, 3 mg/kg or 10 mg/kg of ActRIIa-hFc protein and plasma levels of the protein were measured at 24, 48, 72, 144 and 168 hours. In a separate study, rats were dosed at 1 mg/kg, 10 mg/kg or 30 mg/kg. In rats, ActRIIa-hFc had an 11-14 day serum half life and circulating levels of the drug were quite high after two weeks (11 µg/ml, 110 µg/ml or 304 µg/ml for initial administrations of 1 mg/kg, 10 mg/kg or 30 mg/kg, respectively.) In cynomolgus monkeys, the plasma half life was substantially greater than 14 days and circulating levels of the drug were 25 µg/ml, 304 µg/ml or 1440 µg/ml for initial administrations of 1 mg/kg, 10 mg/kg or 30 mg/kg, respectively. Preliminary results in humans suggests that the serum half life is between about 20 and 30 days.

Example 2

ActRIIa-mFc Promotes Bone Growth In Vivo

Figure 6:
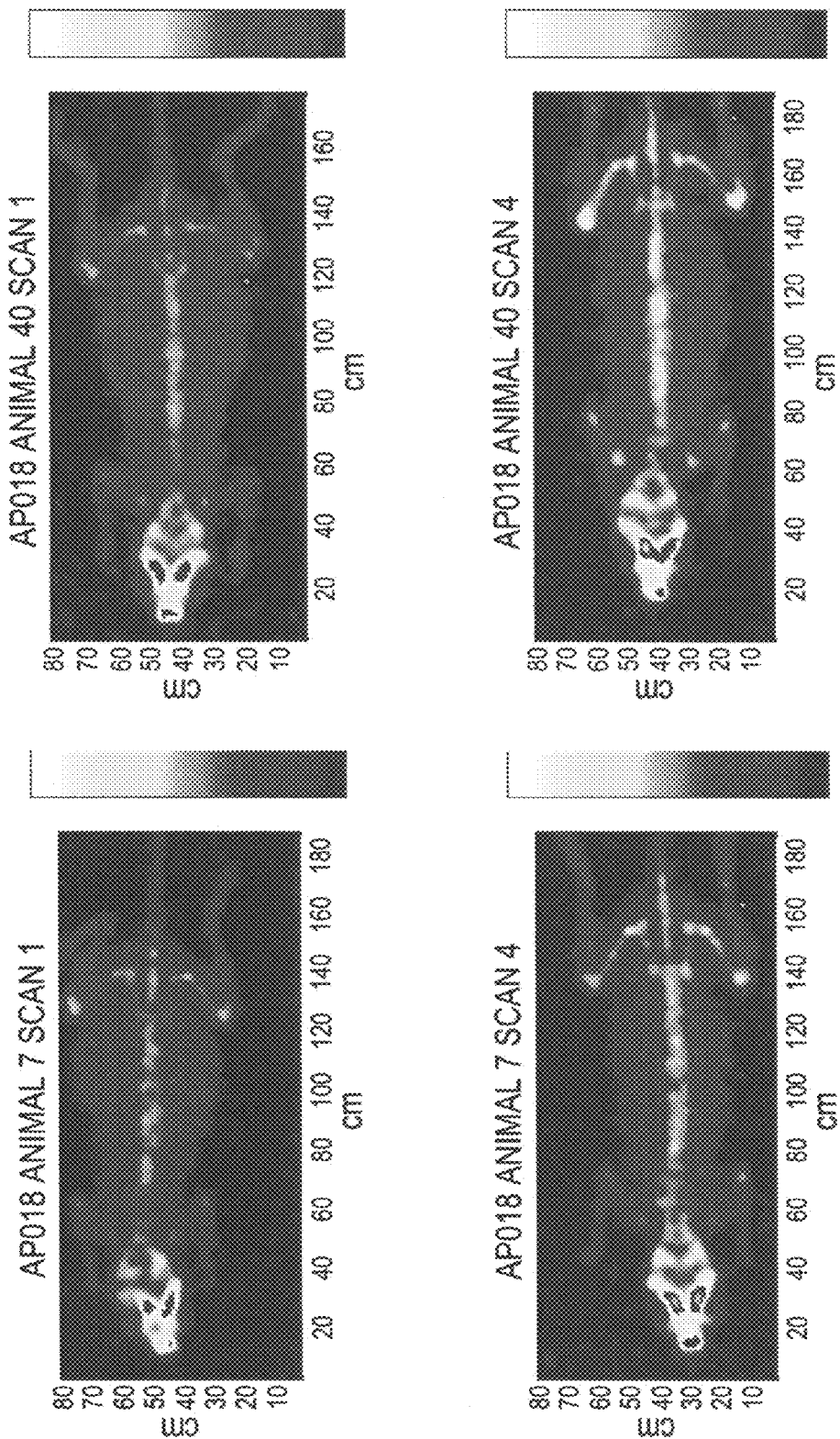
FIG. 6 shows examples of DEXA images of control- and ActRIIa-mFc-treated BALB/c mice, before (top panels) and after (bottom panels) the 12-week treatment period. Paler shading indicates increased bone density.

Normal female mice (BALB/c) were dosed with ActRIIa-mFc at a level of 1 mg/kg/dose, 3 mg/kg/dose or 10 mg/kg/dose, with doses given twice weekly. Bone mineral density and bone mineral content were determined by DEXA, see FIG. 6.

Figure 7:
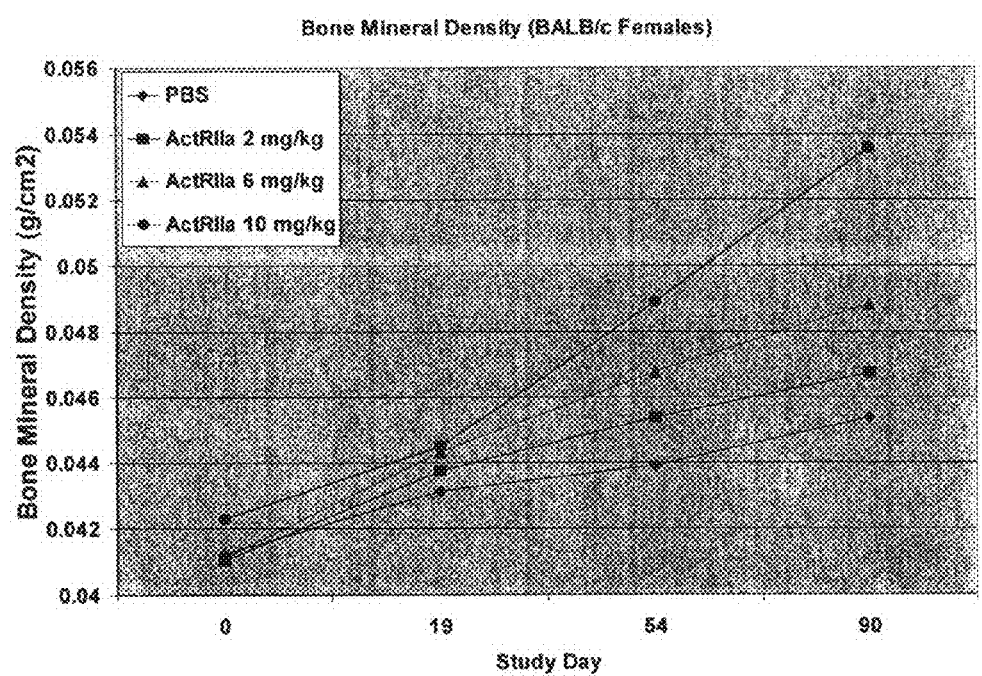
FIG. 7 shows a quantification of the effects of ActRIIa-mFc on bone mineral density in BALB/c mice over the 12-week period. Treatments were control (diamonds), 2 mg/kg dosing of ActRIIa-mFc (squares), 6 mg/kg dosing of ActRIIa-mFc (triangles) and 10 mg/kg dosing of ActRIIa-mFc (circles).
Figure 8:
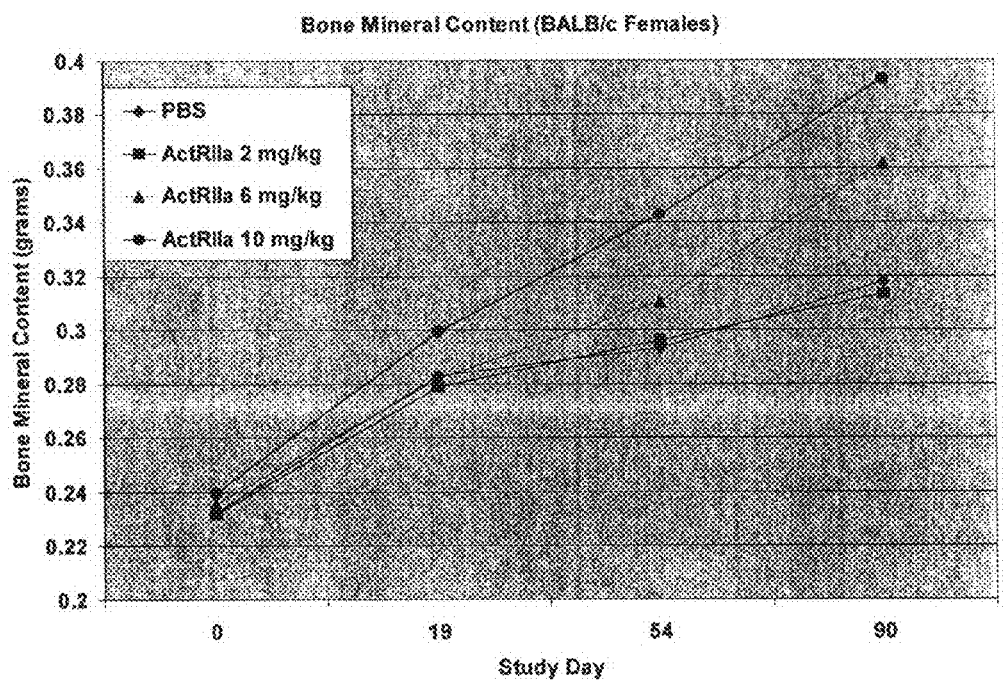
FIG. 8 shows a quantification of the effects of ActRIIa-mFc on bone mineral content in BALB/c mice over the 12-week period. Treatments were control (diamonds), 2 mg/kg dosing of ActRIIa-mFc (squares), 6 mg/kg dosing of ActRIIa-mFc (triangles) and 10 mg/kg dosing of ActRIIa-mFc (circles).

In BALB/c female mice, DEXA scans showed a significant increase (>20%) in bone mineral density and content as a result of ActRIIa-mFc treatment. See FIGS. 7 and 8.

Thus, antagonism of ActRIIa caused increased bone density and content in normal female mice. As a next step, the effect of ActRIIa-mFc on bone in a mouse model for osteoporosis was tested.

Andersson et al. (2001), established that ovariectomized mice suffered substantial bone loss (rougly 50% loss of trabecular bone six weeks post-operation), and that bone loss in these mice could be corrected with candidate therapeutic agents, such as parathyroid hormone.

Applicants used C57BL6 female mice that were ovariectomized (OVX) or sham operated at 4-5 weeks of age. Eight weeks after surgery, treatment with ActRIIa-mFc (10 mg/kg, twice weekly) or control (PBS) was initiated. Bone density was measured by CT scanner.

Figure 9:
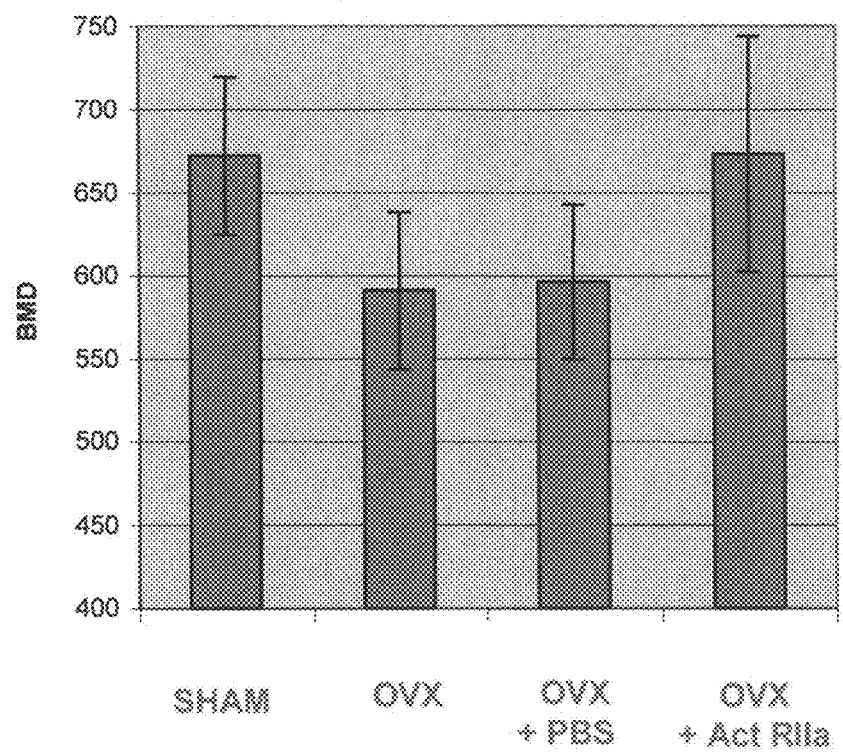
FIG. 9 shows a quantification of the effects of ActRIIa-mFc on bone mineral density of the trabecular bone in ovariectomized (OVX) or sham operated (SHAM) C57BL6 mice over after a 6-week period. Treatments were control (PBS) or 10 mg/kg dosing of ActRIIa-mFc (ActRIIa).
Figure 10:
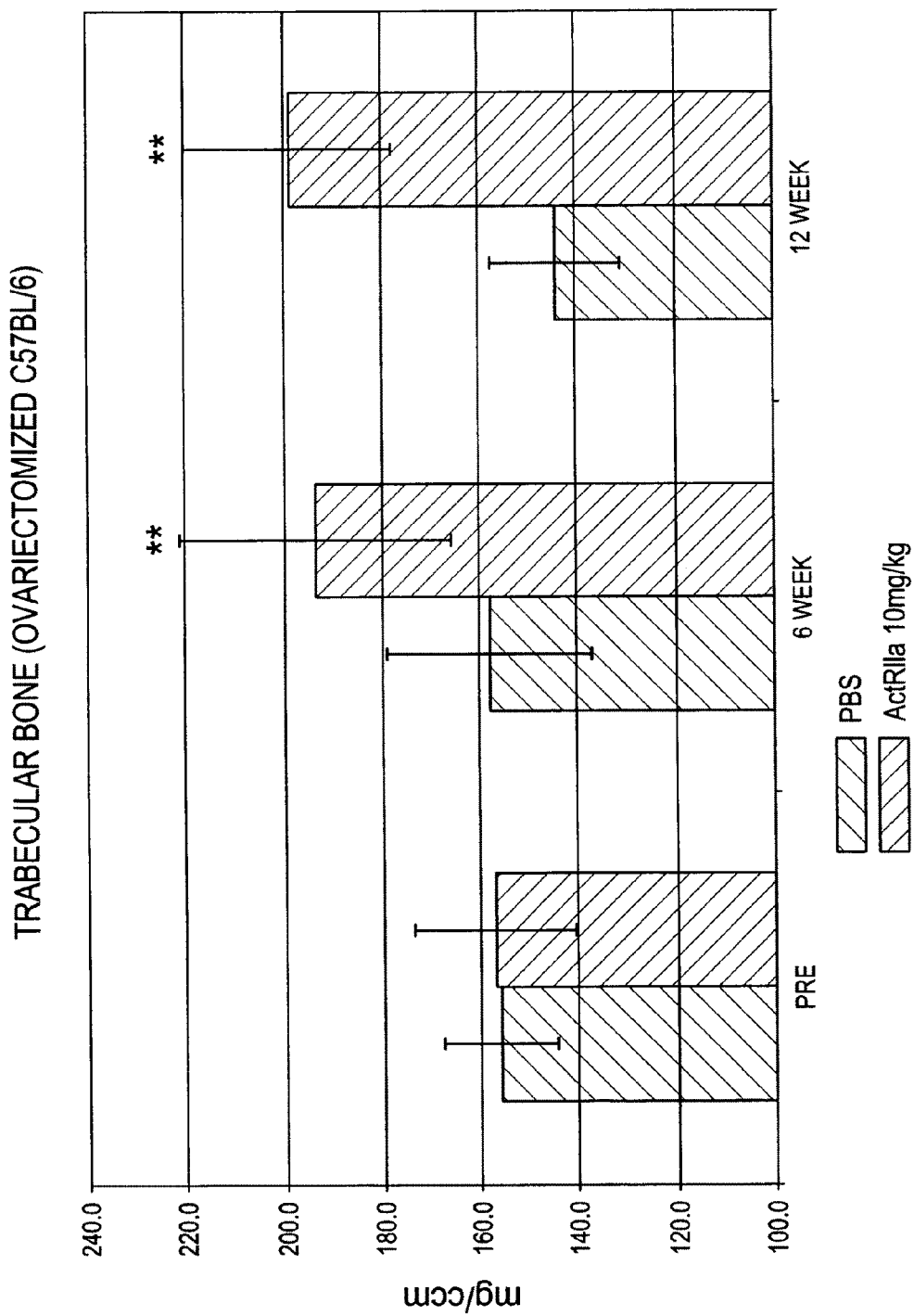
FIG. 10 shows a quantification of the effects of ActRIIa-mFc on the trabecular bone in ovariectomized (OVX) C57BL6 mice over a 12-week period. Treatments were control (PBS; pale bars) or 10 mg/kg dosing of ActRIIa-mFc (ActRIIa; dark bars).
Figure 11:
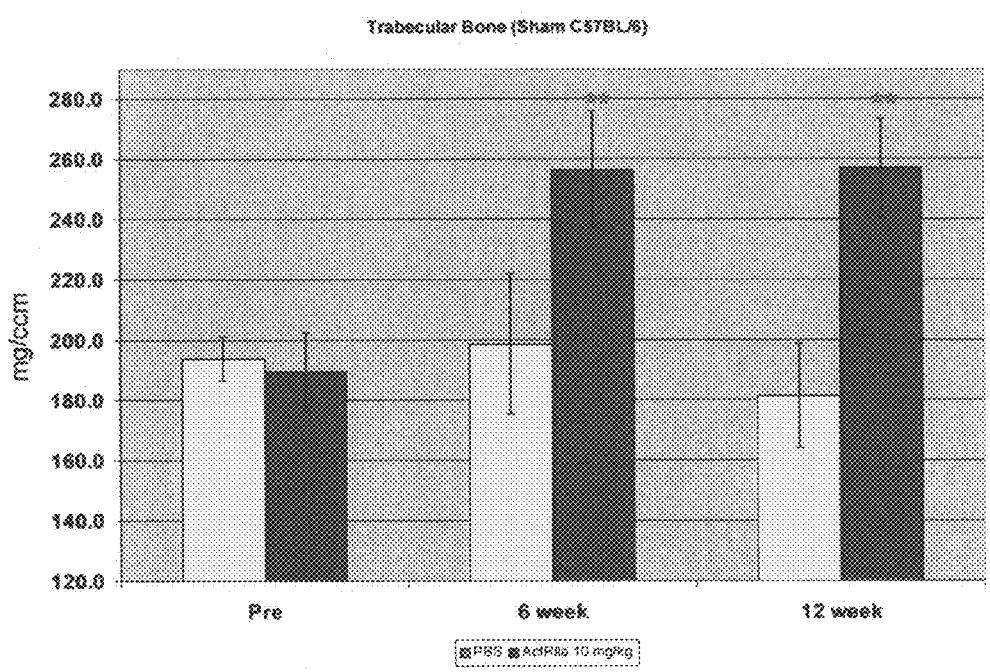
FIG. 11 shows a quantification of the effects of ActRIIa-mFc on the trabecular bone in sham operated C57BL6 mice after 6 or 12 weeks of treatment period. Treatments were control (PBS; pale bars) or 10 mg/kg dosing of ActRIIa-mFc (ActRIIa; dark bars).

As shown in FIG. 9, untreated, ovariectomized mice showed substantial loss of trabecular bone density relative to the sham controls after six weeks. ActRIIa-mFc treatment restored bone density to the level of the sham operated mice. At 6 and 12 weeks of the treatment, ActRIIa-mFc caused substantial increase in trabecular bone of OVX mice. See FIG. 10. After 6 weeks of treatment, bone density increased by 24% relative to PBS controls. After 12 weeks, the increase was 27%.

In the sham operated mice, ActRIIa-mFc also caused a substantial increase in trabecular bone. See FIG. 1. After 6 and 12 weeks, the treatment produced a 35% increase relative to controls.

Figure 12:
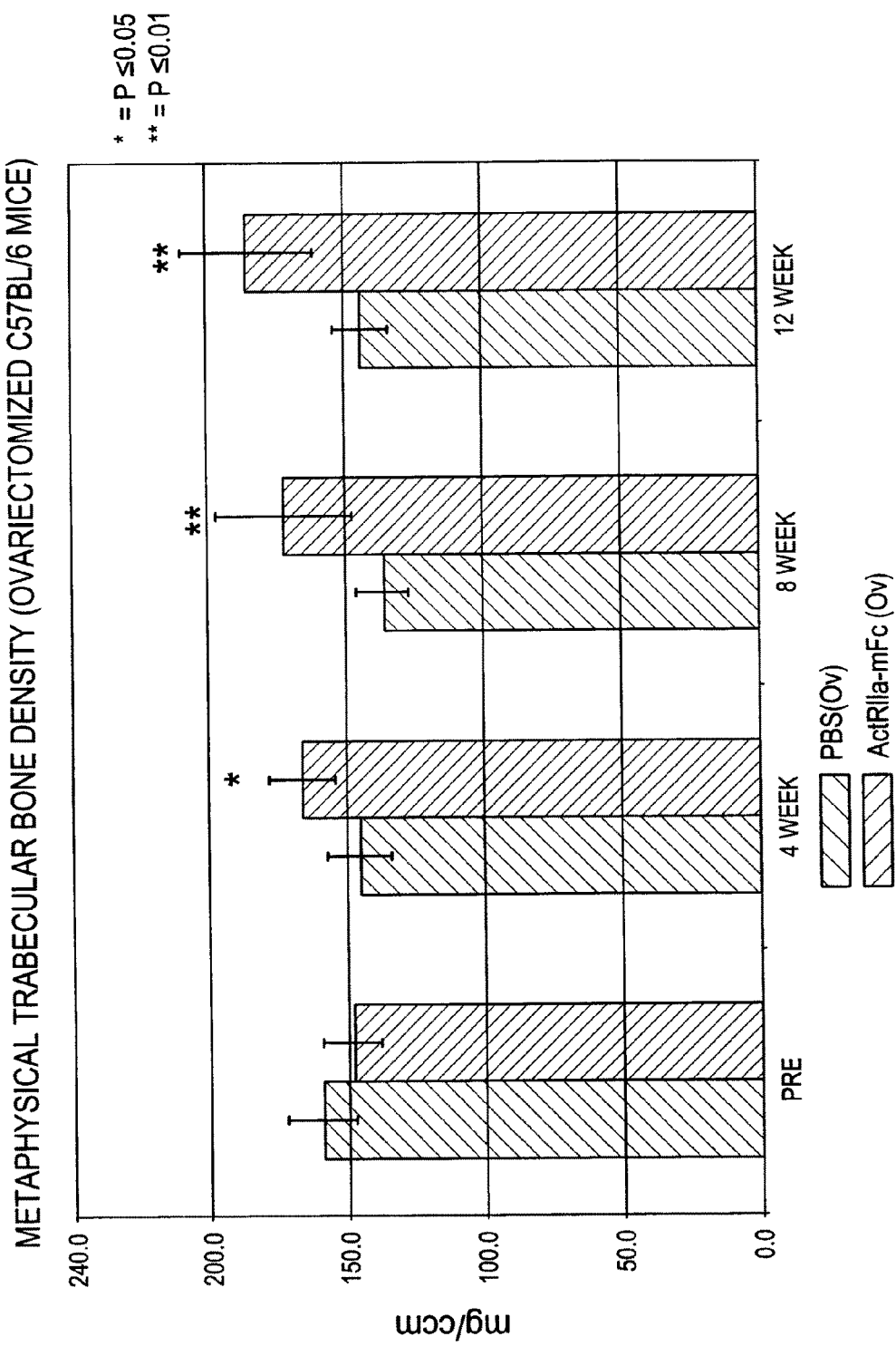
FIG. 12 shows the results of pQCT analysis of bone density in ovariectomized mice over 12 weeks of treatment. Treatments were control (PBS; pale bars) or ActRIIa-mFc (dark bars). y-axis: mg/ccm

In an additional set of experiments, ovariectomized (OVX) or sham operated mice as described above were treated with ActRIIa-mFc (10 mg/kg, twice weekly) or control (PBS) over twelve weeks. Similar to the results described above for ActRIIa-mFc, OVX mice receiving ActRIIa-mFc exhibited an increase in trabecular bone density of 15% by as early as four weeks and 25% after 12 weeks of treatment (FIG. 12).

Figure 13:
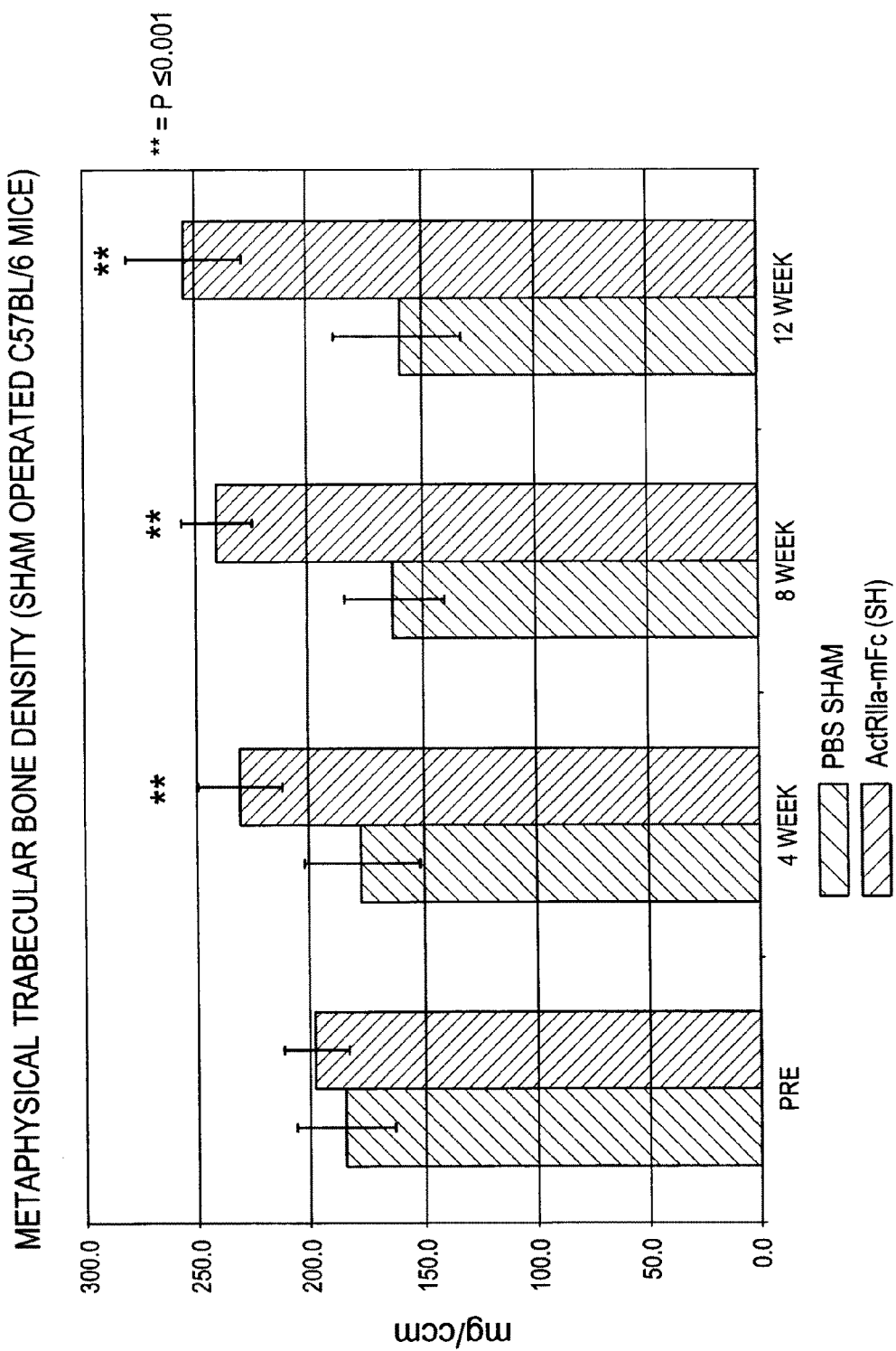
FIG. 13 depicts the results of pQCT analysis of bone density in sham operated mice over 12 weeks of treatment. Treatments were control (PBS; pale bars) or ActRIIa-mFc (dark bars). y-axis; mg/ccm

Sham operated mice receiving ActRIIa-mFc similarly showed an increase in trabecular bone density of 22% by as early as four weeks and of 32% after 12 weeks of treatment (FIG. 13).

Figure 14:
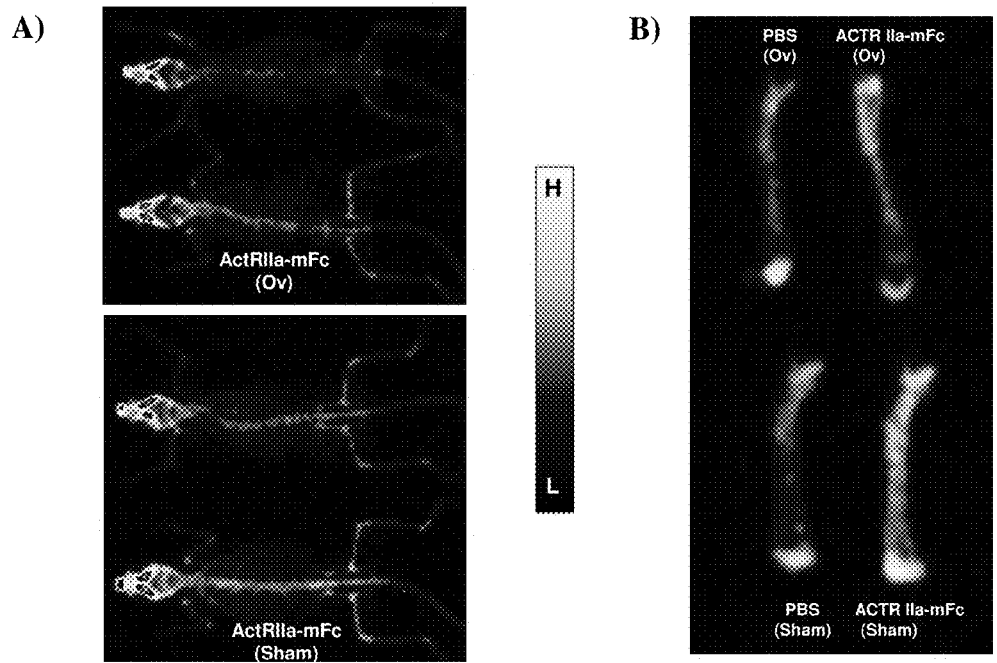
FIGS. 14A and 14B show whole body DEXA analysis after 12 weeks of treatment (A) and ex vivo analysis of femurs (B). Light areas depict areas of high bone density.
Figure 15:
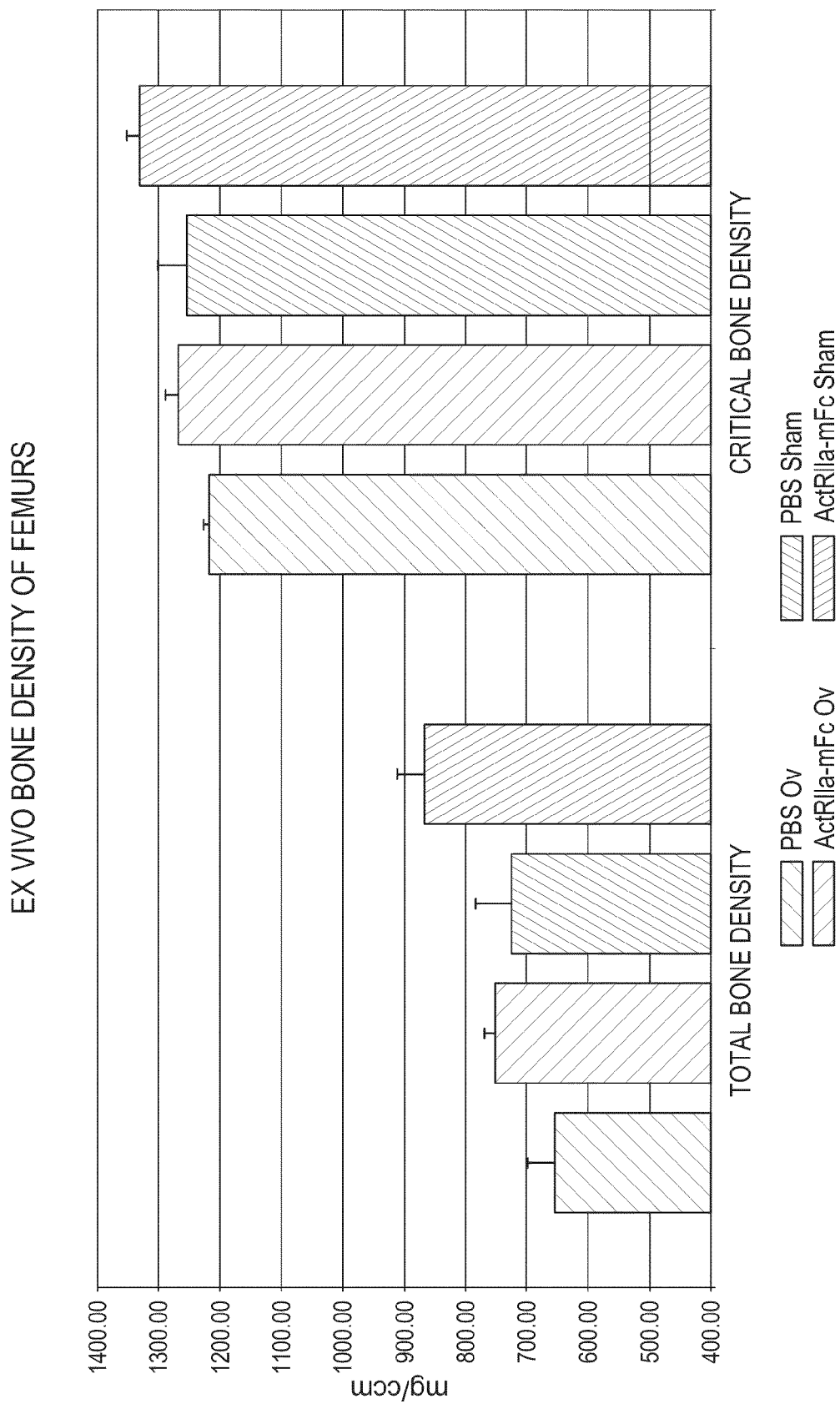
FIG. 15 shows ex vivo pQCT analysis of the femoral midshaft after twelve weeks of treatment. Treatments were vehicle control (PBS, dark bars) and ActRIIa-mFc (pale bars). The four bars to the left show total bone density while the four bars to the right show cortical bone density. The first pair of bars in each set of four bars represent data from ovariectomized mice while the second pair of bars represent data from sham operated mice.
Figure 16:
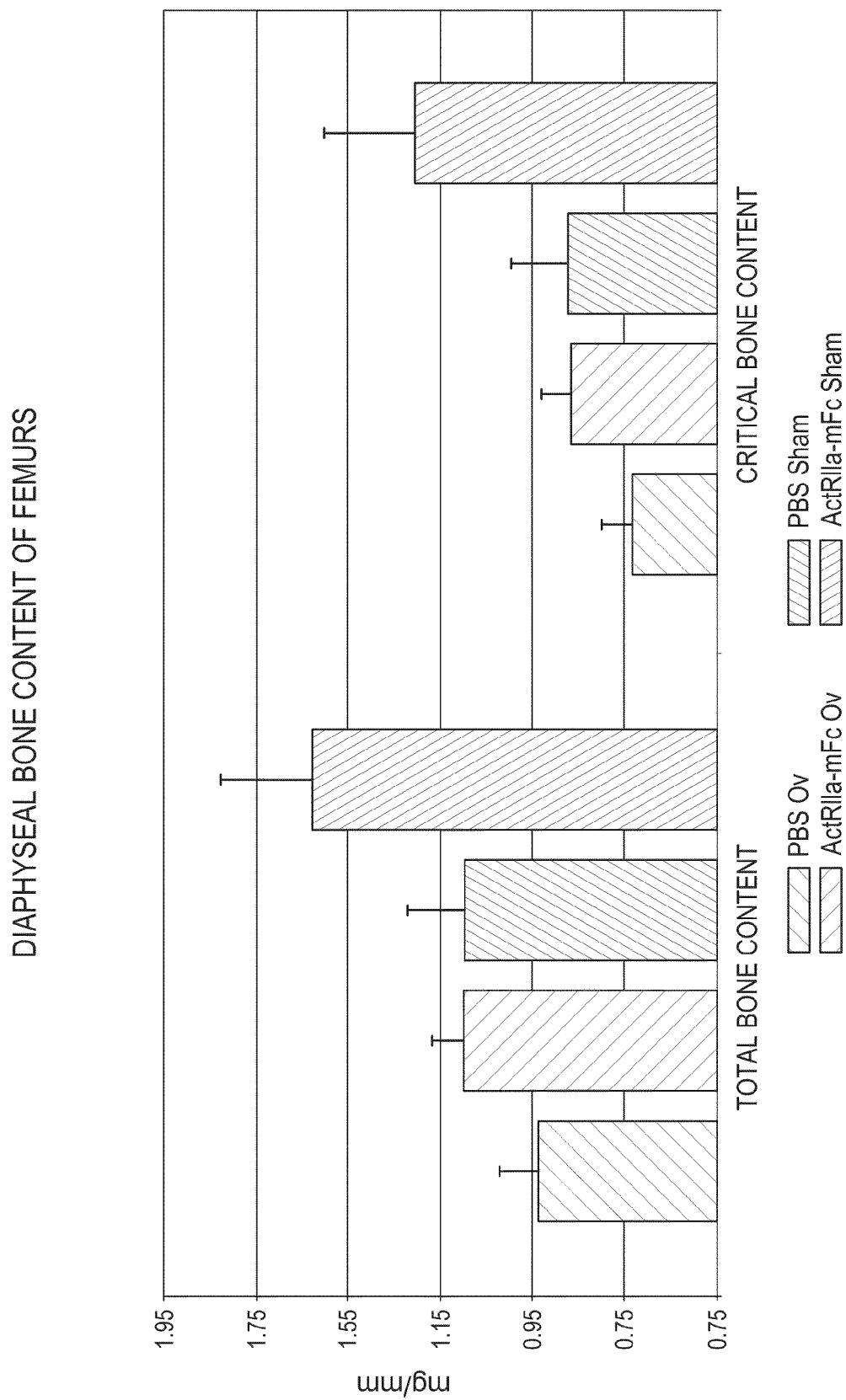
FIG. 16 shows ex vivo pQCT analysis and diaphyseal bone content of the femoral midshaft after twelve weeks of treatment. Treatments were vehicle control (PBS, dark bars) or ActRIIa-mFc (pale bars). The four bars to the left show total bone content while the four bars to the right show cortical bone content. The first pair of bars in each set of four bars represent data from ovariectomized mice while the second pair of bars represent data from sham operated mice.
Figure 17:
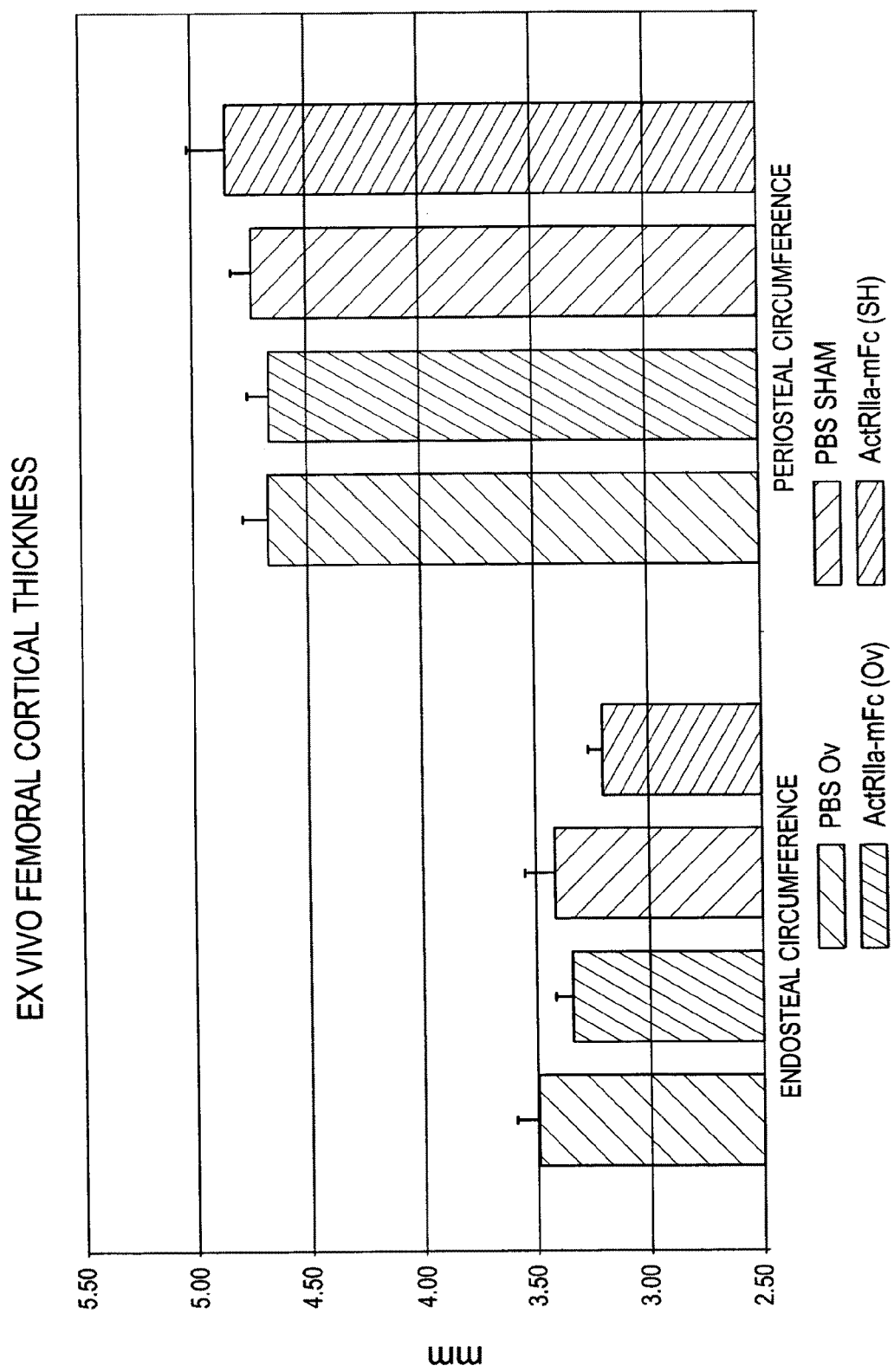
FIG. 17 shows ex vivo pQCT analysis of the femoral midshaft and femoral cortical thickness. Treatments were control (PBS, dark bars) and ActRIIa-mFc (pale bars). The four bars to the left show endosteal circumference while the four bars to the right show periosteal circumference. The first pair of bars in each set of four bars represent data from ovariectomized mice while the second pair of bars represent data from sham operated mice.

After twelve weeks of treatment with ActRIIa-mFc, whole body and ex vivo femur DEXA analysis showed that treatment induces an increase in bone density in both ovariectomized and sham operated mice (FIGS. 14A and 14B, respectively). These results are also supported by ex vivo pQCT analysis of the femoral midshaft which demonstrated a significant increase in both total and cortical bone density after twelve weeks of treatment with ActRIIa-mFc. Vehicle-treated control ovariectomized mice exhibited bone densities that were comparable to vehicle-treated control sham operated mice (FIG. 15). In addition to bone density, bone content increased following ActRIIa-mFC treatment. Ex vivo pQCT analysis of the femoral midshaft demonstrated a significant increase in both total and cortical bone content after twelve weeks of treatment with ActRIIa-mFc while both ovariectomized and sham operated vehicle control-treated mice exhibited comparable bone content (FIG. 16). Ex vivo pQCT analysis of the femoral midshaft also showed that ActRIIa-mFc treated mice did not show a change in periosteal circumference; however ActRIIa-mFc treatment resulted in a decrease in endosteal circumference indicating an increase in cortical thickness due to growth on the inner surface of the femur (FIG. 17).

Figure 18:
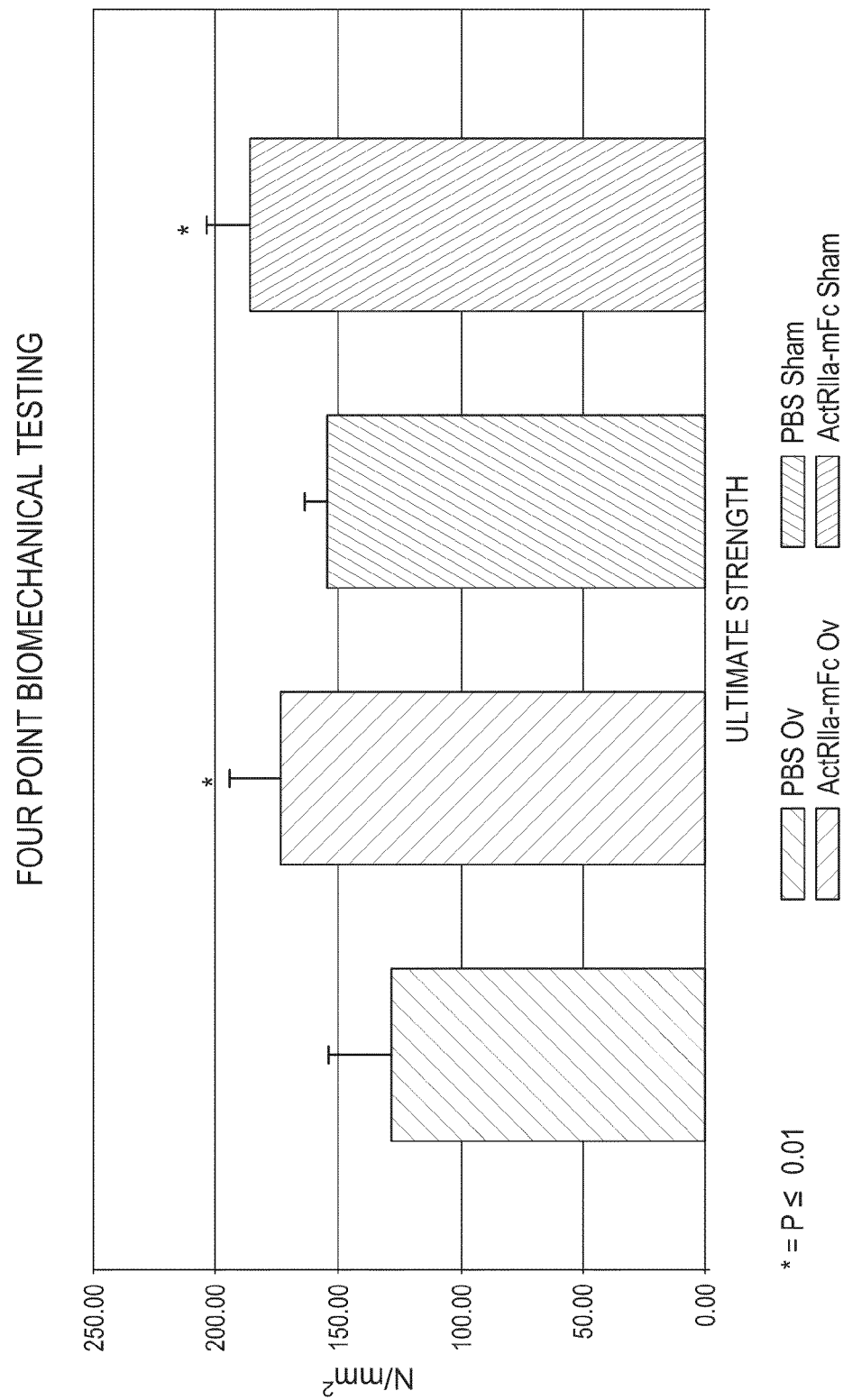
FIG. 18 depicts the results of mechanical testing of femurs after twelve weeks of treatment. Treatments were control (PBS, dark bars) and ActRIIa-mFc (pale bars). The two bars to the left represent data from ovariectomized mice while the last two bars represent data from sham operated mice.

Mechanical testing of femurs determined that ActRIIa-mFc was able to increase the extrinsic characteristics of the bone (maximal load, stiffness and energy to break) which contributed to a significant increase in the intrinsic properties (ultimate strength) of the bones. Ovariectomized mice treated with ActRIIa-mFc exhibited increased bone strength to levels beyond sham operated, vehicle treated controls, indicating a complete reversal of the osteoporotic phenotype (FIG. 18).

These data demonstrate that an activin-ActRIIa antagonist can increase bone density in normal female mice and, furthermore, correct defects in bone density, bone content, and ultimately bone strength, in a mouse model of osteoporosis.

Figure 22:
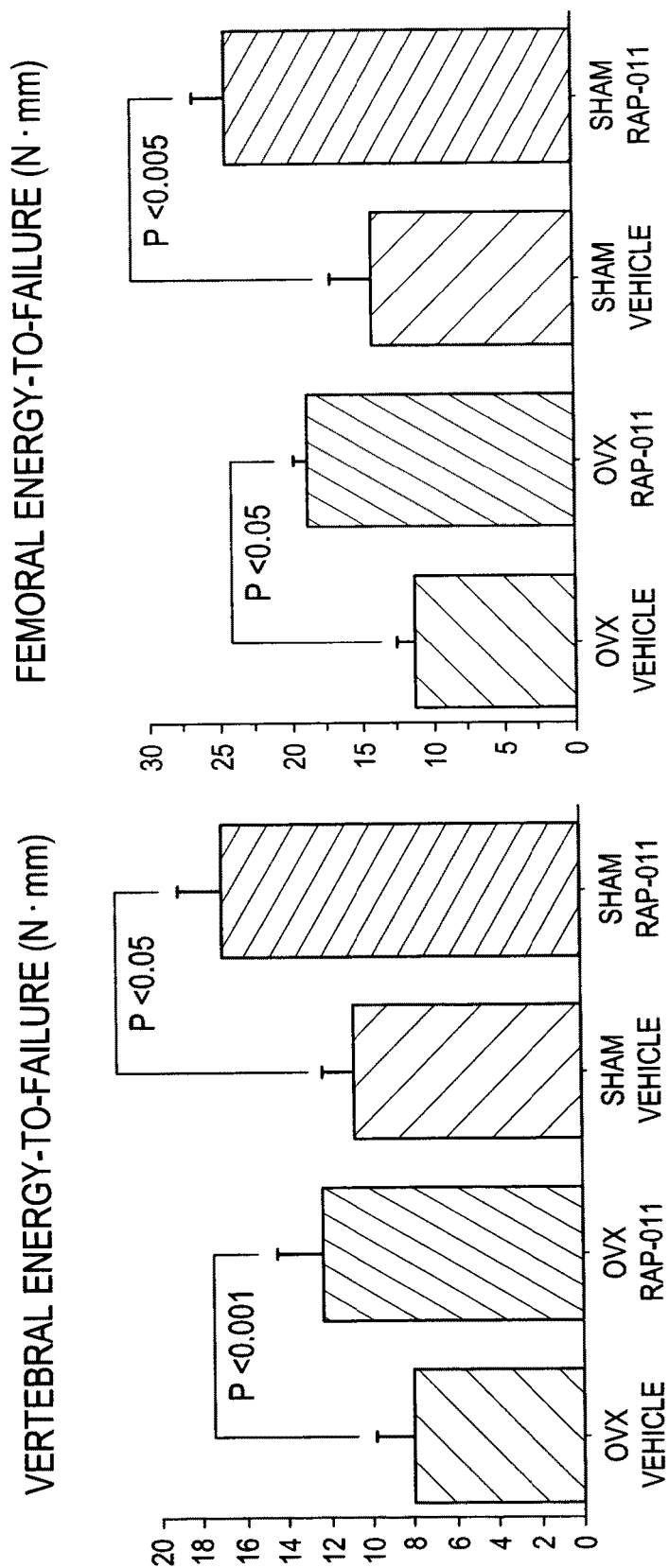
FIG. 22 shows the effects of ActrIIa-mFc on the mechanical strength of bone.
Figure 23:
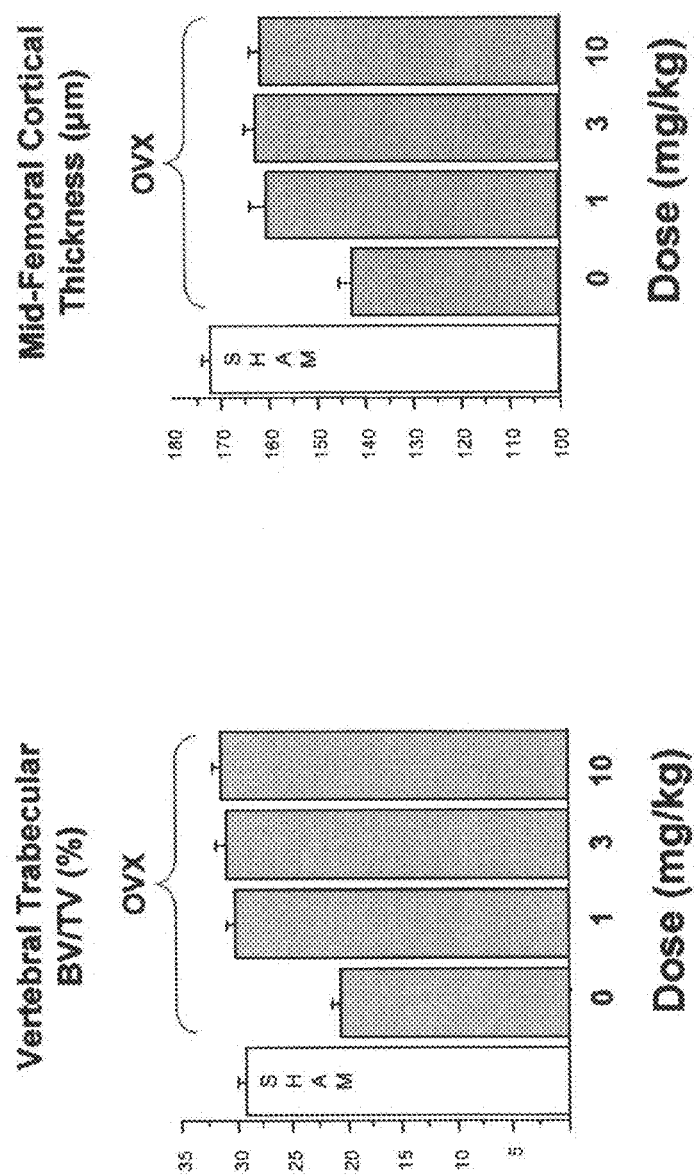
FIG. 23 shows the effects of different doses of ActRIIa-mFc on bone characteristics at three different dosages.

In a further set of experiments, mice were ovariectomized or sham operated at 4 weeks, and beginning at 12 weeks received either placebo or ActRIIa-mFc (2 times/week, 10 mg/kg) (also referred to as RAP-11 in FIGS. 19-24), for a further period of 12 weeks. A variety of bone parameters were evaluated. As shown in FIG. 19, ActRIIa-mFc increased vertebral trabecular bone volume to total volume ratios (BV/TV) in both the OVX and SHAM operated mice. ActRIIa-mFc also improved the trabecular architecture (FIG. 20), increased cortical thickness (FIG. 21) and improved bone strength (FIG. 22). As shown in FIG. 23, ActRIIa-mFc produced desirable effects at a range of doses from 1 mg/kg to 10 mg/kg.

Bone histomorphometry was conducted at a 2 week time point in sham operated mice. These data, presented in FIG. 24, demonstrate that ActRIIa-mFc has a dual effect, both inhibiting bone resorption and promoting bone growth. Thus ActRIIa-mFc stimulates bone growth (anabolic effect) and inhibits bone resorption (anti-catabolic effect). BV=Bone volume; TV=total tissue volume. BV/TV is a measure of the percentage of bone volume that is mineralized. ES=Eroded surface; BS=Bone surface. ES/BS is a measure of bone erosion, and the decrease caused by RAP-01 demonstrates an anti-resorptive or anti-catabolic effect. Ms/Bs is the mineralizing surface/bone surface ratio, which is an indicator of bone growth, or anabolic effect. Similarly, mineral apposition rate (MAR) and bone formation rate per bone surface per day (BFR/BSd) indicate bone growth. Measures of osteoblasts (Nob/BPm) and osteoclasts (Noc/BPm) are taken in order to probe the mechanism of action.

A second bone histomorphometry experiment was conducted in female C57BL/6 mice, beginning at an age of twelve weeks. Mice were dosed intraperitoneally twice per week with 10 mg/kg ActRIIa-mFc for two weeks, four weeks, eight weeks or twelve weeks. Each group was sacrificed five days after the last dose and bones taken for analysis. Mice were calcein labeled nine days and two days prior to euthanasia. As shown in FIG. 25, the metrics show that ActRIIa-mFc promotes bone growth and mineralization and has both anabolic and anti-catabolic effects. See for example the BV/TV ratio, the ES/BS ratio and the MS/BS ratio. The anabolic effects appear to persist throughout the dosing regimen, while the anti-resorptive effects appear to be shorter lived in the mice.

Example 3

ActRIIa-mFc Ameliorates or Prevents Bone Damage in a Murine Model of Multiple Myeloma Multiple myeloma patients exhibit a bone loss disorder characterized by increased osteoclast activity and decreased bone formation by osteoblasts. The 5T2MM model of myeloma in mice is based on the use of tumor cells (5T2MM cells) from a type of spontaneous tumor that develops in aged mice and causes effects in mice that are similar to those seen in human multiple myeloma patients. See, e.g., Vanderkerken et al., Methods Mol. Med. 2005; 113:191-205. ActRIIa-mFc was tested for effects in this model.

5T2MM cells injected into C57Bl/KaLwRij mice promoted an increase in osteoclast surface, the formation of osteolytic lesions and caused a decrease in bone area. Bone disease was associated with a decrease in osteoblast number, osteoblast surface and a reduction in mineralization.

Figure 26:
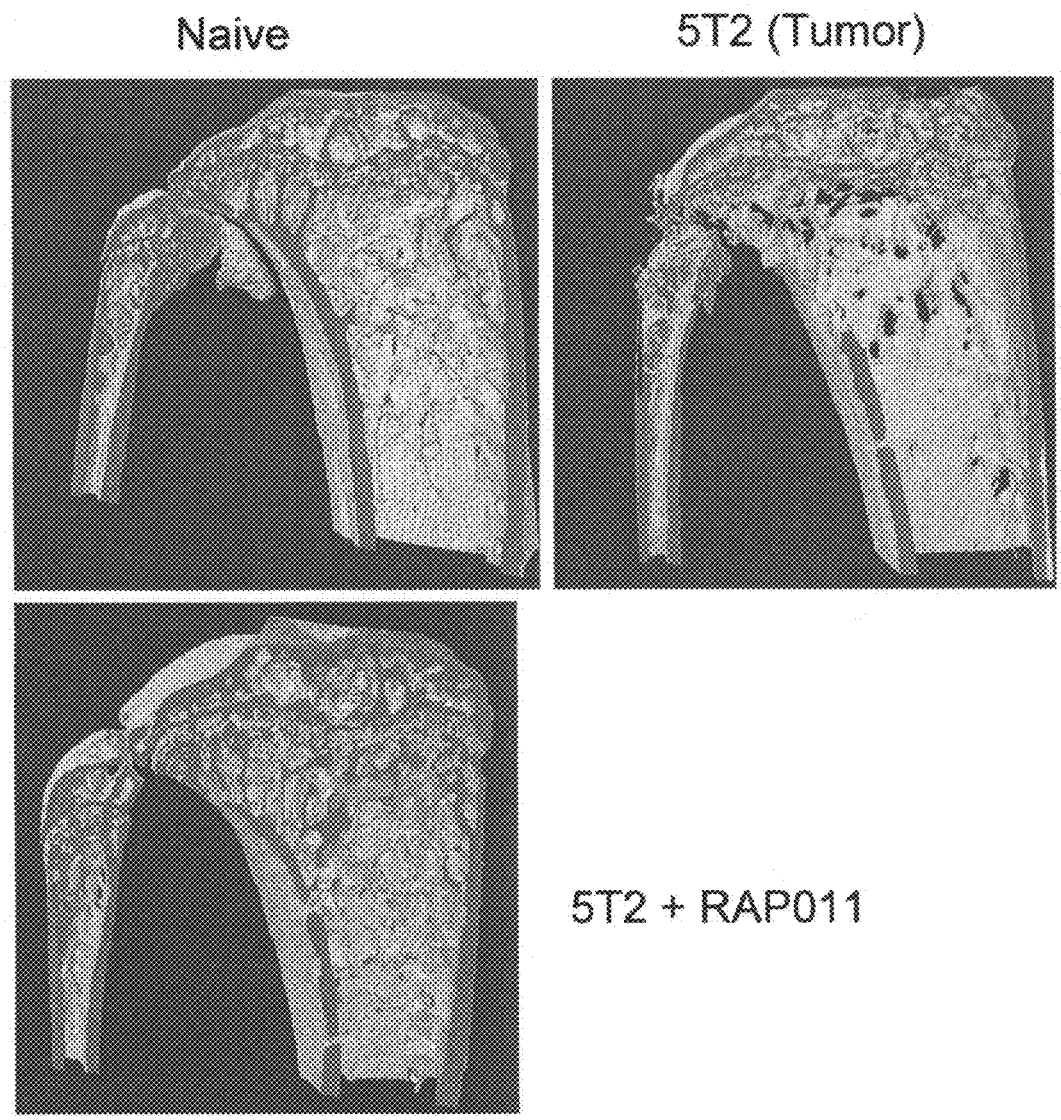
FIG. 26 shows images of mouse femurs from naïve and tumor-carrying mice, and the effects of ActRIIa-mFc treatment on bone morphology in the multiple myeloma model. Mice carrying multiple myeloma tumors (5T2) show marked pitting and degradation in the bone relative to normal mice (naïve). Treatment with ActRIIa-mFc eliminates this effect.

Mice bearing 5T2MM cells were treated with ActRIIa-mFc (RAP-011) (10 mg/kg, i.p. twice weekly), or a vehicle, from the time of 5T2MM injection, for a total of 12 weeks. MicroCT analysis of the proximal tibia and lumbar vertebrae demonstrated a 39% and 21% reduction in cancellous bone volume ($p<0.001$ and $p<0.01$) and a 37% and 15% reduction in trabecular number ($p<0.01$ and $p<0.05$) in 5T2MM-bearing mice compared to naïve mice. RAP-01 completely prevented 5T2MM-induced decreases in trabecular volume and number in both tibia ($p<0.001$ and $p<0.05$) and vertebrae ($p<0.01$ and $p<0.05$) when compared to vehicle treated mice. Bone volume was 19% higher in the tibia (p=168) and 12% higher in vertebrae ($p<0.05$) of RAP-011 treated mice when compared to naïve mice. RAP-011 prevented the development of osteolytic bone lesions ($p<0.05$). This effect is illustrated in FIG. 26. While a preliminary assessment of the data failed to identify significant effects on serum paraprotein (a biomarker of multiple myeloma tumor cells) or myeloma burden in this study, a further analysis indicated that serum paraprotein was substantially decreased in all but one of the treated animals, and further that the volume of healthy bone marrow was substantially increased, indicating a decrease in the myeloma tumor cell burden.

Therefore, ActRIIa-mFc may be used to decrease the effects of bone disease resulting from multiple myeloma and to treat the tumor cells themselves.

Example 4

Characterization of an ActRIIa-hFc Protein

ActRIIa-hFc fusion protein was expressed in stably transfected CHO-DUKX B11 cells from a pAID4 vector (SV40 ori/enhancer, CMV promoter), using a tissue plasminogen leader sequence of SEQ ID NO:9. The protein, purified as described above in Example 1, had a sequence of SEQ ID NO:7. The Fc portion is a human IgG1 Fc sequence, as shown in SEQ ID NO:7. Sialic acid analysis showed that the protein contained, on average, between about 1.5 and 2.5 moles of sialic acid per molecule of ActRIIa-hFc fusion protein.

This purified protein showed a remarkably long serum half-life in all animals tested, including a half-life of 25-32 days in human patients (see Example 6, below). Additionally, the CHO cell expressed material has a higher affinity for activin B ligand than that reported for an ActRIIa-hFc fusion protein expressed in human 293 cells (del Re et al., J Biol. Chem. 2004 Dec. 17; 279(51):53126-35.) Additionally, the use of the tPa leader sequence provided greater production than other leader sequences and, unlike ActRIIa-Fc expressed with a native leader, provided a highly pure N-terminal sequence. Use of the native leader sequence resulted in two major species of ActRIIa-Fc, each having a different N-terminal sequence.

Example 5

Human Clinical Trial

The protein described in Example 5 was administered to human patients in a randomized, double-blind, placebo-controlled study that was conducted to evaluate, primarily, the safety of the protein in healthy, postmenopausal women. Forty-eight subjects were randomized in cohorts of 6 to receive either a single dose of ActRIIa-hFc or placebo (5 active: 1 placebo). Dose levels ranged from 0.01 to 3.0 mg/kg intravenously (IV) and 0.03 to 0.1 mg/kg subcutaneously (SC). All subjects were followed for 120 days. Subjects were excluded from study participation if they took medications affecting bone metabolism within 6 months of study entry. Safety evaluations were conducted following each cohort to determine dose escalation. In addition to pharmacokinetic (PK) analyses, the biologic activity of ActRIIa-hFc was also assessed by measurement of biochemical markers of bone formation and resorption, and FSH levels.

No serious adverse events were reported in this study. Adverse events (AEs) were generally mild and transient. Preliminary analysis of AEs included headache, elevated laboratory values, cold symptoms, emesis or vomiting, intravenous infiltration, and hematoma at injection site.

Figure 27:
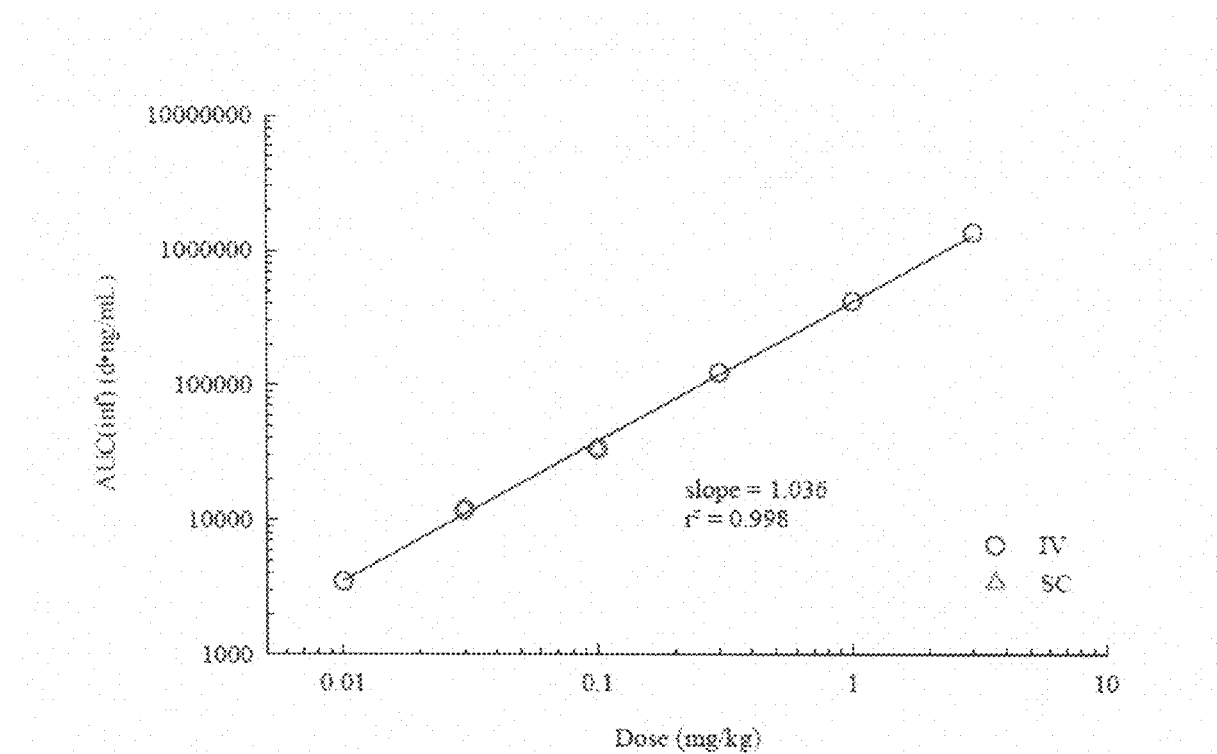
FIG. 27 shows results from the human clinical trial described in Example 6, where the area-under-curve (AUC) and administered dose of ActRIIa-hFc have a linear correlation, regardless of whether ActRIIa-hFc was administered intravenously (IV) or subcutaneously (SC).
Figure 28:
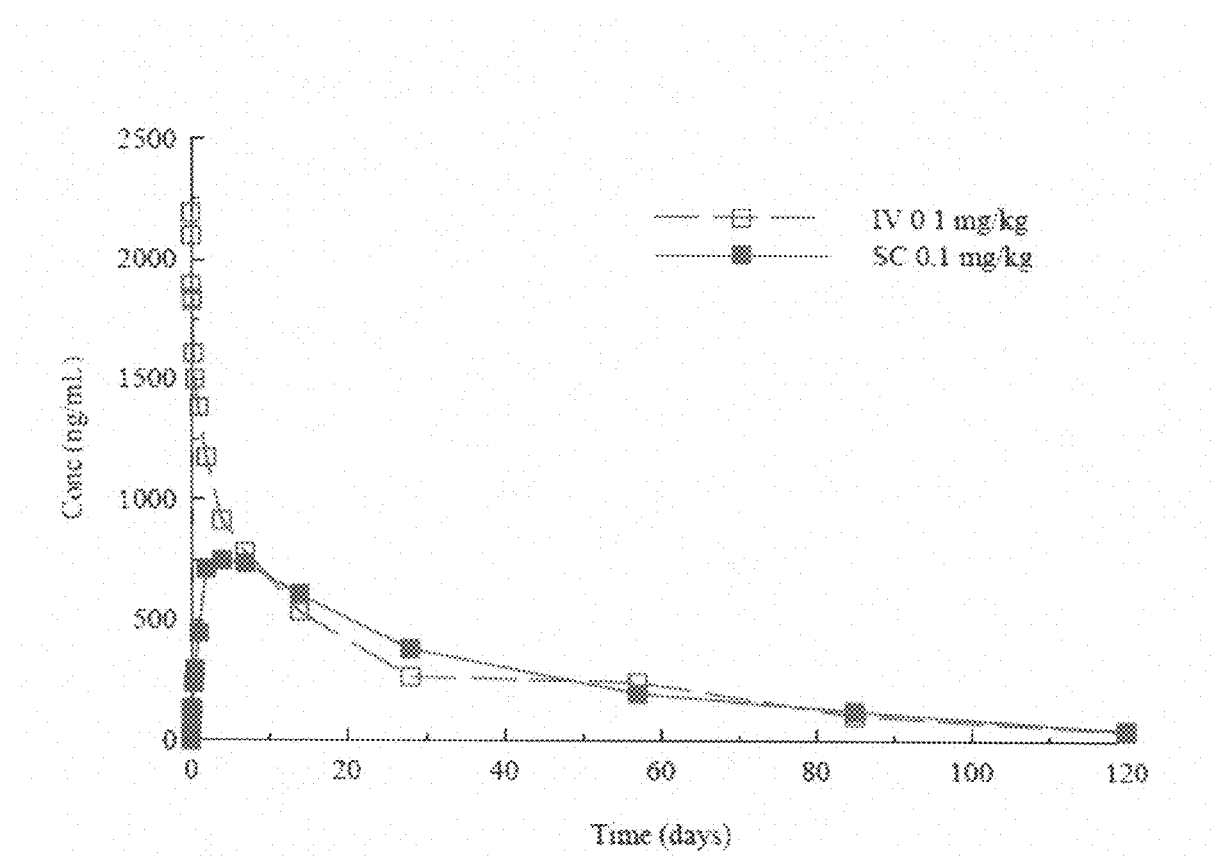
FIG. 28 shows a comparison of serum levels of ActRIIa-hFc in patients administered IV or SC.
Figure 29:
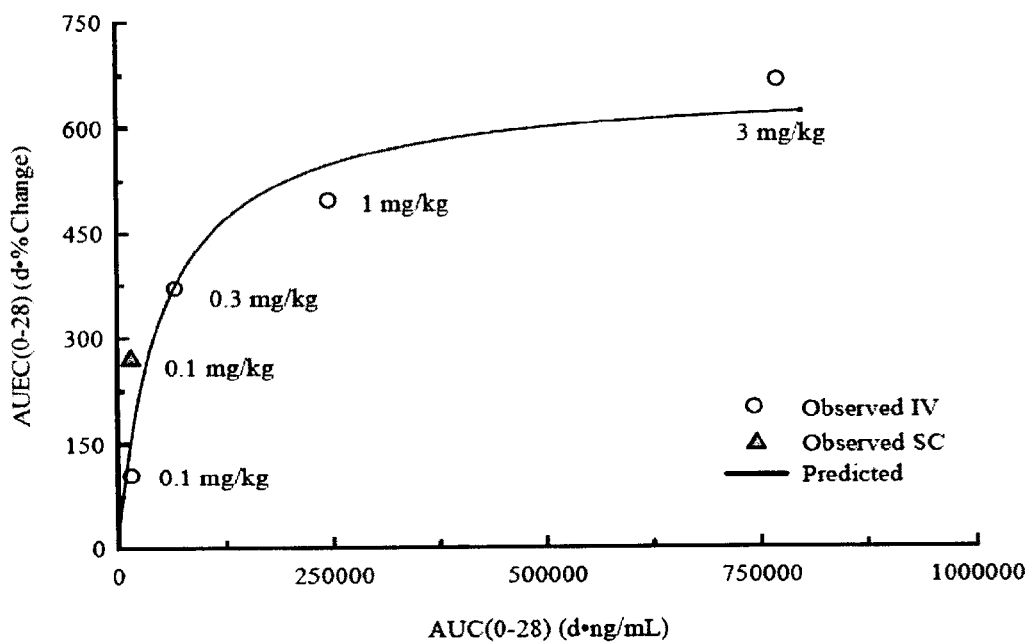
FIG. 29 shows bone alkaline phosphatase (BAP) levels in response to different dose levels of ActRIIa-hFc. BAP is a marker for anabolic bone growth.

PK analysis of ActRIIa-hFc displayed a linear profile with dose, and a mean half-life of approximately 25-32 days. The area-under-curve (AUC) for ActRIIa-hFc was linearly related to dose, and the absorption after SC dosing was essentially complete (see FIGS. 27 and 28). These data indicate that SC is a desirable approach to dosing because it provides equivalent bioavailability and serum-half life for the drug while avoiding the spike in serum concentrations of drug associated with the first few days of IV dosing (see FIG. 28). ActRIIa-hFc caused a rapid, sustained dose-dependent increase in serum levels of bone-specific alkaline phosphatase (BAP), which is a marker for anabolic bone growth, and a dose-dependent decrease in C-terminal type I collagen telopeptide and tartrate-resistant acid phosphatase 5b levels, which are markers for bone resorption. Other markers, such as P1NP showed inconclusive results. BAP levels showed near saturating effects at the highest dosage of drug, indicating that half-maximal effects on this anabolic bone biomarker could be achieved at a dosage of 0.3 mg/kg, with increases ranging up to 3 mg/kg. Calculated as a relationship of pharmacodynamic effect to AUC for drug, the EC50 is 51,465 (day*ng/ml). See FIG. 29. These bone biomarker changes were sustained for approximately 120 days at the highest dose levels tested. There was also a dose-dependent decrease in serum FSH levels consistent with inhibition of activin. Substantial decreases in FSH levels were observed with doses of ActRIIa-hFc ranging from 0.10 mg/kg up to 3 mg/kg. Decreases in mean FSH levels of 30-40% were observed with 1 and 3 mg/kg dosing, and in individual patients at the 3 mg/kg dose, decreases of up to 50% of FSH relative to baseline were observed. It should be noted that post-menopausal women exhibit a relatively consistent elevated FSH level, making it relatively easy to observe the effects of the drug on FSH. In men and reproductively active women, the baseline FSH level may vary widely making it difficult to assess the specific degree of inhibition, but nonetheless, the activin-FSH signaling axis is intact in these individuals and it is expected that ActRIIa-hFc will inhibit FSH production to a significant degree even if it is difficult to quantify the effect on FSH in these populations.

Figure 32:
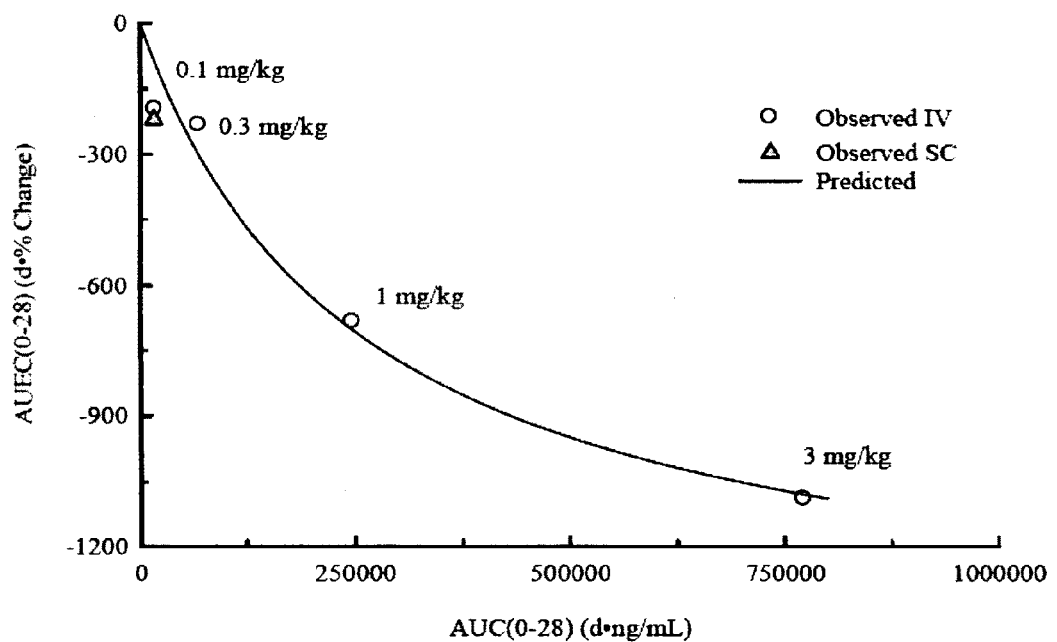
FIG. 32 shows an AUC analysis for the dose of ActRIIa-hFc that achieves varying degrees of effect on FSH levels.

Calculated as a relationship of pharmacodynamic effect to AUC for drug with respect to the effect on FSH, the EC50 is approximately 250,000 (day*ng/ml). See FIG. 32.

A single dose of ActRIIa-hFc given to healthy postmenopausal women was safe and well-tolerated for the range of dose levels tested. The prolonged PK and pharmacodynamic effects suggest that intermittent dosing would be appropriate for future studies. For example, dosing on the basis of serum half-life could be performed on a monthly basis, or on the order of once every two, three, four, five or six weeks. Additionally, because the pharmacodynamic effect extends far beyond the serum residence of the drug, dosing could be performed on the basis of the pharmacodynamic effect, meaning that dosing every three months or every two, three, four, five, six or even twelve months may be effective to produce the desired effect in patients. This clinical trial demonstrates that, in humans, ActRIIa-hFc is an osteoanabolic agent with biological evidence of both an increase in bone formation and a decrease in bone resorption.

Example 6

Co-administration of ActRIIa-mFc and a Bisphosphonate

Bisphosphonates are a class of drugs that are widely used to treat disorders associated with low bone mineral density, including osteoporosis and cancer-related bone loss. Bisphosphonates have a potent anti-resorptive activity, inhibiting osteoclasts. Perhaps because osteoclasts are required both for bone breakdown and bone growth, bisphosphonates appear to diminish the effects of parathyroid hormone (PTH), one of the only known anabolic bone growth agents (Black et al., N Engl J. Med. 2003 Sep. 25; 349(13):1207-15; Samadfam et al., Endocrinology. 2007 June; 148(6):2778-87.)

To test the utility of ActRIIa-Fc treatment in patients that had previously or were concomitantly receiving bisphosphonate or other anti-resorptive therapy, mice were tested with combined ActRIIa-mFc and zoledronate, a bisphosphonate compound. 12 week old C57BL/6N mice were treated as follows:

Group 1 PBS
Group 2 ActRIIa-mFc (RAP-011) (10 mg/kg) twice per week (with Group 3 and 4)
Group 3 Zoledronic Acid (ZOL) singe dose (20 mg/kg)
Group 4 ZOL (1 dose), 3 days later ActRIIa-mFc (RAP-011) (1 mg/kg) twice per week
Group 5 ZOL (1 dose), 3 days later ActRIIa-mFc (RAP-011) (10 mg/kg) twice per week
Total BMD was determined by DEXA scan (PIXI) prior to dosing and at 3 and 8 weeks of treatment.

Figure 30:
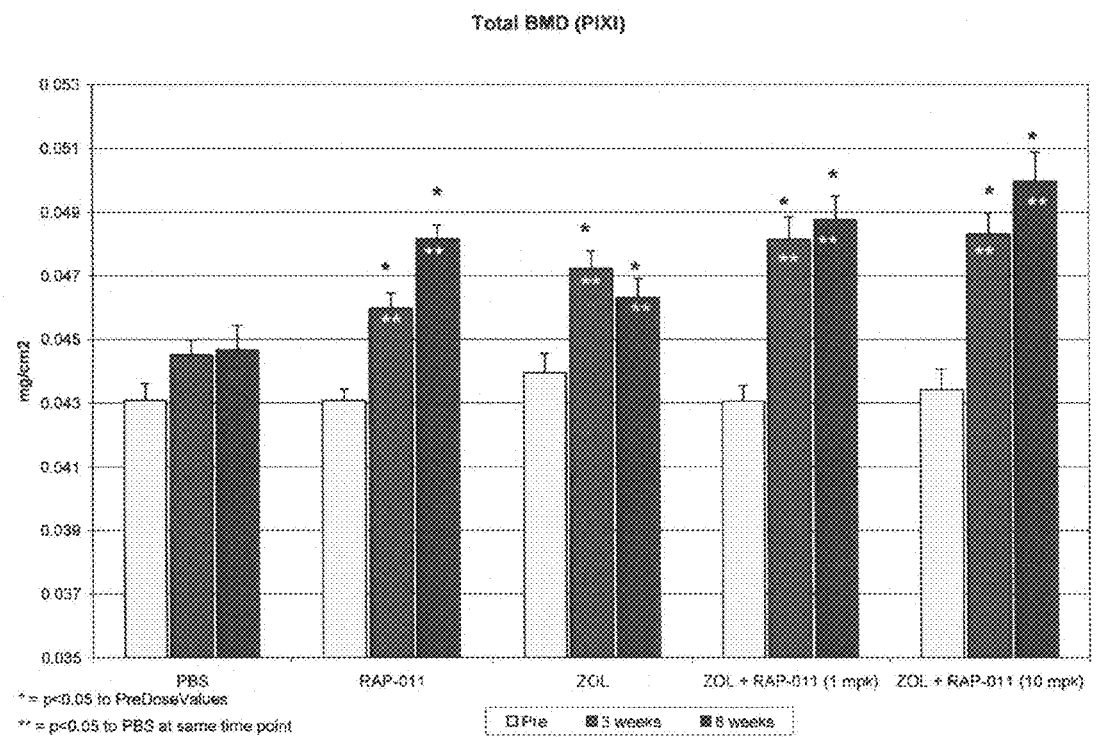
FIG. 30 shows the cooperative effects of ActRIIa-mFc (RAP-011) and a bisphosphonate agent (zoledronate) in mice.
Figure 31:
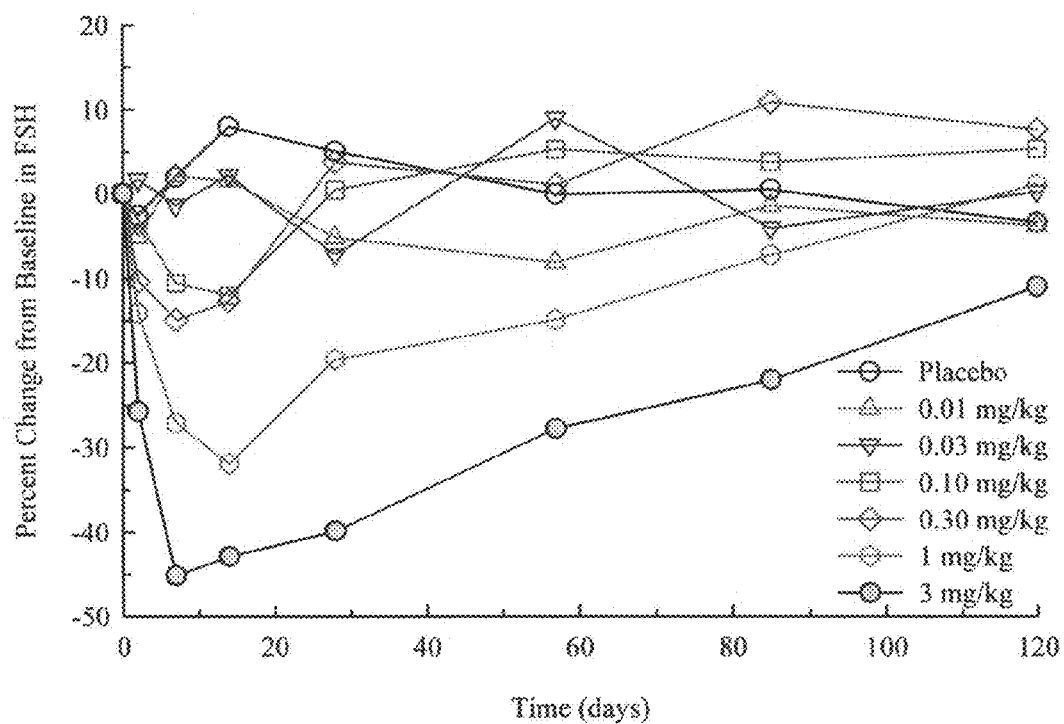
FIG. 31 shows results from the human clinical trial described in Example 6, showing that ActRIIa-hFc decreases FSH levels in a time- and dose-dependent manner.

As shown in FIG. 30, total BMD increased markedly in all treatment groups, with the combination of ZOL and ActRIIa-mFc producing the greatest effects. These results indicate that ActRIIa-Fc proteins can be used to increase bone density, even in patients that have received bisphosphonate therapy.

Example 7

Alternative ActRIIa-Fc Proteins

A variety of ActRIIa variants that may be used according to the methods described herein are descried in the International Patent Application published as WO2006/012627 (see e.g., pp. 55-58), incorporated herein by reference in its entirety. An alternative construct may have a deletion of the C-terminal tail (the final 15 amino acids of the extracellular domain of ActRIIa. The sequence for such a construct is presented below (Fc portion underlined) (SEQ ID NO: 12):

ILGRSETQECLFFNANWEKDRTNQTGVEPCYGDKDKRRHCFATWKNISGS
IEIVKQGCWLDDINCYDRTDCVEKKDSPEVYFCCCEGNMCNEKFSYFPEM
TGGGTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKE
YKCKVSNKALPVPIEKTISKAKGQPREPQVYTLPPSREEMTKNQVSLTCL
VKGFYPSDIAVEWESNGQPENNYKTTPPVLDSDGSFFLYSKLTVDKSRWQ
QGNVFSCSVMHEALHNHYTQKSLSLSPGK

INCORPORATION BY REFERENCE

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

We claim:

1. A method for decreasing follicle-stimulating hormone (FSH) levels in a human subject, the method comprising administering to a subject in need thereof an amount of an activin receptor type IIa-immunoglobulin Fc domain (ActRIIa-Fc) fusion protein effective to reduce FSH levels in the subject, wherein the ActRIIa-Fc fusion protein comprises an amino acid sequence that is at least 95% identical to the amino acid sequence of SEQ ID NO:3, wherein the amount administered results in an ActRIIa-Fc serum concentration of at least 1000 ng/mL, and wherein the ActRIIa-Fc fusion protein binds to activin.

2. The method of claim 1, wherein administration of the ActRIIa-Fc fusion protein alleviates or reduces at least one symptom of an FSH related disorder.

3. The method of claim 2, wherein the FSH related disorder is prostate cancer and administration of the ActRIIa-Fc fusion protein inhibits the progression of prostate cancer, delays the onset of metastasis, or decreases tumor size.

4. The method of claim 3, wherein the prostate cancer is hormone-refractory prostate cancer.

5. The method of claim 4, wherein the ActRIIa-Fc fusion protein comprises the amino acid sequence of SEQ ID NO: 7.

6. The method of claim 3, wherein at least 0.3 mg/kg of the ActRIIa-Fc fusion protein is administered to the patient.

7. The method of claim 3, wherein the ActRIIa-Fc fusion protein comprises the amino acid sequence of SEQ ID NO: 7.

8. The method of claim 2, wherein the FSH related disorder is FSH-secreting pituitary tumor.

9. The method of claim 8, wherein at least 0.3 mg/kg of the ActRIIa-Fc fusion protein is administered to the patient.

10. The method of claim 8, wherein the ActRIIa-Fc fusion protein comprises the amino acid sequence of SEQ ID NO: 7.

11. The method of claim 2, wherein the subject is a female afflicted with one or more ovarian cysts and administration of the ActRIIa-Fc fusion protein reduces the size of the cysts, inhibits growth of the cysts, or inhibits formation of new cysts.

12. The method of claim 11, wherein at least 0.3 mg/kg of the ActRIIa-Fc fusion protein is administered to the patient.

13. The method of claim 11, wherein the ActRIIa-Fc fusion protein comprises the amino acid sequence of SEQ ID NO: 7.

14. The method of claim 1, wherein the ActRIIa-Fc fusion protein comprises the amino acid sequence of SEQ ID NO:3.

15. The method of claim 1, wherein the ActRIIa-Fc fusion protein comprises the amino acid sequence of SEQ ID NO:2.

16. The method of claim 1, wherein the ActRIIa-Fc fusion protein is a dimer formed of two polypeptides that each comprise an amino acid sequence that is at least 95% identical to the amino acid sequence of SEQ ID NO:2.

17. The method of claim 16, wherein the ActRIIa-Fc fusion protein comprises three or more sialic acid moieties.

18. The method of claim 16, wherein the ActRIIa-Fc fusion protein is produced by expression in CHO cells.

19. The method of claim 16, wherein the ActRIIa-Fc fusion protein comprises between three and five sialic acid moieties.

20. The method of claim 16, wherein the ActRIIa-Fc fusion protein has a serum half-life of 25 to 32 days on average in normal, healthy humans and equivalent bioavailability when administered intravenously or subcutaneously.

21. The method of claim 20, wherein the ActRIIa-Fc fusion protein has four sialic acid moieties per dimer.

22. The method of claim 1, wherein the ActRIIa-Fc fusion protein comprises the amino acid sequence of SEQ ID NO:7.

23. The method of claim 22, wherein at least 0.3 mg/kg of the ActRIIa-Fc fusion protein is administered to the patient.

24. The method of claim 1, wherein at least 0.3 mg/kg of the ActRIIa-Fc fusion protein is administered to the patient.

25. The method of claim 1, wherein the ActRIIa-Fc fusion protein has a serum half-life of between 15 and 30 days.

26. The method of claim 25, wherein the ActRIIa-Fc fusion protein is administered to the subject no more frequently than once per week.

27. The method of claim 26, wherein at least 0.3 mg/kg of the ActRIIa-Fc fusion protein is administered to the patient.

28. The method of claim 25, wherein the ActRIIa-Fc fusion protein is administered to the subject no more frequently than once per month.

29. The method of claim 28, wherein at least 0.3 mg/kg of the ActRIIa-Fc fusion protein is administered to the patient.

30. The method of claim 1, wherein the ActRIIa-Fc fusion protein is administered subcutaneously.

31. The method of claim 30, wherein at least 0.3 mg/kg of the ActRIIa-Fc fusion protein is administered to the patient.

32. The method of any of claim 1, wherein the method causes less than 10% increase in the subject's skeletal muscle mass.

33. The method of claim 1, further comprising administering a radiation therapy, endocrine therapy or cytotoxic agent to the human subject.

34. The method of claim 33, wherein at least 0.3 mg/kg of the ActRIIa-Fc fusion protein is administered to the patient.

35. The method of claim 1, wherein the ActRIIa-Fc fusion protein comprises an amino acid sequence that is at least 95% identical to the amino acid sequence of SEQ ID NO:2.

36. The method of claim 1, wherein the ActRIIa-Fc fusion protein comprises an amino acid sequence that is at least 95% identical to the amino acid sequence of SEQ ID NO:7.

37. The method of claim 1, wherein the ActRIIa-Fc fusion protein comprises an amino acid sequence that is at least 95% identical to the amino acid sequence of SEQ ID NO:12.

38. The method of claim 1, wherein the ActRIIa-Fc fusion protein comprises the amino acid sequence of SEQ ID NO:12.

39. The method of claim 1, wherein the ActRIIa-Fc fusion protein has one or more of the following characteristics:
   i. binds to activin with a $K_D$ of at least $10^{-7}$ M; and
   ii. inhibits ActRIIa signaling in a cell.

40. The method of claim 1, wherein the ActRIIa-Fc fusion protein includes one or more modified amino acid residues selected from: a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent.

* * * * *